(12) United States Patent
Schultz-Cherry et al.

(10) Patent No.: US 7,381,524 B2
(45) Date of Patent: Jun. 3, 2008

(54) METHOD TO DETECT ANTIBODIES SPECIFIC FOR TYPE-2 TURKEY ASTROVIRUS

(75) Inventors: Stacey L. Schultz-Cherry, Oregon, WI (US); Matthew Koci, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 158 days.

(21) Appl. No.: 10/684,129

(22) Filed: Oct. 10, 2003

(65) Prior Publication Data

US 2005/0079485 A1 Apr. 14, 2005

(51) Int. Cl.
*C12Q 1/70* (2006.01)
*A61K 39/00* (2006.01)
*A61K 39/385* (2006.01)

(52) U.S. Cl. .................. 435/5; 424/184.1; 424/196.11
(58) Field of Classification Search ............ None
See application file for complete search history.

(56) References Cited

U.S. PATENT DOCUMENTS

| | | | | |
|---|---|---|---|---|
| 5,625,049 | A * | 4/1997 | Monroe et al. | 536/23.72 |
| 5,858,723 | A * | 1/1999 | Mueller-Lantzsch et al. | 435/69.3 |
| 6,696,562 | B1 * | 2/2004 | Schultz-Cherry et al. | 536/23.72 |

FOREIGN PATENT DOCUMENTS

WO  WO 92/20803  * 11/1992
WO  WO 9220803 A1 * 11/1992

OTHER PUBLICATIONS

Koci et al. (Journal of Virology. 2000; 74 (13): 6173-6177).*
Black et al., Antibody response to the M2 protein of influenza A virus expressed in insect cells, 1993, Journal of General Virology, vol. 74, pp. 143-146.*
Gulati et al., Development of a Highly Sensitive and Specific Enzyme-Linked Immunosorbent Assay Based on Recombinant Matrix Protein for Detection of Avian Pneumovirus Antibodies, 2000, Journal of Clinical Microbiology, vol. 38, No. 11, pp. 4010-4014.*
Koci, Matthew D., "Activation of macrophages by astrovirus through a replication-independent mechanism", *Thesis (Ph. D.)—University of Georgia*, 2003, ix, 194 leaves: ill. (some col.).
Koci, Matthew D., "Development of an RT-PCR diagnostic test for an avian astrovirus", *Journal of Virological Methods*, 90(79), (Oct. 2000), pp. 79-83.
Koci, Matthew D., et al., "Molecular characterization of an avian astrovirus", *Journal of Virology*, 74(13), (Jul. 2000), pp. 6173-6177.
Schultz-Cherry, S, et al., "Identifying agent(s) associated with poult enteritis mortality syndrome: importance of the thymus", *Avian Diseases*, 44(256), (Apr.-Jun. 2000), pp. 256-265.
Schultz-Cherry, S, et al., "Inactivation of an astrovirus associated with poult enteritis mortality syndrome", *Avian Diseases*, 44(76), (Jan.-Mar. 2001), pp. 76-82.
Giugni, T. D., et al., "Expression in Insect Cells and Immune Reactivity of a 28K Tegument Protein of Human Cytomegalovirus", *Journal of General Virology*, 73, (1992),2367-2374.
Inumara, S., et al., "Expression of Bluetongue Virus Group-Specific Antigen VP3 in Insect Cells by a Baculovirus Vector: Its Use for the Detection of Bluetongue Virus Antibodies", *J. Gen. Virol.*, 68, (1987),1627-1635.
Lee, T. W., "Astroviruses Detected by Immunofluorescence", *The Lancet*, (Aug. 20, 1977),p. 406.
Verschoor, E. J., et al., "Expression of Feline Immunodeficiency Virus gag and env Precursor Proteins in Spodoptera frugiperda Cells and Their Use in Immunodiagnosis", *Journal of Clinical Microbiology*, 31(9), (1993),2350-2355.
Von Messling, V., et al., "Rapid and Sensitive Detection of Immunoglobulin M (IgM) and IgG Antibodies Against Canine Distemper Virus by a New Recombinant Nucleeocapsid Protein-Based Enzyme-Linked Immunosorbent Assay", *Journal of Clinical Microbiology*, 37(4), (1999),1049-1056.

* cited by examiner

*Primary Examiner*—Bruce Campell
*Assistant Examiner*—Benjamin P. Blumel
(74) *Attorney, Agent, or Firm*—Schwegman, Lundberg & Woessner, P.A.

(57) ABSTRACT

A serological method to detect exposure to turkey astrovirus-2 (TAsV-2) is provided.

21 Claims, 26 Drawing Sheets

Figure 1:
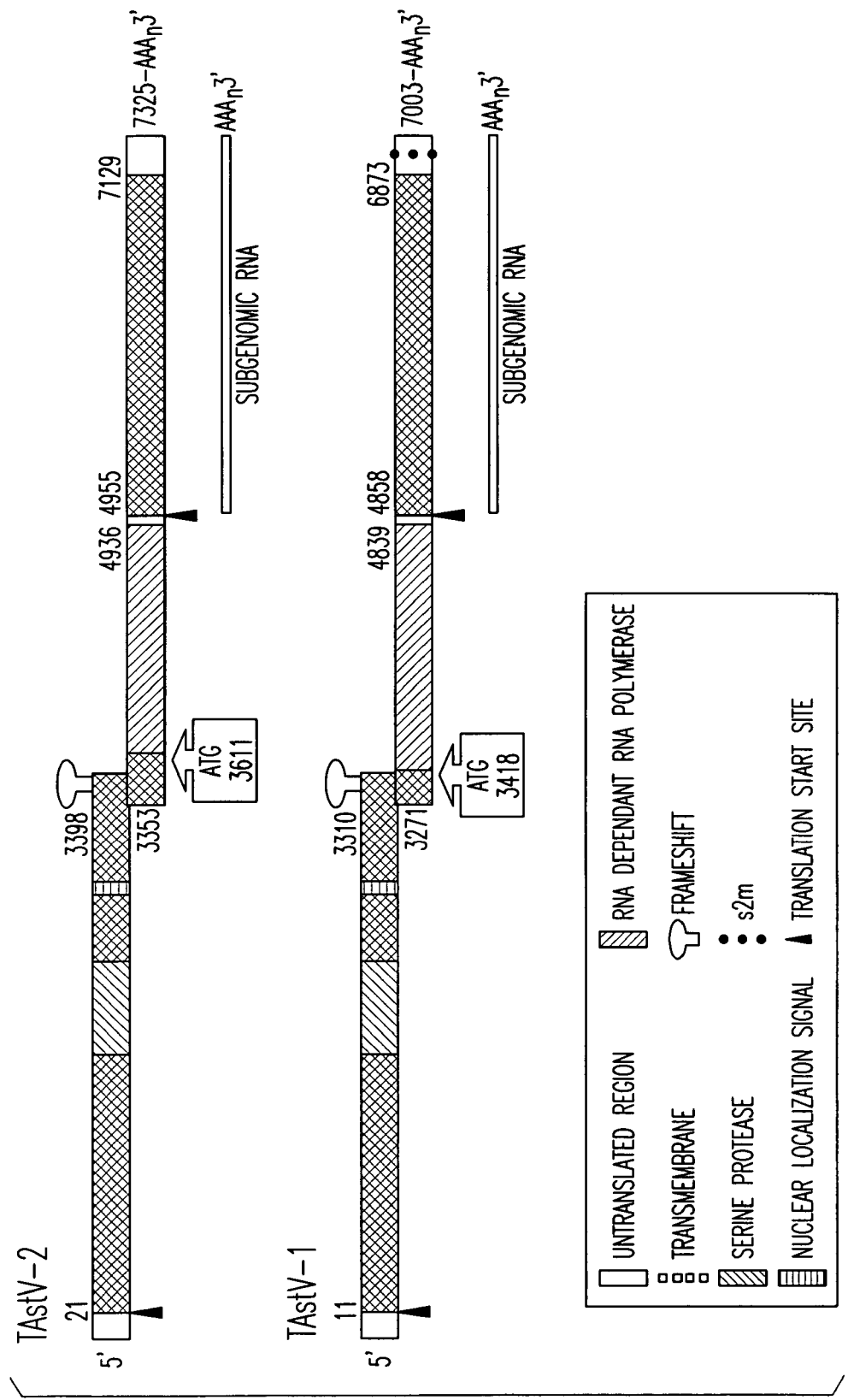

SEQIDNO:7     'MAQAGRSGDAFASLDQRRERQEEQAQSGLDKVFYFQGVVELFNR
MKIAYGRTPAWTALMKCNAIYLKDFKTAVGVEGTRYGLFFAEEVTKPTWSPDIGANLI
TLGEKACLDAQNAKYERLQASLKTTSGLVHQVMEKTREAKENLEKANKIQEQLDKVIE
SNKALHRKIQERNREKMQEYMVRLHNTQKDRDDWVQRCSRLEQENVTLQKRLKEKENA
LVSVGWDLLGWIVISVLVFGLISLADAQNLTPPAKIVITPGQAEFMDLAKLEKIQVRK
YRLDSCELPPEKGCVLYKDYLTTRPVSFLELMAKCSKPDWVSESSYNETTLMEECIQI
FGAEWCEGKLVDLVPRKCGEQHVLVNIIEQIEKTREVVTLIYGKVMSYRLDMWITSIF
SLVLAGNKEKLFKMAPFIFVAWFLNIPVFLTCVAVNIFPVVSLPFILFQIFMPQFVLV
NAFLLWLTLTLTAFYWSEGPKILMEISYALVYTIGFVLWSLGLAVGVTLKLTMVHQIL
MFCVVAAAICGTKFACTTITVQHPDGTTAKYTRVGKLKNNVVNQCKKVVTTLQTRGVI
PATPAKTASIVIVEGKNGTGVGFRFMNYILTAEHVVQGSDIATLKNGSVSVKSKVIKT
IPIFESVDNVAVLKLPPELNSVKPIKLAKKVQSDYLTLTAYDPNFQHAATFTGWCIID
GNWLNNSFDTKFGNSGAPYCDHDGRLVGIHLGTQGVLSQGIVIVDALKNTFQLADQCR
PQNFDMDEFLEKVIAGTKVSHAAILKELEELREEVQFLKKKCVTYDDYWLCQTIFGQA
KGKTKKTVRGRKHLVTKRALGKGHFMKMRMLTDEEYQNMIEKGFSAEEIREAVNALRE
QAWLNYCIDNDVDDEGEEDWYDDMVETDRVNQEIDEAIERAMEDRGEFYQKKSRLTFV
EQAMMHLIQVSKERSQTAKLEVQKENEAQLVKMFERCVTDENTPEGTTSIAALSTEDD
VRLVEGKVIDFTKAKNIPVDGEIRREIIPGTKCTEISTGPENKKNILKKKDTHIAEGK
VETKSSQQPVDVKDDKPVALEQRKPRACKWCGSSQKHDYRECRFQREKRFCVYCAAMH
SMFEGHIRPIECTSCKKSFSGIEKLEDHVVSGECQKN'

SEQIDNO:8     EVRRSCGQWRVSKKLIEGPVTTKAPTPVPDWLKIFAWEDDILPP
EGKTALPENVTLIGHIPVDKLVSRTKKVQDPLLGLVTPWKQDMYDSTTWTVKAYTKMF
EKFHYHDPVDFVEQYAEFVLLCDNMVLREHDYMANSNITPIMSTEKNVNSTPAYPKFQ
AYDSEAEYLEDCGWQEYLDVVSDPETINRRPLWWCFLKNEVLKREKIEDSDIRMILCT
DPIFTRIGAMFEQDQNNRMKQQTEIRSAQVGWTPFFGGLDRRVRRLYGDGDRYFVEMD
WTRYDGTIPKSLFWRIRQIRFFFLHDSHKTPKMRRLYNWYVKNLLEKIILLPTGEVCQ
VKKGNPSGQFSTTVDNNMINVWLTTFEVSYLFFKQRGRLPTEKELQENCSMICYGDDR
LLSIRKGFVEYEPDTVIDMYKNIFGMWVKRNNIKIQDTPEGLSFCGLTIVKSSTGAYV
GVPNVNKILSTLENPVRRLPDVESLWGKLVSLRILCENAPSNVKHFLDEQISNVEEFA
ARENIQLPEVGPDFYSRIW'

SEQIDNO:9     MAAMADKVVVKKTTTRRRGRSNSRSRSRSRSRSRTKKTVKIIEK
KPEKSILKKIDQAERRDAKQLRRIRKKVQGPPVNSRMTTVVTLGQITGNKDNTLERKH
KCFLNPLLMKSQETGQTATPLSVRASQYNLWKLSRLHVRLIPLAGKANILGSVVFLDL
EQEANTAGPESVDTIKARPHVEVPIGSKTVWKVHPRSALGPRQGWWNVDPGDSPTDSL
GPALNMWTYLQTVNALQSAGGTQTPYTSALFLVEVLVTYEFSNYGPKPALSQMVSDSF
PPASGSTATLKNTSDGAVAIQLSGAIARKMEEVEPKGRRSNAQTSGVGEVFWAVSTEV
VNTVADAIPGWGWLLKGGWFVLRKIFGAANDQNGTYLIYSSVADAQGDNRIYTSVKQT
QLTSSRINLVQLTQPNVNQAAVGGSVGAANSIYLPLPQADDQYTPYFVYNFQGERVST
TETGVFCLAAIPAATTSSRYNNQITTPSIGYRNASGTGTSFLLDAASWWNILDVTQTG
VLFGQPRLGVGVMQTMKTLKQHIKDYTEPAIQKYYPGTTNLDEQLKQRLNLAEGDPVI
SMGDTNGRRAALFYRTSDEKYILFFSTTEDPGAQYQNLKMLYFWNWSYSDTKQQFLDH
LRTVQFANLDDSQPAPYDSDDDDLSDVTSLFEQADLGDETDFKFNMSIQTSKHLEEEK
NYWKNQCERMMMEKALSGTSQPLVRFEKAGPRADQSSASGHS

FIG. 2A1

SEQIDNO:6

```
   1 ccgaaagtgt tgtcggggcg atggcccagg cgggtcgcag tggcgatgct tttgcatccc
  61 ttgatcaacg gcgggagcgc caagaagaac aggcgcagtc cggccttgac aaggtgttct
 121 acttccaagg cgtggttgaa ctattcaacc gtatgaaaat cgccatgga aggacaccgg
 181 cttggacggc cctcatgaag tgtaacgcca tatacttgaa agattttaaa acagcagttg
 241 gcgttgaggg tacccgctat gggctctttt tcgcagaaga agtgactaaa ccaacttggt
 301 cacccgacat tggagcaaac ttgataactt gggcgaaaa ggcctgttta gacgcccaaa
 361 atgcaaaata tgaaagattg caagcctcac ttaaaacaac tagtggcctt gtgcatcaag
 421 tgatggaaaa aactagggaa gctaaagaga acctagagaa agccaataag atccaagagc
 481 aacttgacaa ggtcattgag agcaacaaag ctttacaccg taagatacag gagagaaacc
 541 gagaaaagat gcaggaatac atggtaaggt tgcataacac gcagaaagat cgtgatgatt
 601 gggttcagag atgctccagg ttagaacagg agaatgtcac attgcagaaa aggttgaagg
 661 agaaagagaa cgcgctggta tctgttgggt gggatctttt aggctggata gttatttcag
 721 tgcttgtatt cggcctgatt tcactcgcag acgcgcaaaa cttgactcca ccagccaaga
 781 ttgtgataac tccagggcaa gcagagttca tggacctagc taaattggaa aaaatccagg
 841 tcagaaagta ccgactggat agttgtgaat taccacctga gaaaggttgc gtgttgtaca
 901 aggattacct taccaccagg ccggtaagct ttttggagtt gatggccaaa tgttcaaaac
 961 ctgactgggt ctcggagagc agttacaatg aaacaaccct aatggaagaa tgcatccaga
1021 tctttggtgc agagtggtgt gaagggaagc tcgttgatct tgtaccaaga aagtgtggcg
1081 agcaacatgt cttagttaac atcataggcc aaattgaaaa aaccagagaa gttgtgaccc
1141 ttatatatgg taaggtgatg tcatacaggc tagatatgtg gataacatct attttttagtt
1201 tagttttggc aggtaataag gaaaaattgt ttaaaatggc tcccttcatt tttgtagcat
1261 ggttttttaaa cataccagtg tttttaactt gtgtggcagt caacatttt ccagttgttt
1321 ccctgccttt cattttgttc cagattttta tgccacagtt tgttttggta aatgcctttc
1381 ttctatggtt aacactcact ttaacagcat tttattggag tgaggggccc aaaatactga
1441 tggagataag ttatgccctt gtgtatacca tcggctttgt tttatggtcc cttggactag
1501 ctgtggggt gacgctcaaa tgacaatgg tacatcagat attaatgttt tgtgttgttg
1561 ccgcagctat ttgcggaacc aagtttgcat gcacaacaat aacagtgcaa cacccagatg
1621 gaacaaccgc aaaatacacc cggttggta agctaaagaa taatgttgtg aaccagtgca
1681 aaaaggtagt cacgacattg cagacaagag gcgttatacc agcaacgcct gcgaaaacag
1741 catctattgt tattgttgag ggcaaaaatg aacaggtgt tgggttcagg tttatgaatt
1801 atattcttac agcagaacac gtggttcagg gatcagatat agcaacactt aaaaatggca
1861 gtgttagtgt gaaatccaaa gtcatcaaaa cgatcccaat atttgagagt gttgacaatg
1921 ttgcagtgtt aaaattgcca cctgagctca atagcgtgaa gcctatcaaa ttagcaaaga
1981 aggttcaaag tgactatctg acactgacag cctatgatcc aaatttcaa catgccgcca
2041 cttttaccgg gtggtgtatt atagatggaa attggcttaa taactccttt gatacaaaat
2101 ttgggaatag tggtgcacct tattgtgatc atgatggtag gctagttggt atccacctag
2161 gcacacaggg tgttctttcc caaggcatag tcattgtaga cgcattgaaa aatacattcc
2221 agcttgcgga tcagtgtaga ccacagaatt ttgacatgga tgagttcctt gagaaagtta
2281 tagcaggaac aaaagtgtca catgcagcga tcctaaaaga actgaagaa cttagagaag
2341 aggtgcaatt tttaaagaaa aaatgtgtca cctatgatga ctactggcta tgccaaacca
2401 tctttgggca ggccaaaggg aagacgaaga aaacagtcag aggccgtaaa caccttgtta
2461 ccaaaagagc tcttgggaaa ggccacttca tgaagatgag gatgctcact gatgaagaat
2521 atcagaatat gattgaaaag ggcttctcag cagaggaaat aagggaggca gtcaacgcac
2581 tccgagaaca agcatggctt aattattgta ttgataatga tgttgatgac gaaggtgagg
2641 aagattggta tgatgacatg gtagagacag atagagttaa ccaggagatc gatgaggcca
2701 tagagcgggc catggaagat cgtggtgagt ctctaccagaa gaaatcccgc cttacctttg
2761 ttgaacaggc catgatgcat ttgattcaag tgagcaagga gagccag actgctaaac
2821 tagaagttca aaaggagaat gaagcccaac tagtgaagat gtttgagcgg tgtgtcacag
2881 atgagaatac acctgagggt accacctcta tagcggcttt gtccacagaa gatgatgtta
2941 ggcttgttga agggaaagtc attgatttca ccaaagcaaa gaacatccca gttgacgggg
3001 aaattaggag agagatcatc cctggaacaa atgtactga gatttccact ggacctgaaa
3061 ataagaagaa catattgaag aaaaaggata cacacatagc tgagggtaaa gttgaaacta
3121 agtcatcaca gcagccggtt gacgtcaagg atgataaacc cgtagccttg gaacaacgta
3181 agcctagagc ttgtaaatgg tgcggttcat cacagaaaca tgattaccgg gaatgtcggt
3241 ttcaacgtga aaaacgcttt tgtgtgtatt gtgcagctat gcactcaatg tttgagggcc
3301 atataagacc aatagagtgc actagttgca agaaagttt tcaggaatt gagaagttag
3361 aagatcatgt ggtcagtgga gagtgtcaaa aaaactaata gaggggcctg tgacaacaaa
3421 ggcccctacc cccgtaccag attggcttaa aatatttgca tgggaagatg acatattacc
3481 acctgaaggt aaaactgcct taccagaaaa tgttactcta attggacata taccagttga
3541 taagttggtc tcgcgcacca agaaagtcca ggatccatta ttaggccttg taacaccatg
```

FIG. 2A2

```
3601 gaaacaagat atgtatgatt caacaacatg gactgtaaag gcttacacca aaatgtttga
3661 gaaattccat taccacgacc cagttgactt tgtggaacag tatgctgagt ttgtgctgtt
3721 gtgtgacaat atggtgttga gagagcatga ctatatggca aatagcaaca tcacaccaat
3781 catgtcaaca gagaaaaatg tcaatagtac accagcatac ccaaaattcc aagcctatga
3841 cagcgaagcc gagtatttgg aagattgtgg gtggcaagag tacctggatg ttgtgtctga
3901 tccagaaact ataaatcgta gaccctatg gtggtgcttc ctcaaaaatg aagttctcaa
3961 aagagagaaa attgaggaca gtgacattcg aatgatattg tgcaccgacc cgattttac
4021 caggattggg gctatgtttg agcaggatca gaacaacaga atgaaacaac agactgaaat
4081 aaggtctgca caggtcggat ggaccccctt tttcggcggc ttggatcgca gggttcgcag
4141 gttgtatggt gatggagata ggtattttgt tgagatggac tggacacggt atgatgggac
4201 tataccaaaa tcactatttt ggagaattag gcaaatcagg ttcttcttcc tccatgattc
4261 tcataagact ccaaagatgc ggcgcttgta caactggtat gtgaaaaatc tgttggaaaa
4321 aattatttta ttgccaactg gagaagtttg ccaggtcaag aaaggaaatc caagtggtca
4381 gttttcaaca actgtggata ataatatgat caatgtctgg ctaacaacat ttgaggtttc
4441 atacctattt ttcaaacagc gtggtagact gccaacagag aaagagctgc aagagaactg
4501 ctccatgata tgctacgggg atgacagact tcttccatc cgtaaagggt tgttgagta
4561 cgaacctgat acagtcattg atatgtacaa aaacatcttt ggaatgtggg tgaaaagaaa
4621 caacatcaaa atccaagata cacctgaagg gctctctttt tgtgggctta caatagtaaa
4681 atcaagtact ggtgcatatg ttggtgttcc caatgtgaac aaaatactgt caactttgga
4741 aaatccagta cgtaggctac cagatgttga gtctctttgg ggtaaattgg tttccctgcg
4801 catattgtgt gaaaatgctc ccagcaatgt taaacacttt cttgatgagc agattagcaa
4861 tgttgaggag ttcgccgcca gagaaaacat acaacttcct gaggtcgggc ccgacttcta
4921 ttccagaata tggtgagagg aggaccgaaa gaagatggcg gcgatggccg acaaggtcgt
4981 tgtcaagaag acaactacaa ggcgcagggg caggagtaat tcccgctccc gtagcaggag
5041 taggagcagg agcagaacta aaaagacagt caaaattatt gagaaaaagc cagaaaaatc
5101 catcctaaag aaaattgatc aggctgaaag aagagatgca aaacagctta ggcggattcg
5161 taagaaagtg cagggaccgc cagtaaattc caggatgaca acagtagtca cacttggtca
5221 gataacaggc aataaagaca cacccctaga gcggaaacac aagtgctttc tgaatccgct
5281 gttgatgaag agtcaggaaa ctggtcaaac tgcaacaccc ttatctgtta gggcatccca
5341 atataatctg tggaagctat ccagactcca tgtcagactt atacccttg caggaaaagc
5401 gaatattttg gggtcagtgg tgttcttaga tcttgaacag gaggcaaaca cagcaggacc
5461 agaatcagta gataccatca aggcaagacc ccatgttgaa gttcccatag ggtcgaaaac
5521 cgtttggaaa gtgcacccta gaagcgctct aggacctaga caggggtggt ggaatgttga
5581 ccctggtgac agcccaactg attctcttgg gccagcactc aacatgtgga cctacctgca
5641 aactgtcaat gcactccaga gcgctggggg cactcaaacg ccttacacca gtgcactttt
5701 tcttgtggag gtcttggtca cttatgagtt ttcaaactat ggcccaaagc ctgcactgtc
5761 tcaaatggta tcagacagct ttccaccagc ctccggttct actgcaacct taaaaaacac
5821 cagtgatggg gctgtagcaa tacaactctc aggcgctatc gcccgaaaga tggaggaggt
5881 tgagcccaag ggtaggcgct caaatgcgca aacatcaggt gtcggtgaag tgttctgggc
5941 agtgtccact gaagtagtca atacagtagc agatgccata ccaggctggg gctggctcct
6001 gaaaggtggc tggtttgtcc ttaggaaaat ctttggggcc gcaaatgacc agaatggcac
6061 ttacttgata tactcttcag tggcagtgc acaaggtgac aacaggatat acacatcagt
6121 gaaacagaca cagttgacat caagcaggat caacctcgtc caactcaccc agcccaatgt
6181 gaaccaagca gcagtaggtg gcagtgttgg tgcggcaaac tccatctatt tgccactacc
6241 acaagcagat gaccaataca caccctactt tgtctataat tttcaagggg aaagggtgtc
6301 aaccaccgag actggggtat tttgtctggc agccatacca gctgcgacta catctagtag
6361 gtataataat cagatcacca ctccatcaat tggctacagg aatgctagtg gtacaggaac
6421 atcattccta ctagatgctg catcatggtg gaatatattg gatgtaactc agactggagt
6481 gcttttttgga caaccaagat tgggtgttgg tgtcatgcag acaatgaaga ctctcaaaca
6541 gcatatcaag gattacacag agcctgcaat acagaaatat tatcctggaa caactaacct
6601 tgatgagcag ttgaagcaga gattgaacct ggcagagggt gacccggtca tctcaatggg
6661 ggacacaaac ggtaggaggg ctgcactctt ttataggact agtgatgaaa aatatatttt
6721 attttctca accacagaag atccagggc acagtatcaa aatctgaaaa tgttgtactt
6781 ctggaactgg tcctattctg acacaaaaca gcaatttttg gaccacctta gaacagtgca
6841 gtttgcaaat ttggatgaca gccagccagc cccctatgat agtgatgatg atgacctttc
6901 tgatgtaaca tcactttttg agcaggctga ttttgggggat gagacagact tcaaatttaa
6961 tatgtccatc caaacctcca aacatcttga ggaggagaaa aattactgga aaaaccagtg
7021 tgagaggatg atgatggaga aggcccttc gggcacctca cagcctcttg tccggtttga
7081 gaaagctgga cctagggcag accaatcttc tgccagtggt cattcttgaa tggccacact
```

FIG. 2A3

7141 ttctctgcgg tggaaatgga aatcaccatt ccacctaaga tgattagccg atccaacgga
7201 aatcacccgt tgggtggtgc gcggtttacg catcgggaaa tcaacccggt gtattacccg
7261 cacttccggc tcaacagttt tttaaaactg atataaattt atgaaaattt tattagcatt
7321 ttaagaaaaa aaaaaaaaaa aaaaaaaaaa aaaaa

FIG. 2A4

SEQIDNO:28

>TAstV2_2.seq
atggcggcgatggccgacaaggtcgttgtcaagaagacaactacaaggcgcaggggcaggagtaattcccgctcccgtag
caggagtaggagcaggagcagaactaaaaagacagtcaaaattattgagaaaaagccagaaaaatccatcctaaagaaaa
ttgatcaggctgaaagaagagatgcaaaacagcttaggcggattcgtaagaaagtgcagggaccgccagtaaattccagg
atgacaacagtagtcacacttggtcagataacaggcaataaagacaacaccctagagcggaaacacaagtgctttctgaa
tccgctgttgatgaagagtcaggaaactggtcaaactgcaacacccttatctgttagggcatcccaatataatctgtgga
agctatccagactccatgtcagacttatacccttgcaggaaaagcgaatattttggggtcagtggtgttcttagatctt
gaacaggaggcaaacacagcaggaccagaatcagtagataccatcaaggcaagaccccatgttgaagttcccatagggtc
gaaaaccgtttggaaagtgcacccctagaagcgctctaggacctagacaggggtggtggaatgttgaccctggtgacagcc
caactgattctcttgggccagcactcaacatgtggacctacctgcaaactgtcaatgcactccagagcgctgggggcact
caaacgccttacaccagtgcacttttcttgtggaggtcttggtcacttatgagttttcaaactatggcccaaagcctgc
actgtctcaaatggtatcagacagctttccaccagcctccggttctactgcaaccttaaaaaacaccagtgatggggctg
tagcaatacaactctcaggcgctatcgcccgaaagatggaggaggttgagcccaagggtaggcgctcaaatgcgcaaaca
tcaggtgtcggtgaagtgttctgggcagtgtccactgaagtagtcaatacagtagcagatgccataccaggctggggctg
gctcctgaaaggtggctggtttgtccttaggaaaatctttggggccgcaaatgaccagaatggcacttacttgatatact
cttcagtggcagatgcacaaggtgacaacaggatatacacatcagtgaaacagacacagttgacatcaagcaggatcaac
ctcgtccaactcacccagcccaatgtgaaccaagcagcagtaggtggcagtgttggtgcggcaaactccatctatttgcc
actaccacaagcagatgaccaatacacaccctactttgtctataattttcaaggggaaagggtgtcaaccaccgagactg
gggtatttgtctggcagccataccagctgcgactacatctagtaggtataataatcagatcaccactccatcaattggc
tacaggaatgctagtggtacaggaacatcattcctactagatgctgcatcatggtggaatatattggatgtaactcagac
tggagtgcttttttggacaaccaagattgggtgttggtgtcatgcagacaatgaagactctcaaacagcatatcaaggatt
acacagagcctgcaatacagaaatattatcctggaacaactaaccttgatgagcagttgaagcagagattgaacctggca
gagggtgacccggtcatctcaatggggggacacaaacggtaggagggctgcactcttttataggactagtgatgaaaata
tattttattttctcaaccacagaagatccaggggcacagtatcaaaatctgaaaatgttgtacttctggaactggtcct
attctgacacaaaacagcaattttggaccaccttagaacagtgcagtttgcaaatttggatgacagccagccagccccc
tatgatagtgatgatgatgacctttctgatgtaacatcactttttgagcaggctgatttggggggatgagacagacttcaa
atttaatatgtccatccaaacctccaaacatcttgaggaggagaaaaattactggaaaaaccagtgtgagaggatgatga
tggagaaggccctttcgggcacctcacagcctcttgtccggtttgagaaagctggacctagggcagaccaatcttctgcc
agtggtcattcttga

FIG. 2B1

SEQIDNO:10
>TX_ORF2.seq
ATGGCGGCGATGGCCGACAAGGTCGTTGTCAAGAAGACAACTACAAGGCGCAGGGGCAGGAGTAATTCCCGCTCCCGTAG
CAGGAGTAGGAGCAGGAGCAGAACTAAAAAgACAGTCAAAATTATTGAGAAAAAGCCAGAAAAATCCATCCTAAAGAAAA
TTGACCAGGCTGAAAGAAGAGATGAAAAGCAAATTAGGCGAATGCGGAAAAAATTGCAGGGGCCACCAGTAAATTCCAGG
ATGACAACAGTAGTCACACTTGGTCAGATAACAGGCAATAAAGACAACACCTTAGAGCGGAAACACAAGGTTTTTCTGAA
TCCACTGTTGATGAAGAGTCAGGAAACTGGTCAAACTGCAACACCCTTGTCTGTTAGAGCATCCCAATACAATCTGTGGA
AGCTATCCAGACTCCATGTCAGACTTATACCCCTTGCAGGAAAAGCGAATATTCTGGGGTCAGTGGTGTTTCTAGATCTT
GAACAAGAGGCAAATACAGCAGGACCAGAATCAGTAGATACCATCAAAGCAAGACCCCATGTTGAAGTTCCCATAGGGTC
GAAAACTGTTTGGAAAGTGCACCCTAGAAGTGCTCTGGGGCCTAGACAGGGGTGGTGGAATGTTGACCCTGGTGACAGCC
CAACTGATTCCCTTGGGCCAGCACTCAACATGTGGACCTACCTGCAAACTGTTAATGCACTCCAGAGCGCTGGGGGCAAC
CAAACACCTTACACCAGTGCACTTTTCCTTGTGGAGGTCTTGGTTACCTATGAGTTTTCAAATTATGGTCCAAAGCCTGC
ACTGTCCCAAATGATATCGGACAGTTTTCCACCAGCCTCCGGTTcTACTGCAACTCTTAAAAACACCAGTGATGGGGCTG
TAGCAATACAACTTTCAGGCGCTATCGCCCGAAAAATGGAGGAGCTTGAGCCTAAGGGTAGATGCTCAAATGCACAGACA
TCAGGTGTTGGAGAAGTGTTTTGGGCAGTGTCAACTGAGGTGGTTAACACAGTAGCAGATGCTATACCAGGTTGGGGTTG
GCTCTTGAAAGGTGGCTGGTTTGTCCTTAGAAAATTATTTGGAGCTGCGAATGACGCAAATGGCACCTACCTGTTATATT
CATCGGTGGCCGATGCACAGCAGGATAACAGATTATATACAAAAGTGAAACAAGGACAATTAACATCGAGTGTGATCAAC
CTCGTCCAACTCACTCAGCCCAATGTGAACCAAGCAgCAGtAGGTGGCAGTGTTGGCTCGGCAAATTCCATCTATTTGCC
ATTACCACAAGCAGATGACCAATATACACCCCATCTTGTTTATGATTTCCAAGGGAATAGGGTGTCAACCGCTGAGACTG
GGGTATTTTGTCTGGCATCCATACCAGCCGCAACTACATCCAGTAGGTACAATGGTCAAATCACCAGTCCTTCAATTGGC
TATAAGAGTGCTAGTGGCACAGGAACATCTTTCTCACTAGATGAAGCATCATGGTGGAACATCTTGGATGTAACTCAGAC
TGGGGTCCTCTTTGGACAACCAAAATTGGGCATTGGTGTCATGCAAACAATGAAGACCCTTAAACAACACATCAGGGATT
ATACAGAGCCTGCAATAAAAAAATATTACCCTGGAACAACTAACATTGCTGAAGAATTGAAACAGAGGATGAAACTGGCA
GAGGGTGATCCGGTCATCTCGATGGGAGACACAAATGGTAGGAGAGCTGCACTTTTTTATAGGACTAGTGATGAAAGGTA
CATTTTGTTCTTTTCAACAACAGGAGATCCAGGGTCACAATTTGAAAATTTGAAGATGTTGTACTTTTGGAACTGGTCCT
ATTCTGACAACAAACAGCAATTTCTGGACCGCCTTAGAACAGTGCAATTTGCAAATGCGGATGACAGCCAGCCAACCCCT
TGTGATAGTGATGATGATGACCTCTCTGATGTAACATCACTCTTTGAGCAGGCTGATTTGGGGGATGAGACAGATTTCAA
ATTTAATATGTCCATCCAGACCTCCAAACATCTTGAGGAGGAGAAAAATTACTGGAAAAACCAGTGTGAGAGGATGATGA
TGGAGAAGGCCCTCTCGGGCACCTCACAACCTCTTGTCCGGTTTGAGAAAGCTGGACTTAGGGCAGACCAATCTTCTGCC
AGTGGTCATTCTTGA SEQIDNO:11
>PA_ORF2.seq
ATGGCCGATAAGGTCGTTGTCAAGAAGACAACTACAAGGCGCAGGGGCAGGAGTAATTCCCGCTCCCGTAGCAGGAGTAG
GAGCAGGAGCAGAAATAGGGTTAGAAAGACAGTCAAAATTGTTGAGAAAAAGCCAGAAAAATCCATTTTGAAGAAAATTG
ACCAGGCTGAAAGAAGAGATGAAAAACAAATCAGGCGAATGCGGAAAAAATTGCAAGGACCACCAGTGAATTCCAGGATG
ACAACAGTGGTCACACTTGGTCAGATAACAGGTAACAAAGACAACACCCTAGAGCGGAAACATAAGTGCTTTCTGAATCC
GCTGTTGATGAAGAGTCAGGAAACCGGTCAAACTGCAACCCCCTTATCTGTTAGGGCATCCCAATATAATCTGTGGAAGC
TATCCAGACTCCATGTCAGACTTATACCCCTTGCAGGAAAAGCGAATATTTTGGGGTCAGTGGTTTTTCTAGATCTTGAG
CAGGAGGCAAATACAGCAGGACCAGAATCAGTAGATACCATCAAAGCAAGACCCCATGTTGAAGTTCCCATAGGGTCAAA
AACCGTCTGGAAAGTGCACCCTAGAAGTGCTCTAGGACCTAGACAGGGGTGGTGGAATGTTGATCCTGGTGACAGCCCAA
CTGATTCTCTTGGGCCAGCACTCAACATGTGGACCTACCTGCAAACTGTCAATGCACTCCAGAGCGCCACTGGTACACAA
ACACCGTACACCAGTGCACTTTTCCTTGTGGAGGTCTTGGTTACGTATGAGTTTTCAAATTATGGTCCAAAGCCCGCACT
GTCCCAGATGGTATCAGACAGCTTTCCACCAGCTTCCGGCTCTACTGCAACCTTAAAAAACACCAGTGATGGGGCTGTAG
CAATACAACTCTCAGGCGCTATTGCCCGAAAGATGGAGGAGGTTGAGCCCAAGGGTAGCGCTCAAATGCGCAAACATCAG
GTGTCGGTGAAGTGTTCTGGGCAGTGTCCACTGAAGTGGTCAACACAGTAGCAGATGCCATACCAGGCTGGGGCTGGCT
CCTGAAAGGTGGCTGGTTTGTCCTCAGGAAATCTTTGGGGCCGCGAATGACCAGAATGGCACTTACTTGATATACTCTT
CAGTGGCAGATGCACAAGGTGACAACAGGATATACACATCAGTGAAACAGACACAGTTGACATCAAGCAGGATCAACCTC
GTCCAACTCACCCAgCCCAATGTGAACCAAGCAGCAGTAGGTGGCAGTGTTGGTGCGGCAAACTCCATCTATTTGCCACT
GCCACAAGCAGATGATCAATACACACCCTATTTTGTTTATAATTTTCAAGGGGAAAGGGTGTCAACCACCGAGACTGGGG
TATTTTGTCTGGCAGCCATACCAGCAGCGACTACAACTAGTAGGTATAATAATCAGATCACCACTCCATCAATTGGCTAC
AGGAATGATAGTGGTACAGGAACATCATTCCTACTAGATGCTGCATCATGGTGGAATATATTGGATGTAACTCAAACTGG
AGTGCTCTTTGGACAACCAAGATTGGGTGTTGGTGTCATGCAGACAATGAAGACTCTTAAACAGCATATCAAGGATTATA CAGAGCCTGCAATACAGAAATATTATCCTGGAACAACCAACCTTGATGAGCAGTTGAAACAGAGATTGAACCTGGCAGAG
GGTGACCCGGTCATCTCAATGGGGGACACAACCGGTAGGAGGGCTGCACTCTTTTATAGGACTAGTGATGAAAAATATAT
TTTATTTTTCTCAACTACAGAAGATCCAGGGGCACAGTATCAAAATCTGAAAATGTTGTACTTTTGGAACTGGTCCTATT
CTGACACGAAACAGCAATTTTTGGACCACCTCAGAACAGTGCAGTTTGCAAATTGGATGACAACCATCCAGCCCCCTAT
GATAGTGATGATGATGACCTTTCTGATGTAACATCACTTTTTGAGCAGGCTGATTTGGGGGATGAGACAGACTTCAAATT
TAATATGTCCATCCAAACCTCCAAACATCTTGAGGAGGAGAAAAATTACTGGAAAAACCAGTGTGAGAGGATGATGATGG
AGAAGGCCCTTTCGGGCACCTCACAGCCTCTTGTCCGGTTTGAGAAAGCTGGACCTAGGGCAGACCAATCTTCTGCCAGT
GGTCATTCTTGAA

FIG. 2B2

SEQIDNO:12
>MN_ORF2.seq
ATGCTCTCCACAGCAATAACGGCACACAAACACCTTACACCAGTGCACTTTTCATTGTGCAGGTcTTGGTCACATATGAG
TTTTCAATCTATGGTCCCAAACCTGCACTGTCCCACGATGATTTGGGATAGCTTTCCACCAGCTGCTGGTTCAGAAGCAA
CTCTAAGGAACACCAGTGATTGGGTTGTTGCAGTGCAGCTTTCGGGTGGTATCGCCCGTAGGATGGAGGAAGTGTTGAAC
CTAAGAGCAGGCGGTCTAATGCACAGACATCAGGTGTTGGAAAAGTGTTTTGGGCAGTGTCTGACTGATGTAGTTAACAC
AGTAGCAGATGATATACCAGGGTGGGGTTGGCTtCCTGAAAGGTGGTTGGTTTGTGCCTTAGGTAAGATTTCCGCTGGTT
ATGAAGAGTCAGGAGACCGGCCAAACTGCGaACACCATTGTCAGTTAGGGCATCTCAGTATAATtCTGTGGAAGTTGTCC
AGACTCCATGTTAGGCTGATACCCcTTGCAGGAAAAGCAAACATCTTGGGATCAGTGGTGTTCTTAGATCTAGAGCAGGA
GTACGTGGCAGCgggACCAGAGTCTGTGGATACCATCAAAGCAAGACCCCATGTTGAAGTTCCTATTGGGGCGAAAACTG
TCTGGAAAGTGCACCCTAGAAGTGCCTTAGGTCCCAGACAAGGGTGGTGGAATGTTGACCCTGGTGATAGTCCAACTGAT
TCTCTTGGACCGGCACTTAACATGTGGACTTATTTGCAAACTGTCAATGCACTCCACAGCAATAACGGCACACAAACACC
TTACACCAGTGCACTTTTCCTTGTGGAGGTCTTGGTCACATATGAGTTTTCAAACTATGGTCCCAAACCTGCACTGTCCC
AGATGATTTCGGATAGCTTTCCACCAGCTGCTGGTTCAACTGCAACTCTAAAAAACACCAGTGATGGGGCTGTTGCAGTG
CAGCTTTCGGGTGCTATCGCCCGTAGGATGGAGGAGGTTGAACCTAAGAGCAGGCGGTCAAATGCACAGACATCAGGTGT
TGGAGAAGTGTTTTGGGCAGTGTCAACTGATGTAGTTAACACAGTAGCAGATGCTATACCAGGCTGGGGTTGGCTCCTGA
AAGGTGGCTGGTTCGTCCTTAGGAAGATATTTGGAGCTGCGAATGACGCAAATAGCACCTACCTGTTGTATTCATCGGTA
GCTGATGCACAGCAAGCAACAGAATaTATACAACAATAAAACAAGGACAAGGCAACTAACATCAAGTGTGATCAATCT
GGTTCAACTCACCCAGCCAAATGTAAATCAAGCAGCTGTTGGTGGTAGTGTTGGTTCTGCAAATTCCATCTACCTACCCT
TGCCACAAGCAGAGGAtCAATATACACCGCACTTTGTTTATGATTTCCAGGGAACGAGGGTGTCAACAACAGAGTCTGGA
GTCTTTTGCCTGTCCTCAATACCAAGTGCTGACAGTAAGAGCAGATATAACAACCAGATGAACTCTCCAACAGTGGGATA
TAAGaATgaAGGTgGTACTGGAACATCATTCGCTATGGACAATGCCCCGTGGTGGAGCATCCTGGATGTTACTCAAACAG
GTGTCATCTTTGGCCAGCCCAGGTTAGGTGTTGGGGTTATACAAACAATGAAAACACTGAAACAACACATTACAGATTTT
ACTGAACCTGCAGTAAAGAAATATTATCCTGGCACTACCAACTTGGACCAGACACTCAAAGATAGAATGAAATTAACAGA
AGGAGACCCGGTCGTCTCTATGGGAGATGTGACAGGGAGAAGAGCAGCACTCTTTTATAGAACTAGTGATGAGAGGTACA
TCTTGCTCATTTCATCAACAGAAGATCCCGGGTCACAATTTGAGAGGCTGAAGGTGACAACTTTCTGGAACTGGTCCCTT
TCTGACAACAAAAGTGAGTTCTTAAATAGGTTGAGAACCATACAGTATGCAAATGCACATCAAGAAGAAATGTCTCATTG
TGATAGCGACGATGATGGGCTGTCAGATGTAACGTCGCTGTTTGAACAGGCCGACCTGGAGGATGAGACAGATTTTAAAT
TTAAAATGTCTATTCAAACCTCTAAAGATCTTGAGGATGAGAAAAATTACTGGAAAAACCAGTGTGAGAGGATGATGATG
GAGAAGGCCCTTTCGGGCACCTCACAGCCTCTTGTCCGGTTTGAGAAAGCTGGACCTAGGGCAGACCAATCTTCTGCCAG
TGGTCATTTTTGA SEQIDNO:13
>MI_ORF2.seq
ATGGCGGCAATGGCCGACAAGGTCGTTGTTAAGAAGACAACTACAAGGCGCAGGGGCAGGAGTATTTCCCGCTCCCGTAG
CAGGAGTAGGAGCAGGAGCAGAACTAGGATTAAAAAGACAGTCAAGATTGTTGAGAAAAAGCCAGAAAAATCCATCTTAA
AGAAAATTGATCAGGCTGAAAGGAGAGATGAAAAGCAGATTAGGCGGATTCGCAAGAAAATGCAGGGACCGCCAGTGAAT
TCTAGGATGACAACAGTAGTCACACTTGGTCAGATAACAGGCAATAAAGACAACACCTTAGAGCGGAAACATAAGTGCTT
TCTGAATCCGCTGCTGATGAAGAGTCAGGAAACTGGTCAAACTGCAACACCCTTATCTGTTAGGGCATCCCAATATAATC
TGTGGAAGCTATCCAGACTCCATGTCAGACTTATACCCCTTGCAGGAAAAGCAAATATTTTGGGGTCAGTGGTGTTCCTA
GATCTTGAACAGGAGGCAAACACAGCAGGACCAGAATCAGTAGATACCATCAAAGCAAGACCCCATGTTGAAGTTCCCAT
AGGGTCAAAAACTGTTTGGAAAGTGCACCCTAGAAGTGCTCTAGGACCTAGACAGGGGTGGTGGAATGTTGATCCCGGTG ACAGCCCAACTGATTCTCTTGGGCCAGCACTCAATATGTGGACCTACCTGCAAACTGTCAATGCACTCCAGAGCACCAGT
GGTACACAAACACCTTATACCAGTGCACTTTTCCTTGTGGAGGTTTTGGTTACTTATGAGTTTTCAAATTATGGTCCAAA
GCCCGCACTGTCCCAGATGGTATCAGACAGCTTTCCACCAGCTTCCGGCTCTACTGCAACCTTAAAAAACACCAGTGATG
GGCTGTAGCAATACAACTCTCAGGCGCTATTGCCCGAAAGATGGAGGAGGTTGAGCCCAAGGGTAGGCGCTCAAATGCGG
CAAACATCAGGTGTCGGTGAAGTGTTCTGGGCAGTGTCCACTGAAGTAGTCAATACAGTAGCAGATGCCATACCAGGCTG
GGGCTGGCTCCTGAAAGGTGGCTGGTTTGTCCTCAGGAAAATTTTGGGGCCGCGAATGACCAGAATGGCACTTACTTGA
TATACTCTTCAGTGGCAGATGCACAAGGTGACAACAGGATATACACTTCAGTGAAACAGACACAGTTGATATCAAGCAGG
ATCAACCTCGTCCAGCTCACCCAGCCCAATGTGAACCAAGCAGCAGTAGGTGGCAGTGTTGGCACGGCAAACTCCATCTA
CTTGCCACTACCACAAGCAGATGATCAATACACACCCTATTTGTTTATAATTTTCAAGGGGATAGGGTGTCAACCACCG
AAACTGGGGTATTTTGTCTGGCAGCCATACCAGCTGGCTACAGTAGTAGGTATAATAATCAGATTACCACTCCATCA
ATTGGCTACAGGAATGCTAGTGGTACAGGAACATCATTCCTACTAGATGCTGCATCATGGTGGAATATATTGGATGTAAC
TCAGACTGGAGTGCTCTTTGGACAACCAAGATTGGGTGTTGGTGTTATGCAGACAATGAAGACTCTTAAACAGCATATCA
AGGATTACACAGAGCCTGCAATACAGAAATATTATCCTGGAACAACCAACCTTGATGAGCAGTTGAAACAGAGATTGAAC
CTGGCAGAGGGTGACCCGGTCATCTCAATGGGGGACACAACCGGTAGGAGGGCTGCACTCTTTTATAGGACTAGTGATGA
AAAATATATTTTATTTTTCTCAACCACAGAAGATCCAGGTGCACAGTATCAAAATTTGAAAATGCTGTACTTTTGGAACT
GGTCCTACTCTGACACTAAACAGCAATTTTTGGACCACCTTAGAACAGTGCAGTTCGCAAATTTGGATGACAGCCAGCTA
GCCCCCTATGATAGTGATGATGATGACCTTTCTGATGTAACATCACTTTTTGAGCAGGCTGATTTGGGGGATGAGACAGA
TTTCAAATTTAACATGTCCATCCAAACCTCCAAACATCTTGAGGAGGAGAAAAATTACTGGAAGAACCAGTGTGAGAGGA
TGATGATGGAGAAGGCCCTTTCGGGCACCTCACAGCCTCTTGTCCGGTTTGAGAAAGCTGGACCTAGGGCAGATCAATCT
TCTGCCAGTGGTCATTCTTGAG

FIG. 2B3

SEQIDNO:14
>CA_ORF2.seq
ATGGCGGCAATGGCCGACAAGGTCGTTGTCAAGAAGACAACTACAAGGCGCAGGGGCAGGAGTAATTCCCGTTCCCGCAG
CAGGAGTAGGAGCAGGAGCAGAACCAGGATTAAAAAGACAGTCAAAATTGTTGAGAAAAAGCCAGAAAAATCCATCCTAA
AAAAAATTGATCAGGCTGAAAGAAGAGATGAAAGACAGCTCAGGCGGATCCGTAAGAAAGTGCCAGGGCCGCCAGTAAAT
TCCAGGATGACAACAGTAGTCACACTTGGTCAGATAACAGGCAATAAAGACAACACCTTAGAGCGGAAACACAAGTGCTT
TCTGAATCCGCTGTTGATGAAGAGTCAGGAAACTGGTCAAACTGCAACACCCTTATCTGTTAGGGCATCCCAATATAATC
TGTGGAACTATCCAGGACTCCATGTCAGACTTATACCCCTTGCAGGAAAAGCGAATATTCTGGGGTCAGTGGTGTTTTTA
GACCTTGAACAGGAGGCAAATACAGCAGGACCCAGAATCAGTAGACACCATCAAAGCAAGACCCCATGTTGAAGTTCCCAT
AGGGTCGAAAACCGTTTGGAAAGTGCACCCTAGAAGTGCTCTAGGACCTAGACAGGGGTGGTGGAATGTTGACCCTGGTG
ACAGCCCAACTGATTCTCTTGGGCCAGCACTCAACATGTGGACCTACCTGCAAACTGTCAATGCACTCCAGAGCGCTGGG
GGCAACCAAACGCCTTACACCAGTGCACTTTTcCTTGTGGAGGTCTTGGTTACTTATGAGTTTTCAAACTATGGTCCAAA
GCCTGCACTGTCTCAAATGGTATCAGATAGTTTTCCACCATCCTCCGGTTCTACTGCAACCCTAAAAAACACCAGTGATG
GGGCTGTAGCAATACAACTCTCAGGCGCTATCGCCCGAAAGATGGAGGAGGTTGAGCCCAAGGTTAGGCGCTCAAATGCG
CAAACATCAGGTGTCGGTGAAGTGTTCTGGGCAGTGTCCACTGAAGTAGTCAATACAGTAGCAGATGCCATACCAGGCTG
GGGCTGGCTCCTGAAGGGTGGCTGGTTTGTCCTCAGGAAAATCTTTGGGGCCGCGAATGACCAGAATGGCACTTACTTGA
TATACTCTTCAGTGGCAGATGCACAAGGTGACAACAGGATATACACATCAGTGAAACAGACACAGTTGACATCAAGCAGG
ATCAACCTCGTCCAACTCACCCAGCCCAATGTGAACCAAGCAGCAGTAGGTGGCAGTGTTGGTGCGGCAAACTCTATATA
TTTGCCACTACCACAAGCAGATGACCAATATACACCCTAcTTTGTCTATAATTTTCAAGGGGAAAGGGTGTCAACCACCG
AGACTGGGGTATTTTGTTTGGCAGCCATACCAGCTGCGACTACATCCAGTAGGTATAATAATCAGATCACCACTCCATCA ATAGGCTACAGGAATGCTAGTGGTACAGGAACATCATTCCTACTAGATGCTGCATCATGGTGGAATATATTGGATGTAAC
TCAGACTGGAGTGCTCTTTGGACAACCAAGATTGGGTGTTGGTGTTATGCAGACAATGAAGACTCTCAAACAGCATATCA
AGGATTACACAGAGCCTGCAATACAGAAATATTATCCTGGAACAACCAACCTTGATGAGCAGTTGAAACAGAGAYTGAAC CTGGCAGAGGGTGACCCGGTCATCTCAATGGGGGACACAACCGGTAGGAGGGCTGCACTCTTTTATAGGACTAGTGATGA
GAAATACATTTTATTTTTCTCAACCACAGAAGATCCAGGGGCACAGTATCAAAATCTGAAAATGTTGTACTTTTGGAACT
GGTCCTATTCTGACACGAAACAGCAATTTTTGGACCACCTTAGAACAGTGCAGTTTGCAAATTTGGATGACAGCCATCCA
GCCCCTATGATAGTGATGATGATGACCTTTCTGATGTAACATCACTTTTTGAGCAGGCTGATTTGGGGGATGAGACAGA
CTTCAAATTTAATATGTCCATCCAAACCTCCAAACATCTTGAGGAGGAGAAAAATTACTGGAAAAACCAGTGTGAGAGGA
TGATGATGGAGAAGGCCCTTTCGGGCACCTCACAGCCTCTTGTCCGGTTTGAGAAAGCTGGACCTAGGGCAGACCAATCT
TCTGCCAGTGGTCATTCTTGAA

FIG. 2B4

```
                   1                                                    50
TAstV2_2.seq       .........A TGGCGGCGAT GGCCGACAAG GTCGTTGTCA AGAAGACAAC
  CA_ORF2.seq      .........A TGGCGGCAAT GGCCGACAAG GTCGTTGTCA AGAAGACAAC
  PA_ORF2.seq      .......... ........AT GGCCGATAAG GTCGTTGTCA AGAAGACAAC
  MI_ORF2.seq      .........A TGGCGGCAAT GGCCGACAAG GTCGTTGTTA AGAAGACAAC
  TX_ORF2.seq      .........A TGGCGGCGAT GGCCGACAAG GTCGTTGTCA AGAAGACAAC
  MN_ORF2.seq      ATGCTCTCCA CAGCAATAAC GGCACACAAA CACCTTACAC CAGTGCACTT
    Consensus      .........a tggcggcaAt GGCcgAcAAg gtCgTTgtca agaaGacaac 51                                                  100
TAstV2_2.seq       TACAAGGCGC AGG.....GG CA....GGAG TAAT...... ....TCCCGC
  CA_ORF2.seq      TACAAGGCGC AGG.....GG CA....GGAG TAAT...... ....TCCCGT
  PA_ORF2.seq      TACAAGGCGC AGG.....GG CA....GGAG TAAT...... ....TCCCGC
  MI_ORF2.seq      TACAAGGCGC AGG.....GG CA....GGAG TATT...... ....TCCCGC
  TX_ORF2.seq      TACAAGGCGC AGG.....GG CA....GGAG TAAT...... ....TCCCGC
  MN_ORF2.seq      TTCATTGTGC AGGTCTTGGT CACATATGAG TTTTCAATCT ATGGTCCCAA
    Consensus      TaCAagGcGC AGG.....Gg CA....gGAG TaaT...... ....TCCCgc 101                                                 150
TAstV2_2.seq       TCCCGTA... ....GCAGGA GTAGGAGCAG GAGCAGAAC. ..........
  CA_ORF2.seq      TCCCGCA... ....GCAGGA GTAGGAGCAG GAGCAGAACC AG.....GAT
  PA_ORF2.seq      TCCCGTA... ....GCAGGA GTAGGAGCAG GAGCAGAAAT AG.....GGT
  MI_ORF2.seq      TCCCGTA... ....GCAGGA GTAGGAGCAG GAGCAGAACT AG.....GAT
  TX_ORF2.seq      TCCCGTA... ....GCAGGA GTAGGAGCAG GAGCAGAAC. ..........
  MN_ORF2.seq      ACCTGCACTG TCCCACGATG ATTTGGGATA GCTTTCCACC AGCTGCTGGT
    Consensus      tCCcgtA... ....gCagga gTagGaGcag GagcagaAc. ag.....g.t 151                                                 200
TAstV2_2.seq       TAAAAAGACA GTCAAA...A TTATTGAGAA AAAGCCAGAA AAATCCATCC
  CA_ORF2.seq      TAAAAAGACA GTCAAA...A TTGTTGAGAA AAAGCCAGAA AAATCCATCC
  PA_ORF2.seq      TAGAAAGACA GTCAAA...A TTGTTGAGAA AAAGCCAGAA AAATCCATTT
  MI_ORF2.seq      TAAAAAGACA GTCAAG...A TTGTTGAGAA AAAGCCAGAA AAATCCATCT
  TX_ORF2.seq      TAAAAAGACA GTCAAA...A TTATTGAGAA AAAGCCAGAA AAATCCATCC
  MN_ORF2.seq      TCAGAAGCAA CTCTAAGGAA CACCAGTGAT TGGGTTGTTG CAGTGCAGCT
    Consensus      TaaaAAGacA gTCaAa...A tt.ttGaGAa aaaGccagaa aAaTcCAtct 201                                                 250
TAstV2_2.seq       TAAAGAAA.. ATTGATC..A GGCTGAAAGA AGAGATGCAA AACAGCTTAG
  CA_ORF2.seq      TAAAAAAA.. ATTGATC..A GGCTGAAAGA AGAGATGAAA GACAGCTCAG
  PA_ORF2.seq      TGAAGAAA.. ATTGACC..A GGCTGAAAGA AGAGATGAAA AACAAATCAG
  MI_ORF2.seq      TAAAGAAA.. ATTGATC..A GGCTGAAAGG AGAGATGAAA AGCAGATTAG
  TX_ORF2.seq      TAAAGAAA.. ATTGACC..A GGCTGAAAGA AGAGATGAAA AGCAAATTAG
  MN_ORF2.seq      TTCGGGTGGT ATCGCCCGTA GGATGGAGGA AGTGTTGAAC CTAAGAGCAG
    Consensus      Taaagaaa.. ATtGacC..A GGcTGaAaGa AGaGaTGAaa a.cAgatcAG
```

FIG. 2C1

```
              251                                                    300
TAstV2_2.seq  GCGGA.TTCG TAAGAAAGTG CAGGGACCGC CAGTAAATTC CAGGA.....
 CA_ORF2.seq  GCGGA.TCCG TAAGAAAGTG CCAGGGCCGC CAGTAAATTC CAGGA.....
 PA_ORF2.seq  GCGAA.TGCG GAAAAAATTG CAAGGACCAC CAGTGAATTC CAGGA.....
 MI_ORF2.seq  GCGGA.TTCG CAAGAAAATG CAGGGACCGC CAGTGAATTC TAGGA.....
 TX_ORF2.seq  GCGAA.TGCG GAAAAAATTG CAGGGGCCAC CAGTAAATTC CAGGA.....
 MN_ORF2.seq  GCGGTCTAAT GCACAGACAT CAGGTGTTGG AAAAGTGTTT TGGGCAGTGT
    Consensus GCGga.T.cg gaA.AaA.tg CagGggccgc cAgtgaaTTc caGGa.....

301                                                    350
TAstV2_2.seq  .TGACAACAG TAGT.CACAC TTGGTCAGAT AACAGGCAA. ..TAAAGACA
 CA_ORF2.seq  .TGACAACAG TAGT.CACAC TTGGTCAGAT AACAGGCAA. ..TAAAGACA
 PA_ORF2.seq  .TGACAACAG TGGT.CACAC TTGGTCAGAT AACAGGTAA. ..CAAAGACA
 MI_ORF2.seq  .TGACAACAG TAGT.CACAC TTGGTCAGAT AACAGGCAA. ..TAAAGACA
 TX_ORF2.seq  .TGACAACAG TAGT.CACAC TTGGTCAGAT AACAGGCAA. ..TAAAGACA
 MN_ORF2.seq  CTGACTGATG TAGTTAACAC AGTAGCAGAT GATATACCAG GGTGGGGTTG
    Consensus .TGACaacaG TaGT.cACAC ttggtCAGAT aAcAggcaA. ..taaaGaca 351                                                    400
TAstV2_2.seq  ACA.CCCTAG AGCGGAAACA CAAGTGCTTT CTGAA..... TCCGCTGTTG
 CA_ORF2.seq  ACA.CCTTAG AGCGGAAACA CAAGTGCTTT CTGAA..... TCCGCTGTTG
 PA_ORF2.seq  ACA.CCCTAG AGCGGAAACA TAAGTGCTTT CTGAA..... TCCGCTGTTG
 MI_ORF2.seq  ACA.CCTTAG AGCGGAAACA TAAGTGCTTT CTGAA..... TCCGCTGCTG
 TX_ORF2.seq  ACA.CCTTAG AGCGGAAACA CAAGGTTTTT CTGAA..... TCCACTGTTG
 MN_ORF2.seq  GCTTCCTGAA AGGTGGTTGG TTTGTGCCTT AGGTAAGATT TCCGCTGGTT
    Consensus aCa.CCttAg AGcgGaaaca taaGtgctTT ctGaA..... TCCgCTGtTg 401                                                    450
TAstV2_2.seq  ATGAAGAGTC AGGAAACTGG TCAAACTGC. AACACCCTTA TCTGTTAGGG
 CA_ORF2.seq  ATGAAGAGTC AGGAAACTGG TCAAACTGC. AACACCCTTA TCTGTTAGGG
 PA_ORF2.seq  ATGAAGAGTC AGGAAACCGG TCAAACTGC. AACCCCCTTA TCTGTTAGGG
 MI_ORF2.seq  ATGAAGAGTC AGGAAACTGG TCAAACTGC. AACACCCTTA TCTGTTAGGG
 TX_ORF2.seq  ATGAAGAGTC AGGAAACTGG TCAAACTGC. AACACCCTTG TCTGTTAGAG
 MN_ORF2.seq  ATGAAGAGTC AGGAGACCGG CCAAACTGCG AACACCATTG TCAGTTAGGG
    Consensus ATGAAGAGTC AGGAaACtGG tCAAACTGC. AACaCCcTTa TCtGTTAGgG 451                                                    500
TAstV2_2.seq  CATCCCAATA TAAT.CTGTG GAAGCTATCC AG.ACTCCAT GTCAGACTTA
 CA_ORF2.seq  CATCCCAATA TAAT.CTGTG GAA.CTATCC AGGACTCCAT GTCAGACTTA
 PA_ORF2.seq  CATCCCAATA TAAT.CTGTG GAAGCTATCC AG.ACTCCAT GTCAGACTTA
 MI_ORF2.seq  CATCCCAATA TAAT.CTGTG GAAGCTATCC AG.ACTCCAT GTCAGACTTA
 TX_ORF2.seq  CATCCCAATA CAAT.CTGTG GAAGCTATCC AG.ACTCCAT GTCAGACTTA
 MN_ORF2.seq  CATCTCAGTA TAATTCTGTG GAAGTTGTCC AG.ACTCCAT GTTAGGCTGA
    Consensus CATCcCAaTA tAAT.CTGTG GAAgcTaTCC AG.ACTCCAT GTcAGaCTtA 501                                                    550
TAstV2_2.seq  TACCCCTTGC AGGAAAAGCG AATATTTTGG GGTCAGTGGT GTTCTTAGAT
 CA_ORF2.seq  TACCCCTTGC AGGAAAAGCG AATATTCTGG GGTCAGTGGT GTTTTTAGAC
 PA_ORF2.seq  TACCCCTTGC AGGAAAAGCG AATATTTTGG GGTCAGTGGT TTTTCTAGAT
 MI_ORF2.seq  TACCCCTTGC AGGAAAAGCA AATATTTTGG GGTCAGTGGT GTTCCTAGAT
 TX_ORF2.seq  TACCCCTTGC AGGAAAAGCG AATATTCTGG GGTCAGTGGT GTTTCTAGAT
 MN_ORF2.seq  TACCCCTTGC AGGAAAAGCA AACATCTTGG GATCAGTGGT GTTCTTAGAT
    Consensus TACCCCTTGC AGGAAAAGCg AAtATttTGG GgTCAGTGGT gTTctTAGAt
```

FIG. 2C2

```
              551                                                    600
TAstV2_2.seq  CTTGAACAGG AGGCAAACAC AGCAGGACCA GAATCAGTAG ATACCATCAA
  CA_ORF2.seq CTTGAACAGG AGGCAAATAC AGCAGGACCA GAATCAGTAG ACACCATCAA
  PA_ORF2.seq CTTGAGCAGG AGGCAAATAC AGCAGGACCA GAATCAGTAG ATACCATCAA
  MI_ORF2.seq CTTGAACAGG AGGCAAACAC AGCAGGACCA GAATCAGTAG ATACCATCAA
  TX_ORF2.seq CTTGAACAAG AGGCAAATAC AGCAGGACCA GAATCAGTAG ATACCATCAA
  MN_ORF2.seq CTAGAGCAGG AGTACGTGGC AGCGGGACCA GAGTCTGTGG ATACCATCAA
    Consensus CTtGAaCAgG AGgcaaa.aC AGCaGGACCA GAaTCaGTaG AtACCATCAA 601                                                    650
TAstV2_2.seq  GGCAAGACCC CATGTTGAAG TTCCCATAGG GTCGAAAACC GTTTGGAAAG
  CA_ORF2.seq AGCAAGACCC CATGTTGAAG TTCCCATAGG GTCGAAAACC GTTTGGAAAG
  PA_ORF2.seq AGCAAGACCC CATGTTGAAG TTCCCATAGG GTCAAAAACC GTCTGGAAAG
  MI_ORF2.seq AGCAAGACCC CATGTTGAAG TTCCCATAGG GTCAAAAACT GTTTGGAAAG
  TX_ORF2.seq AGCAAGACCC CATGTTGAAG TTCCCATAGG GTCGAAAACT GTTTGGAAAG
  MN_ORF2.seq AGCAAGACCC CATGTTGAAG TTCCTATTGG GGCGAAAACT GTCTGGAAAG
    Consensus aGCAAGACCC CATGTTGAAG TTCCcATaGG GtCgAAAACt GTtTGGAAAG 651                                                    700
TAstV2_2.seq  TGCACCCTAG AAGCGCTCTA GGACCTAGAC AGGGGTGGTG GAATGTTGAC
  CA_ORF2.seq TGCACCCTAG AAGTGCTCTA GGACCTAGAC AGGGGTGGTG GAATGTTGAC
  PA_ORF2.seq TGCACCCTAG AAGTGCTCTA GGACCTAGAC AGGGGTGGTG GAATGTTGAT
  MI_ORF2.seq TGCACCCTAG AAGTGCTCTA GGACCTAGAC AGGGGTGGTG GAATGTTGAT
  TX_ORF2.seq TGCACCCTAG AAGTGCTCTG GGGCCTAGAC AGGGGTGGTG GAATGTTGAC
  MN_ORF2.seq TGCACCCTAG AAGTGCCTTA GGTCCAGAC AAGGGTGGTG GAATGTTGAC
    Consensus TGCACCCTAG AAGtGCtcTa GGaCCtAGAC AgGGGTGGTG GAATGTTGAc 701                                                    750
TAstV2_2.seq  CCTGGTGACA GCCCAACTGA TTCTCTTGGG CCAGCACTCA ACATGTGGAC
  CA_ORF2.seq CCTGGTGACA GCCCAACTGA TTCTCTTGGG CCAGCACTCA ACATGTGGAC
  PA_ORF2.seq CCTGGTGACA GCCCAACTGA TTCTCTTGGG CCAGCACTCA ACATGTGGAC
  MI_ORF2.seq CCCGGTGACA GCCCAACTGA TTCTCTTGGG CCAGCACTCA ATATGTGGAC
  TX_ORF2.seq CCTGGTGACA GCCCAACTGA TTCCCTTGGG CCAGCACTCA ACATGTGGAC
  MN_ORF2.seq CCTGGTGATA GTCCAACTGA TTCTCTTGGA CCGGCACTTA ACATGTGGAC
    Consensus CCtGGTGAcA GcCCAACTGA TTCtCTTGGg CCaGCACTcA AcATGTGGAC 751                                                    800
TAstV2_2.seq  CTACCTGCAA ACTGTCAATG CACTCCAGAG CGCTGGGGGC ACTCAAACGC
  CA_ORF2.seq CTACCTGCAA ACTGTCAATG CACTCCAGAG CGCTGGGGGC AACCAAACGC
  PA_ORF2.seq CTACCTGCAA ACTGTCAATG CACTCCAGAG CGCCACTGGT ACACAAACAC
  MI_ORF2.seq CTACCTGCAA ACTGTCAATG CACTCCAGAG CACCAGTGGT ACACAAACAC
  TX_ORF2.seq CTACCTGCAA ACTGTTAATG CACTCCAGAG CGCTGGGGGC AACCAAACAC
  MN_ORF2.seq TTATTTGCAA ACTGTCAATG CACTCCACAG CAATAACGGC ACACAAACAC
    Consensus cTAccTGCAA ACTGTcAATG CACTCCAgAG Cgctag.GGc AcaCAAACaC 801                                                    850
TAstV2_2.seq  CTTACACCAG TGCACTTTTT CTTGTGGAGG TCTTGGTCAC TTATGAGTTT
  CA_ORF2.seq CTTACACCAG TGCACTTTTC CTTGTGGAGG TCTTGGTTAC TTATGAGTTT
  PA_ORF2.seq CGTACACCAG TGCACTTTTC CTTGTGGAGG TCTTGGTTAC GTATGAGTTT
  MI_ORF2.seq CTTATACCAG TGCACTTTTC CTTGTGGAGG TTTTGGTTAC TTATGAGTTT
  TX_ORF2.seq CTTACACCAG TGCACTTTTC CTTGTGGAGG TCTTGGTTAC CTATGAGTTT
  MN_ORF2.seq CTTACACCAG TGCACTTTTC CTTGTGGAGG TCTTGGTCAC ATATGAGTTT
    Consensus CtTAcACCAG TGCACTTTTc CTTGTGGAGG TcTTGGTtAC .TATGAGTTT
```

FIG. 2C3

```
              851                                                      900
TAstV2_2.seq  TCAAACTATG GCCCAAAGCC TGCACTGTCT CAAATGGTAT CAGACAGCTT
  CA_ORF2.seq TCAAACTATG GTCCAAAGCC TGCACTGTCT CAAATGGTAT CAGATAGTTT
  PA_ORF2.seq TCAAATTATG GTCCAAAGCC CGCACTGTCC CAGATGGTAT CAGACAGCTT
  MI_ORF2.seq TCAAATTATG GTCCAAAGCC CGCACTGTCC CAGATGGTAT CAGACAGCTT
  TX_ORF2.seq TCAAATTATG GTCCAAAGCC TGCACTGTCC CAAATGATAT CGGACAGTTT
  MN_ORF2.seq TCAAACTATG GTCCCAAACC TGCACTGTCC CAGATGATTT CGGATAGCTT
    Consensus TCAAAcTATG GtCCaAAgCC tGCACTGTCc CAgATGgTaT CaGAcAGcTT 901                                                      950
TAstV2_2.seq  TCCACCAGCC TCCGGTTCTA CTGCAACCTT AAAAAACACC AGTGATGGGG
  CA_ORF2.seq TCCACCATCC TCCGGTTCTA CTGCAACCCT AAAAAACACC AGTGATGGGG
  PA_ORF2.seq TCCACCAGCT TCCGGCTCTA CTGCAACCTT AAAAAACACC AGTGATGGGG
  MI_ORF2.seq TCCACCAGCT TCCGGCTCTA CTGCAACCTT AAAAAACACC AGTGATGGGG
  TX_ORF2.seq TCCACCAGCC TCCGGTTCTA CTGCAACTCT TAAAAACACC AGTGATGGGG
  MN_ORF2.seq TCCACCAGCT GCTGGTTCAA CTGCAACTCT AAAAAACACC AGTGATGGGG
    Consensus TCCACCAgCt tCcGGtTCtA CTGCAACccT aAAAAACACC AGTGATGGGG 951                                                     1000
TAstV2_2.seq  CTGTAGCAAT ACAACTCTCA GGCGCTATCG CCCGAAAGAT GGAGGAGGTT
  CA_ORF2.seq CTGTAGCAAT ACAACTCTCA GGCGCTATCG CCCGAAAGAT GGAGGAGGTT
  PA_ORF2.seq CTGTAGCAAT ACAACTCTCA GGCGCTATTG CCCGAAAGAT GGAGGAGGTT
  MI_ORF2.seq CTGTAGCAAT ACAACTCTCA GGCGCTATTG CCCGAAAGAT GGAGGAGGTT
  TX_ORF2.seq CTGTAGCAAT ACAACTTTCA GGCGCTATCG CCCGAAAAAT GGAGGAGCTT
  MN_ORF2.seq CTGTTGCAGT GCAGCTTTCG GGTGCTATCG CCCGTAGGAT GGAGGAGGTT
    Consensus CTGTaGCAaT aCAaCTcTCa GGcGCTATcG CCCGaAagAT GGAGGAGgTT 1001                                                    1050
TAstV2_2.seq  GAGCCCAAGG GTAGGCGCTC AAATGCGCAA ACATCAGGTG TCGGTGAAGT
  CA_ORF2.seq GAGCCCAAGG TTAGGCGCTC AAATGCGCAA ACATCAGGTG TCGGTGAAGT
  PA_ORF2.seq GAGCCCAAGG GTAGGCGCTC AAATGCGCAA ACATCAGGTG TCGGTGAAGT
  MI_ORF2.seq GAGCCCAAGG GTAGGCGCTC AAATGCGCAA ACATCAGGTG TCGGTGAAGT
  TX_ORF2.seq GAGCCTAAGG GTAGATGCTC AAATGCACAG ACATCAGGTG TTGGAGAAGT
  MN_ORF2.seq GAACCTAAGA GCAGGCGGTC AAATGCACAG ACATCAGGTG TTGGAGAAGT
    Consensus GAgCCcAAGg gtAGgcGcTC AAATGCgCAa ACATCAGGTG TcGGtGAAGT 1051                                                    1100
TAstV2_2.seq  GTTCTGGGCA GTGTCCACTG AAGTAGTCAA TACAGTAGCA GATGCCATAC
  CA_ORF2.seq GTTCTGGGCA GTGTCCACTG AAGTAGTCAA TACAGTAGCA GATGCCATAC
  PA_ORF2.seq GTTCTGGGCA GTGTCCACTG AAGTGGTCAA CACAGTAGCA GATGCCATAC
  MI_ORF2.seq GTTCTGGGCA GTGTCCACTG AAGTAGTCAA TACAGTAGCA GATGCCATAC
  TX_ORF2.seq GTTTTGGGCA GTGTCAACTG AGGTGGTTAA CACAGTAGCA GATGCTATAC
  MN_ORF2.seq GTTTTGGGCA GTGTCAACTG ATGTAGTTAA CACAGTAGCA GATGCTATAC
    Consensus GTTcTGGGCA GTGTCcACTG AaGTaGTcAA cACAGTAGCA GATGCcATAC 1101                                                    1150
TAstV2_2.seq  CAGGCTGGGG CTGGCTCCTG AAAGGTGGCT GGTTTGTCCT TAGGAAAATC
  CA_ORF2.seq CAGGCTGGGG CTGGCTCCTG AAGGGTGGCT GGTTTGTCCT CAGGAAAATC
  PA_ORF2.seq CAGGCTGGGG CTGGCTCCTG AAAGGTGGCT GGTTTGTCCT CAGGAAAATC
  MI_ORF2.seq CAGGCTGGGG CTGGCTCCTG AAAGGTGGCT GGTTTGTCCT CAGGAAAATT
  TX_ORF2.seq CAGGTTGGGG TTGGCTCTTG AAAGGTGGCT GGTTTGTCCT TAGAAAATTA
  MN_ORF2.seq CAGGCTGGGG TTGGCTCCTG AAAGGTGGCT GGTTCGTCCT TAGGAAGATA
    Consensus CAGGcTGGGG cTGGCTCcTG AAaGGTGGCT GGTTtGTCCT tAGgAAaaT.
```

FIG. 2C4

|              | 1151       |            |            |            | 1200       |
|---|---|---|---|---|---|
| TAstV2_2.seq | TTTGGGGCCG | CAAATGACCA | GAATGGCACT | TACTTGATAT | ACTCTTCAGT |
| CA_ORF2.seq  | TTTGGGGCCG | CGAATGACCA | GAATGGCACT | TACTTGATAT | ACTCTTCAGT |
| PA_ORF2.seq  | TTTGGGGCCG | CGAATGACCA | GAATGGCACT | TACTTGATAT | ACTCTTCAGT |
| MI_ORF2.seq  | TTTGGGGCCG | CGAATGACCA | GAATGGCACT | TACTTGATAT | ACTCTTCAGT |
| TX_ORF2.seq  | TTTGGAGCTG | CGAATGACGC | AAATGGCACC | TACCTGTTAT | ATTCATCGGT |
| MN_ORF2.seq  | TTTGGAGCTG | CGAATGACGC | AAATAGCACC | TACCTGTTGT | ATTCATCGGT |
| Consensus    | TTTGGgGCcG | CgAATGACca | gAATgGCACt | TACttGaTaT | AcTCtTCaGT |

|              | 1201       |            |            |            | 1250       |
|---|---|---|---|---|---|
| TAstV2_2.seq | GGCAGATGCA | CAAGGTGACA | ACAGGATATA | CACATCAGTG | AAACAGACAC |
| CA_ORF2.seq  | GGCAGATGCA | CAAGGTGACA | ACAGGATATA | CACATCAGTG | AAACAGACAC |
| PA_ORF2.seq  | GGCAGATGCA | CAAGGTGACA | ACAGGATATA | CACATCAGTG | AAACAGACAC |
| MI_ORF2.seq  | GGCAGATGCA | CAAGGTGACA | ACAGGATATA | CACTTCAGTG | AAACAGACAC |
| TX_ORF2.seq  | GGCCGATGCA | CAGCAGGATA | ACAGATTATA | TACAAAAGTG | AAACAAGGAC |
| MN_ORF2.seq  | AGCTGATGCA | CAGCAAGACA | ACAGAATATA | TACAACAATA | AAACAAGGAC |
| Consensus    | gGCaGATGCA | CAaggtGAcA | ACAGgaTATA | cACatcAgTg | AAACAgacAC |

|              | 1251       |            |            |            | 1300       |
|---|---|---|---|---|---|
| TAstV2_2.seq | AG......TT | GACATCAAGC | AGGATCAACC | TCGTCCAACT | CACCCAGCCC |
| CA_ORF2.seq  | AG......TT | GACATCAAGC | AGGATCAACC | TCGTCCAACT | CACCCAGCCC |
| PA_ORF2.seq  | AG......TT | GACATCAAGC | AGGATCAACC | TCGTCCAACT | CACCCAGCCC |
| MI_ORF2.seq  | AG......TT | GATATCAAGC | AGGATCAACC | TCGTCCAGCT | CACCCAGCCC |
| TX_ORF2.seq  | AA......TT | AACATCGAGT | GTGATCAACC | TCGTCCAACT | CACTCAGCCC |
| MN_ORF2.seq  | AAGGACAACT | AACATCAAGT | GTGATCAATC | TGGTTCAACT | CACCCAGCCA |
| Consensus    | Ag......tT | gAcATCaAGc | agGATCAAcC | TcGTcCAacT | CACcCAGCCc |

|              | 1301       |            |            |            | 1350       |
|---|---|---|---|---|---|
| TAstV2_2.seq | AATGTGAACC | AAGCAGCAGT | AGGTGGCAGT | GTTGGTGCGG | CAAACTCCAT |
| CA_ORF2.seq  | AATGTGAACC | AAGCAGCAGT | AGGTGGCAGT | GTTGGTGCGG | CAAACTCTAT |
| PA_ORF2.seq  | AATGTGAACC | AAGCAGCAGT | AGGTGGCAGT | GTTGGTGCGG | CAAACTCCAT |
| MI_ORF2.seq  | AATGTGAACC | AAGCAGCAGT | AGGTGGCAGT | GTTGGCACGG | CAAACTCCAT |
| TX_ORF2.seq  | AATGTGAACC | AAGCAGCAGT | AGGTGGCAGT | GTTGGCTCGG | CAAATTCCAT |
| MN_ORF2.seq  | AATGTAAATC | AAGCAGCTGT | TGGTGGTAGT | GTTGGTTCTG | CAAATTCCAT |
| Consensus    | AATGTgAAcC | AAGCAGCaGT | aGGTGGcAGT | GTTGGt.CgG | CAAAcTCcAT |

|              | 1351       |            |            |            | 1400       |
|---|---|---|---|---|---|
| TAstV2_2.seq | CTATTTGCCA | CTACCACAAG | CAGATGACCA | ATACACACCC | TACTTTGTCT |
| CA_ORF2.seq  | ATATTTGCCA | CTACCACAAG | CAGATGACCA | ATATACACCC | TACTTTGTCT |
| PA_ORF2.seq  | CTATTTGCCA | CTGCCACAAG | CAGATGATCA | ATACACACCC | TATTTTGTTT |
| MI_ORF2.seq  | CTACTTGCCA | CTACCACAAG | CAGATGATCA | ATACACACCC | TATTTTGTTT |
| TX_ORF2.seq  | CTATTTGCCA | TTACCACAAG | CAGATGACCA | ATATACACCC | CATCTTGTTT |
| MN_ORF2.seq  | CTACCTACCC | TTGCCACAAG | CAGAGGATCA | ATATACACCG | CACTTTGTTT |
| Consensus    | cTAttTgCCa | cTaCCACAAG | CAGAtGAtCA | ATAtACACCc | tActTTGTtT |

|              | 1401       |            |            |            | 1450       |
|---|---|---|---|---|---|
| TAstV2_2.seq | ATAATTTTCA | AGGGGAAAGG | GTGTCAACCA | CCGAGACTGG | GGTATTTTGT |
| CA_ORF2.seq  | ATAATTTTCA | AGGGGAAAGG | GTGTCAACCA | CCGAGACTGG | GGTATTTTGT |
| PA_ORF2.seq  | ATAATTTTCA | AGGGGAAAGG | GTGTCAACCA | CCGAGACTGG | GGTATTTTGT |
| MI_ORF2.seq  | ATAATTTTCA | AGGGGATAGG | GTGTCAACCA | CCGAAACTGG | GGTATTTTGT |
| TX_ORF2.seq  | ATGATTTCCA | AGGGGAATAGG | GTGTCAACCG | CTGAGACTGG | GGTATTTTGT |
| MN_ORF2.seq  | ATGATTTCCA | GGGAACGAGG | GTGTCAACAA | CAGAGTCTGG | AGTCTTTTGC |
| Consensus    | ATaATTTtCA | aGGgga.AGG | GTGTCAACca | CcGAgaCTGG | gGTaTTTTGt |

FIG. 2C5

```
              1451                                                    1500
TAstV2_2.seq  CTGGCAGCCA TACCAGCTGC GACTACATCT AGTAGGTATA ATAATCAGAT
  CA_ORF2.seq TTGGCAGCCA TACCAGCTGC GACTACATCC AGTAGGTATA ATAATCAGAT
  PA_ORF2.seq CTGGCAGCCA TACCAGCAGC GACTACAACT AGTAGGTATA ATAATCAGAT
  MI_ORF2.seq CTGGCAGCCA TACCAGCTGC GACTACAACT AGTAGGTATA ATAATCAGAT
  TX_ORF2.seq CTGGCATCCA TACCAGCCGC AACTACATCC AGTAGGTACA ATGGTCAAAT
  MN_ORF2.seq CTGTCCTCAA TACCAAGTGC TGACAGTAAG AGCAGATATA ACAACCAGAT
    Consensus cTGgCagCcA TACCAgctGC gactAcaac. AGtAGgTAtA AtaatCAgAT 1501                                                    1550
TAstV2_2.seq  CACCACTCCA TCAATTGGCT ACAGGAATGC TAGTGGTACA GGAACATCAT
  CA_ORF2.seq CACCACTCCA TCAATAGGCT ACAGGAATGC TAGTGGTACA GGAACATCAT
  PA_ORF2.seq CACCACTCCA TCAATTGGCT ACAGGAATGA TAGTGGTACA GGAACATCAT
  MI_ORF2.seq TACCACTCCA TCAATTGGCT ACAGGAATGC TAGTGGTACA GGAACATCAT
  TX_ORF2.seq CACCAGTCCT TCAATTGGCT ATAAGAGTGC TAGTGGCACA GGAACATCTT
  MN_ORF2.seq GAACTCTCCA ACAGTGGGAT ATAAGAATGA AGGTGGTACT GGAACATCAT
    Consensus cAcCacTCCa tCAaTtGGcT AcAgGAaTGc taGTGGtACa GGAACATCaT 1551                                                    1600
TAstV2_2.seq  TCCTACTAGA TGCTGCATCA TGGTGGAATA TATTGGATGT AACTCAGACT
  CA_ORF2.seq TCCTACTAGA TGCTGCATCA TGGTGGAATA TATTGGATGT AACTCAGACT
  PA_ORF2.seq TCCTACTAGA TGCTGCATCA TGGTGGAATA TATTGGATGT AACTCAAACT
  MI_ORF2.seq TCCTACTAGA TGCTGCATCA TGGTGGAATA TATTGGATGT AACTCAGACT
  TX_ORF2.seq TCTCACTAGA TGAAGCATCA TGGTGGAACA TCTTGGATGT AACTCAGACT
  MN_ORF2.seq TCGCTATGGA CAATGCCCCG TGGTGGAGCA TCCTGGATGT TACTCAAACA
    Consensus TCctacTaGA tgctGCatCa TGGTGGAatA TatTGGATGT aACTCAgACt 1601                                                    1650
TAstV2_2.seq  GGAGTGCTTT TTGGACAACC AAGATTGGGT GTTGGTGTCA TGCAGACAAT
  CA_ORF2.seq GGAGTGCTCT TTGGACAACC AAGATTGGGT GTTGGTGTTA TGCAGACAAT
  PA_ORF2.seq GGAGTGCTCT TTGGACAACC AAGATTGGGT GTTGGTGTCA TGCAGACAAT
  MI_ORF2.seq GGAGTGCTCT TTGGACAACC AAGATTGGGT GTTGGTGTTA TGCAGACAAT
  TX_ORF2.seq GGGGTCCTCT TTGGACAACC AAAATTGGGC ATTGGTGTCA TGCAAACAAT
  MN_ORF2.seq GGTGTCATCT TTGGCCAGCC CAGGTTAGGT GTTGGGGTTA TACAAACAAT
    Consensus GGaGTgCTcT TTGGaCAaCC aAgaTTgGGt gTTGGtGTtA TgCAgACAAT 1651                                                    1700
TAstV2_2.seq  GAAGACTCTC AAACAGCATA TCAAGGATTA CACAGAGCCT GCAATACAGA
  CA_ORF2.seq GAAGACTCTC AAACAGCATA TCAAGGATTA CACAGAGCCT GCAATACAGA
  PA_ORF2.seq GAAGACTCTT AAACAGCATA TCAAGGATTA TACAGAGCCT GCAATACAGA
  MI_ORF2.seq GAAGACTCTT AAACAGCATA TCAAGGATTA CACAGAGCCT GCAATACAGA
  TX_ORF2.seq GAAGACCCTT AAACAACACA TCAGGGATTA TACAGAGCCT GCAATAAAAA
  MN_ORF2.seq GAAAACACTG AAACAACACA TTACAGATTT TACTGAACCT GCAGTAAAGA
    Consensus GAAgACtCT. AAACAgCATA TcAagGATTa tACaGAgCCT GCAaTAcAgA 1701                                                    1750
TAstV2_2.seq  AATATTATCC TGGAACAACT AACCTTGATG AGCAGTTGAA GCAGAGATTG
  CA_ORF2.seq AATATTATCC TGGAACAACC AACCTTGATG AGCAGTTGAA ACAGAGAYTG
  PA_ORF2.seq AATATTATCC TGGAACAACC AACCTTGATG AGCAGTTGAA ACAGAGATTG
  MI_ORF2.seq AATATTATCC TGGAACAACC AACCTTGATG AGCAGTTGAA ACAGAGATTG
  TX_ORF2.seq AATATTACCC TGGAACAACT AACATTGCTG AAGAATTGAA ACAGAGGATG
  MN_ORF2.seq AATATTATCC TGGCACTACC AACTTGGACC AGACACTCAA AGATAGAATG
    Consensus AATATTAtCC TGGaACaACc AACcTtGatg AgcagtTgAA acAgAGa.TG
```

FIG. 2C6

```
              1751                                                    1800
TAstV2_2.seq  AACCTGGCAG AGGGTGACCC GGTCATCTCA ATGGGGGACA CAAACGGTAG
  CA_ORF2.seq AACCTGGCAG AGGGTGACCC GGTCATCTCA ATGGGGGACA CAACCGGTAG
  PA_ORF2.seq AACCTGGCAG AGGGTGACCC GGTCATCTCA ATGGGGGACA CAACCGGTAG
  MI_ORF2.seq AACCTGGCAG AGGGTGACCC GGTCATCTCA ATGGGGGACA CAACCGGTAG
  TX_ORF2.seq AAACTGGCAG AGGGTGATCC GGTCATCTCG ATGGGAGACA CAAATGGTAG
  MN_ORF2.seq AAATTAACAG AAGGAGACCC GGTCGTCTCT ATGGGAGATG TGACAGGGAG
     Consensus AAccTggCAG AgGGtGAcCC GGTCaTCTCa ATGGGgGAca caAccGGtAG 1801                                                    1850
TAstV2_2.seq  GAGGGCTGCA CTCTTTTATA GGACTAGTGA TGAAAAATAT ATTTTATTTT
  CA_ORF2.seq GAGGGCTGCA CTCTTTTATA GGACTAGTGA TGAGAAATAC ATTTTATTTT
  PA_ORF2.seq GAGGGCTGCA CTCTTTTATA GGACTAGTGA TGAAAAATAT ATTTTATTTT
  MI_ORF2.seq GAGGGCTGCA CTCTTTTATA GGACTAGTGA TGAAAAATAT ATTTTATTTT
  TX_ORF2.seq GAGAGCTGCA CTTTTTTATA GGACTAGTGA TGAAAGGTAC ATTTTGTTCT
  MN_ORF2.seq AAGAGCAGCA CTCTTTTATA GAACTAGTGA TGAGAGGTAC ATCTTGCTCA
     Consensus gAGggCtGCA CTcTTTTATA GgACTAGTGA TGAaAaaTAc ATtTTatTtt 1851                                                    1900
TAstV2_2.seq  TCTCAACCAC AGAAGATCCA GGGGCACAGT ATCAAAATCT GAAAATGTTG
  CA_ORF2.seq TCTCAACCAC AGAAGATCCA GGGGCACAGT ATCAAAATCT GAAAATGTTG
  PA_ORF2.seq TCTCAACTAC AGAAGATCCA GGGGCACAGT ATCAAAATCT GAAAATGTTG
  MI_ORF2.seq TCTCAACCAC AGAAGATCCA GGTGCACAGT ATCAAAATTT GAAAATGCTG
  TX_ORF2.seq TTTCAACAAC AGGAGATCCA GGGTCACAAT TTGAAAATTT GAAGATGTTG
  MN_ORF2.seq TTTCATCAAC AGAAGATCCC GGGTCACAAT TTGAGAGGCT GAAGGTGACA
     Consensus TcTCAac.AC AGaAGATCCa GGggCACAgT aTcAaAatcT GAAaaTGttg 1901                                                    1950
TAstV2_2.seq  TACTTCTGGA ACTGGTCCTA TTCTGACACA AAACAGCAAT TTTTGGACCA
  CA_ORF2.seq TACTTTTGGA ACTGGTCCTA TTCTGACACG AAACAGCAAT TTTTGGACCA
  PA_ORF2.seq TACTTTTGGA ACTGGTCCTA TTCTGACACG AAACAGCAAT TTTTGGACCA
  MI_ORF2.seq TACTTTTGGA ACTGGTCCTA CTCTGACACT AAACAGCAAT TTTTGGACCA
  TX_ORF2.seq TACTTTTGGA ACTGGTCCTA TTCTGACAAC AAACAGCAAT TTCTGGACCG
  MN_ORF2.seq ACTTTCTGGA ACTGGTCCCT TTCTGACAAC AAAAGTGAGT TCTTAAATAG
     Consensus tacTTtTGGA ACTGGTCCta tTCTGACAc. AAAcagcAaT TttTggAcca 1951                                                    2000
TAstV2_2.seq  CCTTAGAACA GTGCAGTTTG CAAATTTGGA TGACAGCCAG CCAGCCCCCT
  CA_ORF2.seq CCTTAGAACA GTGCAGTTTG CAAATTTGGA TGACAGCCAT CCAGCCCCCT
  PA_ORF2.seq CCTCAGAACA GTGCAGTTTG CAAATTTGGA TGACAACCAT CCAGCCCCCT
  MI_ORF2.seq CCTTAGAACA GTGCAGTTCG CAAATTTGGA TGACAGCCAG CTAGCCCCCT
  TX_ORF2.seq CCTTAGAACA GTGCAATTTG CAAATGCGGA TGACAGCCAG CCAACCCCTT
  MN_ORF2.seq GTTGAGAACC ATACAGTATG CAAATGCACA TCAAGAAGAA ATGTCTCATT
     Consensus ccTtAGAACa gTgCAgTttG CAAATttggA TgAcagccA. ccagCcCccT 2001                                                    2050
TAstV2_2.seq  ATGATAGTGA TGATGATGAC CTTTCTGATG TAACATCACT TTTTGAGCAG
  CA_ORF2.seq ATGATAGTGA TGATGATGAC CTTTCTGATG TAACATCACT TTTTGAGCAG
  PA_ORF2.seq ATGATAGTGA TGATGATGAC CTTTCTGATG TAACATCACT TTTTGAGCAG
  MI_ORF2.seq ATGATAGTGA TGATGATGAC CTTTCTGATG TAACATCACT TTTTGAGCAG
  TX_ORF2.seq GTGATAGTGA TGATGATGAC CTCTCTGATG TAACATCACT CTTTGAGCAG
  MN_ORF2.seq GTGATAGCGA CGATGATGGG CTGTCAGATG TAACGTCGCT GTTGAACAG
     Consensus aTGATAGtGA tGATGATGac CTtTCtGATG TAACaTCaCT tTTTGAgCAG
```

FIG. 2C7

```
              2051                                                      2100
TAstV2_2.seq  GCTGATTTGG GGGATGAGAC AGACTTCAAA TTTAATATGT CCATCCAAAC
  CA_ORF2.seq GCTGATTTGG GGGATGAGAC AGACTTCAAA TTTAATATGT CCATCCAAAC
  PA_ORF2.seq GCTGATTTGG GGGATGAGAC AGACTTCAAA TTTAATATGT CCATCCAAAC
  MI_ORF2.seq GCTGATTTGG GGGATGAGAC AGATTTCAAA TTTAACATGT CCATCCAAAC
  TX_ORF2.seq GCTGATTTGG GGGATGAGAC AGATTTCAAA TTTAATATGT CCATCCAGAC
  MN_ORF2.seq GCCGACCTGG AGGATGAGAC AGATTTTAAA TTTAAAATGT CTATTCAAAC
    Consensus GCtGAttTGG gGGATGAGAC AGAtTTcAAA TTTAAtATGT CcATcCAaAC 2101                                                      2150
TAstV2_2.seq  CTCCAAACAT CTTGAGGAGG AGAAAAATTA CTGGAAAAAC CAGTGTGAGA
  CA_ORF2.seq CTCCAAACAT CTTGAGGAGG AGAAAAATTA CTGGAAAAAC CAGTGTGAGA
  PA_ORF2.seq CTCCAAACAT CTTGAGGAGG AGAAAAATTA CTGGAAAAAC CAGTGTGAGA
  MI_ORF2.seq CTCCAAACAT CTTGAGGAGG AGAAAAATTA CTGGAAGAAC CAGTGTGAGA
  TX_ORF2.seq CTCCAAACAT CTTGAGGAGG AGAAAAATTA CTGGAAAAAC CAGTGTGAGA
  MN_ORF2.seq CTCTAAAGAT CTTGAGGATG AGAAAAATTA CTGGAAAAAC CAGTGTGAGA
    Consensus CTCcAAAcAT CTTGAGGAgG AGAAAAATTA CTGGAaAAC CAGTGTGAGA 2151                                                      2200
TAstV2_2.seq  GGATGATGAT GGAGAAGGCC CTTTCGGGCA CCTCACAGCC TCTTGTCCGG
  CA_ORF2.seq GGATGATGAT GGAGAAGGCC CTTTCGGGCA CCTCACAGCC TCTTGTCCGG
  PA_ORF2.seq GGATGATGAT GGAGAAGGCC CTTTCGGGCA CCTCACAGCC TCTTGTCCGG
  MI_ORF2.seq GGATGATGAT GGAGAAGGCC CTTTCGGGCA CCTCACAGCC TCTTGTCCGG
  TX_ORF2.seq GGATGATGAT GGAGAAGGCC CTCTCGGGCA CCTCACAACC TCTTGTCCGG
  MN_ORF2.seq GGATGATGAT GGAGAAGGCC CTTTCGGGCA CCTCACAGCC TCTTGTCCGG
    Consensus GGATGATGAT GGAGAAGGCC CTtTCGGGCA CCTCACAgCC TCTTGTCCGG 2201                                                      2250
TAstV2_2.seq  TTTGAGAAAG CTGGACCTAG GGCAGACCAA TCTTCTGCCA GTGGTCATTC
  CA_ORF2.seq TTTGAGAAAG CTGGACCTAG GGCAGACCAA TCTTCTGCCA GTGGTCATTC
  PA_ORF2.seq TTTGAGAAAG CTGGACCTAG GGCAGACCAA TCTTCTGCCA GTGGTCATTC
  MI_ORF2.seq TTTGAGAAAG CTGGACCTAG GGCAGATCAA TCTTCTGCCA GTGGTCATTC
  TX_ORF2.seq TTTGAGAAAG CTGGACTTAG GGCAGACCAA TCTTCTGCCA GTGGTCATTC
  MN_ORF2.seq TTTGAGAAAG CTGGACCTAG GGCAGACCAA TCTTCTGCCA GTGGTCATTT
    Consensus TTTGAGAAAG CTGGACcTAG GGCAGAcCAA TCTTCTGCCA GTGGTCATTc 2251
TAstV2_2.seq  TTGA.
  CA_ORF2.seq TTGAA
  PA_ORF2.seq TTGAA
  MI_ORF2.seq TTGAG
  TX_ORF2.seq TTGA.
  MN_ORF2.seq TTGA.
    Consensus TTGA.
```

FIG. 2C8

SEQIDNO:15

>Canada_ORF1b.seq

```
GAAGTTAGAAGATCATGTGGTCAGTGGAGAGTGTCAAAAAAACTAATAGAGGGGCCTGTGACAACAAAGGCCCCTACCCC
CGTACCAGATTGGCTTAAAATATTTGCATGGGAAGATGATATATTACCACCCGAAGGAAAAATCGCATTGCCAGAAAATG
TCACTCTAATCGGGCATATACCAGTTGACAAGTTGGTTTCACGTACCAAGAAAGTCCAGGACCCATTGTTAGGCCTTGTA
ACACCTTGGAAACAGGATGTGTATGACTCAACAACATGGACTGTAAAAGCTTATAACAAAATGTTTGAGAAATTCCATTA
CCACGACCCAGTtGATTTTGTAGAGCAATATGCTGAGTTTGTGCTTCTGTGtGACAAtAtGgTGtTgAGaGAgcATGATT
ATATGGCAAACAGTCATATTACACCAATTATGTCAACAGAGAAAAATGTCAACAGTACACCAGCATACCCGAAATTTCAA
GCCTATGATAGTGAAGCTGAGTATCTGGAAGATTGTGGGTGGCAAGAGTACCTGGATGTTGTRTCCGATCCAGAGTCTAT
AAATCATAGACCCCTATGGTGGTGCTTCCTCAAAAATGAAGTTCTCAAGAAAGAGAAAATTGAGGATAATGACATCCGAA
TGATACTGTGCACCGACCCAGTTTTCACCAGGATTGGGGCTATGTTTGAACAGGATCAGAACAACAGAATGAAACAACAG
ACTGAAACAAGATCTGCACAGGTAGGATGGACACCCTTTTTCGGTGGCTTGGATCGCAGGGTTCGTAGGTTGTGTGGAGA
TGGAGACAGGTATTTTGTTGAGATGGACTGGACACGGTATGATGGACTATACCAAAATCATTATTTTGGAGAATTAGGC
AAATTAGGTTCTTCTTCCTTCATGATTCTCATAAGACCCCAAAGATGCGGCGTTTGTACAATTGGTATGTGAAAAATTTG
TTGGAAAAAATTATCTTATTGCCAACTGGAGAAGTTTGCCAGGTCAAGAAAGGAAATCCGAGTGGTCAGTATTCAACAAC
TGTGGATAATAATATGATCAATGTCTGGCTAACAACATTTGAGGTTTCATACCTATTCTTCAAACAGCGTGGTAGACTGC
CAACAGAGAAAGAGCTGCAAGAGAACTGCTCCATGATATGCTACGGGGATGACAGACTTCTTTCTATCCGTAAAGGGTTT
GTTGAGTACGAACCTGACACAGTCATTGAGATGTACAAGAACATCTTCGGGATGTGGGTAAAAAGAAACAACATCAAAAT
CCAGGACACACCTGAAGGGCTCTCTTTTTGTGGGCTTACAATAGTGAAATCAAATACTGGTGCATATGTTGGTGTTCCCA
ATGTGAACAAAATATTGTCAACCTTGGAAAATCCAGTACGTAGGCTACCAGATGTTGAGTCTCTTTGGGGTAAACTGGTT
TCCCTGCGCATATTGTGTGAAAAACGCTCCCAGCAATGTTAAACACTTTCTTGATGAGCAGATTAGCAATGTTGAGGAGTT
CGCCGCCAGAGAAAACATACAACTTCCTGAGGTCGGGCCCGACTTCTATTCCAGAATATGGTGAG
```

SEQIDNO:16

>TX_ORF1b_10-11.seq

```
AACAAGATCTGCACAGGTAGGATGGACACCCTTCTTCGGTGGCTTGGATCGCAGGGTTCGTAgGTTGTGTGGGGATGGAG
ACAGGTATTTTGTTGAGATGGACTGGACGCGGTATGATGGACTATACCAAAGCCATTATTCTGGAGAATTAGACAGATC
AGGTTTTCTTCCTCCATGATTCCCATAAGACCCCAAGAATGCGGCGCCTGTACAATTGGTATGTTAAAAATTTGCTGGA
AAAAATCATTTTGCTACCAACTGGGGAGGTCTGCCAGGTTAAGAAAGGAAATCCGAGTGGACAATATTCAACAACTGTGG
ATAACAATATGATAAATGTCTGGCTAACAGCGTTTGAAATTTCATACCTCTTTTTCAAACAGTTTGGTAGACTGCCAACA
GAGAAAGAACTGCAAGAGAACTGCTCCATGATATGCTACGGAGATGACAGACTTCTTTCCATCCGCAAAGGATTTGTTGA
GTATGAACCTGATACAGTCATTGAGATGTACAAGAACATCTTTGGAATGTGGGTTAAAAAAAATAACATCAAAATTCAGG
ATACACCCGAAGGGCTCTCTTTCTGCGGGCTTACAATAGTGAAGTCAAGAACCGGGCATATGTTGGAGTCCCAAATGTG
AACAAAATATTGTCAACTTTGGAAAATCCAGTCCGCAGGTTGCCAGATGTTGAGTCCTTGTGGGTAAATTGGTTTCCCT
GCGCATATTGTGTGAAAATGCTCCCAGCAATGTTAAACATTTTCTTGATGAGCAGATGagcaaTGTTGAGGAGTTCGCCG
CCAg
```

SEQIDNO:17

>PA_ORF1b_10-11.seq

```
AATAAGGTCTGCACAGGTCGGATGGACACCCTTTTTCGGTGGCTTGGATCGCAGGGTTCGTAGGTTGTGTGGGGATGGAG
ACAGGTATTTTGTTGAGATGGACTGGACGCGGTATGATGGACTATACCAAAGCCATTATTCTGGAGGATCAGACAGATT
AGGTTTTCTTCCTCCATGATTCCCATAAAACCTCAAAAATGCGGCGCTTATACAATTGGTATGTAAAAAATTTGTTGGA
AAAAATCATCTTACTGCCAACTGGGGAGGTCTGCCAGGTTAAGAAAGGAAATCCAAGTGGACAATATTCAACAACTGTGG
ATAACAACATGATAAATGTCTGGCTAACAGCATTTGAAATTTCATACCTCTTTTTCAAACAGTTTGGTAGGCTGCCAACA
GAGAAAGAACTGCAAGAGAACTGCTCCATGATATGCTACGGAGATGACAGACTTCTTTCCATTCGCAAAGGGTTTGTTGA
GTATGAACCTGAAACAGTCATTGAGATGTATAAGAACATCTTTGGGATGTGGGTTAAAAAGACTAACATCAAGATTCAGG
ATACACCCGAAGGGCTCTCTTTCTGCGGGCTAACAATAGTGAAATCAAAAACTGGAACATATGTTGGTGTCCCAAATGTG
GACAAAATATTGTCAACTTTGGAAAATCCAGTCCGCAGGTTGCCAGATGTTGAGTCCTTGTGGGTAAATTAGTTTCCCT
GCGCATATTGTGTGAAAATGCTCCCAGCAATGTCAAACATTTTCTCGATGAGCAGATTGGCAatgtTGTTGAGGAGTTCG
CCGCCAR
```

FIG. 2D1

SEQIDNO:18
>MI_ORF1b.seq
TGGAGAGTGCCAAAAAAACTAGTAGAGGGGCCTGTGACAACAAAGGCCCCTACCCCCGTACCAGATTGGCTTAAAATATT
TGCATGGGAAGATGACATATTACCACCTGAAGGAAAAATTGCTTTACCAGAAAATGTTACTCTAATTGGGCACATACCAG
TTGACAAATTGGTCTCGCGTACCAAGAAAGTCCAAGACCCATTGCTAGGCCTTGTAACACCATGGAAACAAGATGTGTAT
GATTCAACAACATGGACTGTAAAAGCTTACAACAAAATGTTTGAGAAATTCCATTACCACGACCCAGTTGATTTTGTAGA
GCAATATGCTGAGTTCGTGCTTCTGTGTGACAACATGGTGTTGAGAGAGCATGATTATATGGCAAACAGTCATATTACAC
CAATTATGTCAACAGAGAAGAATGTCAACAGTACACCAGCATACCCGAAATTCCAAGCCTATGATAGTGAAGCCGAGTAT
TTGGAAGATTGTGGGTGGCAAGAGTATCTGGATGTTGTATCCGATcCAGAGTCTATAAATCATAGAcCCCTATGGTGGTG
CTTCCTCAAAAATGAAGTTCTCAAAAAAGAGAAAATTGAGGATAATGATATTCGAATGATATTGTGCACCGACCCGATTT
TCACCAGGATTGGGGCTATGTTTGAGCAGGATCAGAACAACAGAATGAAACAACAGACTGAAACAAGATCTGCACAGGTC
GGATGGACCCCCTTTTTCGGCGGCTTGGATCGCAGGGTTCGTAGGTTGTGTGGAGATGGAGACAGGTATTTTGTTGAGAT
GGACTGGACGCGATATGATGGGACTATACCAAAATCACTATTTTGGAGGATTAGACAGATTAGGTTTTTCTTCCTTCATG
ATTCCCATAAGACCCCAAAAATGCAGCGCTTGTACAATTGGTATGTAAAAAATTTGCTGGAGAAAATCATTCTATTGCCA
ACTGGGGAGGTCTGCCAGGTCAAGAAAGGAAATCCGAGTGGACAATATTCAACAACTGTGGACAACAATATGATAAATGT
CTGGCTAACAGCGTTTGAAATTTCATACCTCTTCTTCAAACAGTTTGGTAGACTGCCAACAGAGAAAGAACTGCAAGAGA
ACTGCTCCATGATATGCTACGGAGACGACAGACTTCTTTCCATCCGCAAGGGGTTTGTTGAGTATGAACCTGAAACAGTC
ATTGAGATGTATAAGAACATCTTTGGAATGTGGGTTAAAAAGACTAACATCAAGATTCAGGATACACCCGAAGGGCTCTC
TTTCTGTGGGCTAACAATAGTGAAGTCAAAAACCGGGACATATGTTGGTGTCCCAAATGTGGACAAAATATTGTCAACTT
TGGAAAATCCAGTCCGTAGGTTGCCAGATGTTGAGaTACTtGTGGGGTAAAgTTcGGTTTCCCTGCGCaTATTGTGTGAA
AATGCTCCCAGCAATGTCAAACATTTTCTTGATGAACAGATTGGCAaTGTTGAGGAGTTCGCCGCCAAAGAAAACATACA
ACTTCCTGAGGTCGGGCCCGACTTCTATTCCAGAATATGGTGAG SEQIDNO:20
>C01b_10-11.seq
ATAAGGTCTGCACAGGTCGGATGGACCCCCTTTTTCGGCGGCTTGGATCGCAGGgTTCGCAgGTTGTGTGGTGATGGATA
TAGGTATTTTGTTGAGATGGACTGGACAcGGTATGATGGGACTATACCAAAATCATTATTTTGGAGAATTAGGCAAATTA
GGTTCTTCTTCCTTCATGATTCTCATAAGACCCCAAAGATGCGGCGCTTGTATAATTGGTATGTGAAAAATCTGTTGGAA
AAAATCATCTTATTGCCAACTGGAGAAGTTTGCCAGGTTAAGAAAGGAAATCCAAGTGGTCAGTATTCAACAACTGTGGA
TAATAATATGATCAATGTCTGGCTAACAACATTTGAGGTTTCATACCTATTCTTTAAACAGCGTGGTAGACTGCCAACAG
AGAAAGAGCTGCAAGAGAACTGCTCCATGATATGCTACGGGGATGACAGACTTCTTTCCATCCGTAAAGGGTTTGTTGAG
TACGAACCTGATACAGTCATTGAGATGTACAAGAGCATCTTTGGGATGTGGGTAAAAAGAAGCAACATCAAAATCCAAGA
TACACCTGAAGGGCTCTCTTTTTGTGGGCTTACAATAGTAAAATCAAGTGCTGGTGCATATGTTGGTGTTCCCAATGTGA
ACAAAATATTGTCAACCTTGGAAAATCCAGTACGTAAGCTACCAGATGTTGAGTCTCTTTGGGGTAAATTGGTTTCCCTG
CGCATATTGTGTGAAAACGCTCCCAGCAATGTTAAACACTTTCTTGATGAGCAGATTAGCAaTGTTGAGGAGTTCGCCGC
CAA

FIG. 2D2

SEQIDNO:22
>CO_ORF1a.seq
```
AAGTGGGGCGATGGCCCAGGCGGGTCGCAGTGGCGATGCTTTTGCATCCCTTGATCAACGGCGGGAGCGCCAAGAAGAAC
AGGCGCAGTCCGGCCTTGACAAGGTGTTCTATTTCCAAGGCGTGGTTGAACTATTCAACCGTATGAAAATCGCCTATGGA
AGGACACCGGCTTGGACAGCCCTCATGAAGTGTAACGCCATATACTTGAAAGATTTTAAAACAGCAGTTGGCGTTGAGGG
TACCCGCTATGGGCTCTTTTTCGCAGAAGAAGTGACTAAACCAACTTGGTCACCCGACATTGGAGCAAACTTGATAACTT
TGGGCGAAAAGGCCTGTTTAGACGCCCAAAATGCAAAATATGAAAGATTGCAAGCCTCACTTAAAACAACTAGTGGCCTT
GTTCATCAAGTGATGGAAAAAACTAGGGAAGCTAAAGAGAACCTAGAGAAAGCCAATAAGATCCAAGAGCAACTTGACAA
GGTTATTGAGAGCAACAAAGCTTTACACCGGAAGATACAGGAGAAAAACCGAGAGAAGATGCAGGAATACATGGTAAGGT
TGCATAACACGCAGAAAGATCGTGATGATTGGGTTCAAAGATGCTCCAGGTTAGAACAGGAGAATGTCACGTTGCAGAAA
AGGTTGAAGGAGAAAGAGAACGCGCTGGTATCTGTTGGGTGGGATCTTTTAGGCTGGATAGTTATTTCAGTTCTCGTGTT
CGGCCTGATTTCACTCGCAGACGCGCAAAACTTGACTCCACCAGCCAAGATTGTGATAACTCCAGGGCAAGCAGAGTTTA
TGGACCTAGCCAAATTGGAAAAAATCCAGATCAGAAAGTACCGACTGGATAGTTGTGAATTACCACCTGAGAAAGGTTGC
GTGTTGTACAAGGATTACCTTACCACCAGGCCGGTAAGCTTTTTGGAGTTGATGGCCAAATGTTCAAAACCTGACTGGGT
CTCGGAGAGCAGTTACAATGAAACAACTCTAATGGAAGAATGCGTCCAGaTCTTTGGTGCAGAGTGGTGTGAAGGAAAGC
TTGTTGATCTTGTACCAAGAAAGTGTGGCGAGCAACATGTCTTAGTTAACATCATAGAGCAAATTGAAAAAACTAGAGAA
GTTGTGACCCTTATATATAGTAAGGTGATGTCATACAGGCTAGATATGTGGATAACATCTATTTTTAGTTTAGTTTTGGC
AGGTAATAAGGAAAAATTGTTTAAAATGGCTCCCTTTATCTTTGTAGCATGGTTTTTAAATATACCAGTGTTTTTAACTT
GTGTGGCAGTTAACATTTTTCCAGTTGTTTCCCTGCCTTTCATTTTGTTCCAGATTTTTATGCCACAGTTTGTTTTGGTA
AATGCCTTTCTTCTATGGTTAACACTCACTTTAACAGCATTTTATTGGAGTGAGGGGCCCAAAATACTGATGGAGATAAG
CTATGCCCTTGTGTATACCATCGGCTTTGTTTTATGGTCCCTTGGACTAGCTGTGGGGTGACGCTCAAATTGACAATGG
TACATCAGATATTAATGTTTGTGTTGTTGCCGCAGCTATTTGCGGAACCAAGTTTGCATGCACAACAATAACAGTGCAA
CATCCAGATGGAACAACCGCAAAATATACCCGGGTTGGTAAGCTAAAGAATAATGTTGTGAATCAGTGCAAGAAGGTAGT
CACGACATTGCAGACAAGAGGCGTGATACCAGCAACGCCTGCGAAAACAGCATCTATTGTTATTGTTGAGGGCAAAAATG
GAACAGGCGTTGGGTTCAGGTTTATGAATTATATTCTCACAGCAGAACACGTGGTTCAGGGATCAGATATAGCAACACTT
AAAAGTGGCAGTGTTAGTGTGAAATCCAAAGTCATCAAAACGATCCCAATATTTGAGAGTGTTGACAATGTTGCAGTGCT
AAAAATTGCCACCTGAGCTCAATAGCGTGAAGCCTATCAAATTAGCAAAGAAGGTTCAAAGTGACTATCTGACACTGACAG
CCTATGATCCAAATTTCCAACATGCCGTTACTTTCACCGGGTGGTGTATTATAGATGGAAATTGGCTTAATAACTCCTTT
GATACAAAATTTGGGAATAGTGGTGCACCTTATTGTGATCATGACGGTAGGCTAGTTGGTATCCACCTAGGCACACAGGG
TGTTCTGTCCCAAGGCATAGTCATTGTAGACGCATTGAAGAATACATTCCAGCTTGCGGATCAGTGTAGACCACAGAACT
TTGACATGGATGAGTTCCTTGAGAAAGTTATAGCAGGAACAAAAGTGTCACATGCAGCGATCCTAAAAGAACTGGAAGAA
CTTAGAGAAGAGGTGCAATTTTTAAAGAAAAAATGTGTCACTTATGATGACTACTGGCTATGCCAAACCATCTTTGGGCA
GGCCAAAGGGAAGACGAAGAAAACAGTCAGAGGCCGTAAACACCTTGTTACCAAAAGAGCTCTTGGGAAAGGCCACTTCA
TGAAGATGAGGATGCTCACTGATGAGAATATCAGAATATGATTGAAAAGGGCTTCTCAGCAGAGGAAATAAGGGAGGCA
GTCAACGCACTCCGAGACGAAGCATGCTTAATTACTGTATTGATAATGATGTTGATGACGAAGGTGAGGAAGATTGGTA
TGATGACATGGTAGAGACAGATAGAGTTAACCAGGAGATCGATGAGGCCATAGAGCGTGCCATGGAAGATCGTGGTGAGT
TCTACCAGAAGAAATCCCGCCTTACCTTTGTTGAACAGGCCATGATGCATTTGATCCAAGTGAGCAAAGAGAGAAGCCAG
ACTGCTAAATTAGAAGTTCAGAAGGAGAATGAAGCTCAACTAGTGAAGATGTTTGAGCGGTGTGTCACAGATGAGAATAC
ACCTGAGGGTACCACCTCTATAGCGGCTTTGTCCACAGAAGATGATGTTAGGCTTGTTGAAGGGAAAGTCATTGATTTCA
CCAAAGCAAAGAATATCCCAGTTGATGGGGAAATTAGAAGAGAGATCATTCCTGGAACAAAATGCACTGAGATTTCCACT
GGACCTGAAAATAAGAAGAACATATTGAAGAAAAAGGATACACACATAGCTGAGGGTAAAGTTGAAAATAAGTCATCACA
GCAGCCGGTTGACGTTAAGGATGATAAACCCGTAGCCTTGGAACAACGCAAGCCTAGAGCTTGTAAATGGTGCGGTTCAT
CACAAAAACATGATTACCGGGAATGTCGGTTTCAACGTGAAAAACGCTTTTGTGTGTATTGTGCAGCTATGCACTCAATG
TTTGAGGGCCATATAAGACCAATAGAGTGCACTAGTTGTAAGAAAAGTTTTTCAGGAATTGAGAAGTTAGAAGATCATGT
GGTCAGTGGAGAGTGTCAAAAAAACTAGTGGAGGGGCCTGTGACAACAAAGGCCCCTACCCCCGTACCAGATTGGCTTAA
AATATTTGCATGGGAAGATGcACATATTACCACCTGAAGGTAAAACTGCCTTACCAGcAAAATGTTAYTCTAATTGGtAC
ATATACCAGTTGtTKAAGTTgGTCTCGCGCACCAAGAAAGTCCAGGATCCATTGTTAGGCCTTGTAACACCATGRAAACA
AGATGTGTATGATTCAWCAACATGGACTGYWRWAGCTTACACCaAMaATGTTKGAGAARTTCCATTACCACGACCCAGTT
GACTTTGTAGAGCAGTATGCTGAGTTTGTGCTGYTGTGTGACAAYATGRTGKTGWKRARRSAKSAYKAYATGRYRRMTAR
CAAYATCACACCAATCATSWCRACAGARRAAAATRWYRWCARTACAMCASCATMCYMMMCTTTGAAGCCCGGGTGTCACA
GATGAGAACACACCTGAGGGTACCACCTCTATAGCGGCTTTGTCCACAGAAGATGATGTTAGGCTTGTTGAAGGGAAAGT
CATTGATTTTACCAAAGCAAAGAATATCCCAGTTGATGGGGAAATTAGAAGAGAGATCATTGCCTGGAACAAAATGCACT
GAGATTTGCCACTGGACCTGAAAATAAGAAGGAACATATGTAAGAAAAAGGCATACACACATAGATGAGGCKGAAAKTGA
```

FIG. 2D3

SEQIDNO:23
```
>CA_ORF1a-1b.seq
GGCGATGGCCCAGGCGGGTCGCAGTGGCGATGCTTTTGCATCCCTTGATCAACGGCGGGAGCGCCAAGAAGAACAGGCGC
AGTCCGGCCTTGACAAGGTGTTCTACTTCCAAGGCGTGGTTGAATTATTCAACCGTATGAAAATCGCCTATGGAAGGACA
CCGGCTTGGACGGCCCTCATGAAGTGTAACGCCATATACTTGAAAGATTTTAAAACAGCAGTTGGCGTTGAGGGTACCCG
CTATGGGCTCTTTTTCGCAGAAGAAGTGACTAAACCAACTTGGTCACCCGACATTGGAGCAAACTTGATAACTTTGGGCG
AAAAGGCCTGTTTAGACGCCCAAAATGCAAAATATGAAAGATTGCAAGCCTCACTCAAAACAACTAGTGGCCTTGTGCAT
CAAGTGATGGAAAAAACTAGGGAAGCTAAAGAGAACCTAGAGAAAGCCAATAAGATCCAAGAGCAACTTGACAAGGTCAT
TGAGAGCAACAAAGCTTTACACCGGAAGATACAGGAGAAAAACCGAGAAAAGATGCAGGAATACATGGTAAGGTTGCACA
ATACGCAGAAAGATCGTGATGATTGGGTTCAGAGATGCTCCAGGTTAGAACAGGAGAATGTCACTTTGCAAAAAAGGTTG
AAGGAGAAAGAGAACGCGCTGGTATCTGTTGGGTGGGATCTTTTAGGCTGGATAGTTATTTCAGTGCTTGTATTCGGCCT
GATTTCACTCGCAGACGCGCAAAACTTGACTCCACCAGCCAAGATTGTGATAACTCCAGGGCAAGCAGAGTTCATGGACC
TAGCCAAATTGGAAAAAATCCAGATCAGAAAGTACCGACTGGATAGTTGTGAATTACCACCTGAGAAAGGTTGCGTGTTG
TACAAGGATTACCTTACCACCAGGCCGGTAAGCTTTTTGGAGTTGATGGCCAAATGTTCAAAACCTGACTGGGTTTCGGA
GAGCAGTTACAATGAAACAACTCTAATGGAAGAATGCATCCAGATCTTTGGCGCAGAGTGGTGTGAAGGAAAGCTTGTTG
ATCTCGTACCAAGAAAGTGTGGCGAGCAACATGTATTAGTTAACATCATAGAGCAAATTGAAAAAACCAGAGAAGTTGTG
ACCCTTATATATGGTAAGGTGATGTCATACAGGCTAGATATGTGGATAACATCTATTTTTAGCCTAGTTTTGGCAGGTAA
CAAGGAAAAATTGTTTAAAATGGCTCCCTTCATTTTTGTAGCATGGTTTTTAAACATACCAGTGTTTTTAACTTGTGTGG
CAGTCAACATTTTTCCAGTTGTTTCCCTGCCTTTCATTTTGTTCCAGATTTTTATGCCACAGTTTGTTTTGGTAAATGCC
TTTCTTCTATGGTTAACACTCACTTTAACAGCATTTTATTGGAGTGAGGGCCCAAAATACTGATGGAGATAAGCTATGC
CCTTGTGTATACCATCGGCTTTGTTTTaTGGTCCCTTGGACTAGCCGTGGGGGTGACGCTCAAaTTGACAATGGTACATC
AGATATTAATGTTTTGTGTTGTTGCCGCAGCTATTTGCGGAACCAAGTTTGCATGCACAACAATAACAGTGCAACACCCA
GATGGAACAACCGCAAAATACACCCGAGTTGGTAAGCTAAAGAATAATGTTGTGAATCAGTGCAAGAAGGTAGTCACGAC
ATTGCAGACAAGAGGCGTTATACCAGCAACGCCTGCGAAAACAGCATCTATTGTTATTGTTGAGGGCAAAAATGGAACAG
GTGTTGGGTTCAGGTTTATGAATTATATTCTTACAGCAGAACACGTGGTTCAGGGATCAGATATAGCAACACTCAAAAAT
GGCAGTGTTAGTGTGAAATCCAAAGTTATCAAAACGATCCCAATATTTGAGAGTGTTGACAATGTTGCAGTGTTAAAATT
ACCACCTGAGCTCAATAGCGTGAAGCCTATCAAATTAGCAAAGAAGGTTCAAAGTGACTATCTGACATTGACAGCCTATG
ATCCAAATTTCCAACATGCCGTTACTTTTACCGGGTGGTGTATTATAGATGGAAATTGGCTTAATAACTCCTTTGACACA
AAATTTGGGAATAGTGGTGCACCTTATTGTGATCATGACGGTAGGCTAGTTGGTATCCATCTAGGCACACAGGGTGTTCT
GTCCCAAGGCATAGTCATTGTAGATGCATTGAAAAATACATTCCAGCTTGCGGATCAGTGTAGACCACAGAATTTTGACA
TGGATGAGTTCCTTGAGAAAGTTATAGCAGGAACAAAAGTGTCACATGCAGCGATCCTAAAAGAACTGGAAGAACTTAGA
GAAGAGGTGCAATTTTTGAAGAAAAAATGTGTTACCTATGATGACTACTGGCTATGCCAAACCATCTTTGGGCAGGCCAA
AGGGAAGACGAAGAAACAGTCAGAGGCCGTAAACACCTTGTTACCAAAGGGCTCTTGGGAAAGGCCCACTTCATGAAGA
TGAGGATGCTCACTGATGAAGAATATCAGAATATGATTGAAAAGGGCTTCTCAGCAGGAAATAAGGGAGGCAGTCAAC
GCACTCCGAGAACAAGCATGGCTTAATTACTGTATTGATAATGATGTTGATGACGAAGGTGAGGAAGATTGGTATGATGA
CATGGTAGAGACAGATAGAGTTAACCAAGAGATCGATGAGGCCATAGAGCGTGCTATGGAAGATCGTGGTGAGTTCTACC
AGAAGAAATCCCGCCTTACCTTTGTTGAACAGGCCATGATGCATCTAATCCAAGTTAGCAAGGAGAGAAGCCAGACTGCT
AAATTAGAAGTTCAGAAGGAGAATGAAGCTCAACTAGTGAAGATGTTTGAACGGTGTGTCACAGATGAGAATACACCTGA
GGGTACCACCTCTATAGCGGCTTTGTCCACAGAAGATGATGTTAGGCTTGTTGAAGGGAAAGTCATTGATTTCACCAAAG
CAAAGAATATCCCAGTTGATGGGGAAATTAGGAGAGAGATCATCCCTGGAACAAAATGCACTGAGATTTCCACTGGACCT
GAAAATAAGAAGAACATATTGAAGAAAAAGGACACACACATAGCTGAGGGTAAAGTTGAAACTAAGTCATCACAGCAGCC
GGTTGACGTCAAGGATGATAAACCCGTAGCCTTGAACAACGTAAGCCTAGAGCTTGTAAATGGTGCGGTTCATCACAGA
AACATGATTACCGGGAATGTCGGTTTCAACGTGAAAAGCGCTTTTGTGTGTATTGTGCAGCTATGCACTCAATGTTTGAG
GGCCACATAAGATCAATAGAGTGCACTAGTTGCAAGAAAAGTTTTTCAGGAATTGAGAAGTTAGAAGATCATGTGGTCAG
TGGAGAGTGTCAAAAAAACTAATAGAGGGGCCTGTGACAACAAAGGCCCCTACCCCCGTACCAGATTGGCTTAAAATATT
TGCATGGAAGATGACGTATTACCACCTGAAGGTAAAACTGCCTTACCAGAAAATGTTACTTTAATTGGACATATACCAG
TTGATAAGTTGGTCTCGCGCACCAAGAAAGTCCAGGATCCATTGTTAGGCCTTGTAACACCATGGAAACAAGATGTGTAT
GACTCAACAACGTGGACTGTAAAAGCTTACACCAAAATGTTTGAGAAATTCCATTACCACGACCCAGTTGACTTTGTAGA
GCAATATGCTGAGTTTGTGCTGTTGTGTGATAATATGGTGTTGAGAGAGCATGACTATATGGCAAATAGCAATATCCACAC
CAATCATGTCAACAGAGAAAAATGTCAATAGTACACCAGCATACCCAAAATTTCAAGCCTATGATAGTGAAGCCGAGTAT
TTGGAAGATTGTGGGTGGCAAGAGTACCTGGATGTTGTGTCTGATCCAGAAACTATAAATCGTAGACCCCTATGGTGGTG
CTTCCTCAAAAATGAAGTTCTCAAAAAAGAGAAAATTGAGGACAGTGACATTCGAATGATATTGTGCACCGACCCaGTTT
TTACCAGGATTGGGGCTATGTTTGAACAGGATCAGAACAACAGAATGAAACAACAGACTGAAACAAGATCAGCACAGGTA
GGATGGACACCCTTCTTCGGCGGCTTGGATCGCAGGGTTCGCAgTTGTGTGGTGATGGAGATAGGTATTTTGTTGAGAT
GGACTGGACGCGATATGATGGGACTATACCAAAATCACTATTTTGGAGGATTAGGCAAATTAGGTTCTTCTTCCTTCATG
ATTCTCATAAGACCCCAAAGATGCGGCGCTTGTACAATTGGTATGTGAAAAATCTGTTGGAAAAAATTATTTTATTGCCA
ACTGGAGAAGTTTCCAGGTCAAGAAAGGAAATCCAAGTGGTCAGTATTCAACAACTGTGGATAATAATATGATCAATGT
CTGGCTAACAACATTTGAGGTTTCATACCTATTCTTCAAACAGCGTGGTAGACTGCCAACAGAGAAAGAGCTGCAAGAGA
ACTGCTCCATGATATGCTACGGGGATGACAGACTTCTTTCCATCCGTAAAGGGTTTGTTGAGTACGAACCTGATACAGTC
ATTGAGATGTACAAGAACATCTTTGGGATGTGGGTAAAAAGAAACAACATTAAAATCCAAGATACACCTGAAGGGCTCTC
TTTTTGTGGGCTTACAATAGTAAAATCAAGTGCTGGTGCATATGTTGGTGTTCCCAATGTGAACAAAATACTGTCAACCT
TGGAAAATCCAGTACGTAGGCTACCAGATGTTGAGTCTCTTTGGGGTAAATTGGTTTCCCTGCGCATATTGTGTGAAAAC
GCTCCCAGCAATGTTAAACACTTTCTTGATGAGCAGATTAGCAATGTTGAGGAgTTCGCCGCCAGAGAAAACATACAACT
TCCTGAGGTCGGGCCCGACTTCTATTCCAGAATATGGTGAGA
```

FIG. 2D4

SEQIDNO:21
>AK_ORF1b.seq
GAAGTTAGAAGACCATGTGGTCAGCGGAGAGTGTCAAAAAAACTAGTAGAGGGGCCYGTGACAACAAAGGCCCCTACCCC
CGTACCAGATTGGCTTAAAATATTTGCATGGGAAGATGACATATTACCACCTGAAGGAAAAATTGCCTTACCAGAAAATG
TTGCCTTAATTGGACACATACCAGTTGACAAATTGGTCTCGCGTACCAAGAAGGTCCAAGACCCCCTGTTAGGCCTTGTA
ACGCCTTGGAAACAGGATGTGTATGACTCAACAACATGGACTGTAAAAGCTTACAACAAAATGTTTGAGAAATTTCATTA
CCACGACCCAGTTGATTTTGTAGAGCAGTATGCTGAGTTTGTGCTTTTGTGTGACAATATGGTGTTGAGAGAGCATGACT
ATATGGCAAATAGTTACATCACACCAATTATGTCAACAGAGAAAAATGTCAACAGCACACCAGCATACCCGAAATTTCAG
GCCTATGACAGTGAAGCCGAGTATCTGGAAGATTGTGGGTGGCAAGAGTACCTGGATGTTGTGTCTGATCCAGAAACTAT
AAATCATAGACCCCTGTGGTGGTGCTTCCTCAAGAATGAAGTTCTCAAAAAAGAGAAAATTGAGGATAGTGACATTCGGA
TGATACTGTGCACCGACCCAGTTTTCACCAGGATTGGGGCTATGTTTGAACAGGACCAGAACAACAGAATGAAACAACAG
ACTGAAACAAGATCTGCACAGGTAGGTTGGACACCCTTCTTCGGCGGCTTGGATCGCAGGGTTCGCAGGTTGTGTGGTGA
TGGAGACAGGTATTTTGTTGAAATGGACTGGACGCGGTATGATGGGACTATACCAAAGCCACTTTTTTGGAGAATTAGAC
AGATTAGGTTTTTCTTTCTTCATGACTCCCATAAAACTCCAAAAATGCGGTGTTTGTACAATTGGTATGTAAAAAATTTG
TTGGAAAAAGTCATTTTATTGCCAACTGGAGAGGTCTGCCAAGTTAAAAAAGGAAATCCGAGTGGACAATATTCAACAAC
TGTGGATAACAACATGATAAATGTCTGGTTAACAACATTTGAGATTTCATTTCTCTTTTTCAAACAGCGTGGTAGATTGC
CAACAGAGAAAGAATTGCAAGAGAACTGCTCCATGATATGCTATGGGGATGACAGACTTCTTTCTATCCGCAAAGGGTTT
GTTGAGTATGAACCTGATACAGTTATTGAGATGTACAAGAACATCTTTGGGATGTGGGTAAAAAGGAATAACATTAAAAT
CCAAGATACACCTGAAGGGCTCTCTTTTTGTGGACTTACAATTGTAAAATCAAGCAATGGGGCATATGTTGGAGTTCCAA
ATGTGAACAAGATACTGTCAACTTTGGAAAAACCCAGTCCGCAGACTGCCAGATGTTGAGTCCTTGTGGGGTAAATTGGTT
TCCCTGCGCATATTGTGTGAAAATGCTCCCAGCAATGTCAAACACTTTCTTGATGAACAGATTGGCaATGTTGAGGAGTT
CGCCGCCAGAGAAAATATACAACTGCCTGAAGTCGGGCCCGACTTCTATTCCAAAATATGGTGAG

FIG. 2D5

SEQIDNO:24

>AK_ORF1a.seq

```
ATGGCCCAGGCGGGTCGCGGCAGCGATGCTTTTGCATCCCTTGATCAACGCCGGGAGCGCCAAGAAGAACAGGCGCAAAC
CGGCCTTGaCAAGGTGTTTTTCTTCCaAGGCGTGGTTGAGTTATTCAACCGCATGAAAATTGCCTATGGAAGGACACCGG
CGTGGACAGCCCTCATGAAGTGTAACGCCATATATTTGAAAGATTTCAAAACAGCAATTGGCGTTGAGGGTACCCGCTAT
GGGTTATTCTTCGCAGAAGAAGTGACCAAACCAACCTGGTCACCCGACATTGGAGCAAATTTGATGACCTTGGGCGAAAA
GGCTTGTATAGACGCCCAGAATGCAAAATATGAAAGATTGCAAGCATCACTTAAAACAACCAGTGCCCTAGTGCACCAAG
TGATGGAAAAAACTAGGGAGGCTAAAGAGAATTTGGAGAAAGCTAATAAGATCCAAGATCAGCTTGACAAGGTTGTTGAA
AGCAATAAGACCTTACACCGGAGGATACAGGAGAAAAACCGAGAGAAGATGCAGGAGTATATGGTGAGGTTGCATAACAC
GCAGAAGGATCGTGATGACTGGGTTCAGAGATGCTCTAGGCTGGAACAGGAGAATGTCAATCTGCAGAAAAGGTTAAAGG
AGAAAGAGAATGCGCTGATATCTGTTGGATGGGATCTTTTAGGCTGGATAGTTATTTCAGTGCTTGTATTCGGCCTGATT
TCACTTGCAGACGCGCAGAACCTGACTCCACCAGCCAAGATTGTGATAACTCCAGGACAAGCAGAGTTCATGGACCTAGC
TAAATTGGAAAAAATCCAGATCAGAAAGTATCGACTGGAGAGTTGTGAGTTACCACCTGAGAAAGGTTGCGTATTGTATA
AGGATTATCTCACCACCAGGTCAGTAAGCTTCTTGGAGTTGATGGCCAAATGTACAAAACCTGACTGGATCTCGGAGAGC
AGTTATAATGAAACAACCCTTATGGAAGAGTGCATTCAGATTTTCGGTGCAGAGTGGTGTGAAGGAAAACTTGTTGACCT
TGTGCCAAGGAAATGTAGTGAACAACATATTCTAGTTAATTTTATGGAGCAAATTGAAAAAACTAGAGAAGTTGTAACCC
TCATATATGGGAAGGTGATGTCATACAGGTTGGATATGTGGATAACATCCATCTTCAGCTTAGTTTTAGCAGGTAATAAG
GAAAAATTGTTTAAAATGGCTCCTTTTATTCTTGTGGCATGGTTTTTGCGTATACCAGTGTTTTTGACCTGCGTGGCAGT
TAACATTTTTCCGCTTGTTTCACTGCCCTTTATATTGTTTCAGATCTTTATGCCACAGTTTGTCCTGATAAATGCTTTCC
TCTTATGGTTAACACTCACTTTAACAGCTTTTTATTGGAATGAGGGGCCCAAAATACTTATGGAGGTGAGCTATGCCCTT
GtgtatACCATCGGCTTTGTTTTATGGTCTCTTGGATTGGCTGTGGGTGTGACGCTTAAATTGACAATGGTACATCAGAT
ATTGATGTTTTGTGTTGTTGTCGCAACCATTTGTGGGACCAGATTTGCATGCGCAACAATAACAGTGCAACACCCAGATG
GAACAACCACAAAATACACCCGGGTTGGTAAGTTAAAGACAAATGTAGTGAATCAGTGTAAGAAGATGGTCACGACACTG
CAAACAAGAGGCGTAATACCAGCAACGCCTGCAAAAACAGCATCCATTGTTATTGTTGAGGGAAAAAATGGAACAGGTGT
CGGTTTCAGGTTTATGAATTATATCCTTACAGCAGAGCATGTGGTTCAGGGATCGGATATAGCAACACTTAAAAATGGCA
GTGTTAGTGTGAAATCCAAAGTTATTAAAACGATCCCAATATTTGAAAGTGTTGATAATGTTGCAGTGTTAAAATTACCA
CCTGAGCTTAATGGCGTGAAACCTATTAAATTAGCAAAGAGGGTTCAAAGTGACTATTTGACACTGACAGCYTatgatcc
aaCATTTCAACACGCCGTCACTTACACCGGGTGGTGTATAGTGGATGGGAATTGGCTTAATAATTCTTTTGATACAAAAT
TTGGAAATAGTGGTGCACCATATTGCGACCATGATGGTAGGCTAGTTGGTATCCACCTAGGCACACAGGGTGTTCTGTCC
CAAGGCATAGTCATTGTAGATGCATTGAAGAATACATTCCAGCTTGCAGATCAGTGTAGACCACAGAACTTTGATATGGA
TGAGTTCCTTGAGAAAGTCATAGCAGGAACAAAAGTTTCACCAGCAGCGATCTTAAAAGAACTGGAAGAACTTAGAGAAG
AGGTGCAATTTTTGAAAAGAAAATGTGTCACCTACGATGACTACTGGCTATGCCAAACCATCTTTGGGCAGGCCAAAGGG
AAGACGAAGAAAACAGTCAGAGGCCGTAAACACCTTGTTACTAAAAGAGCTCTTAGTAAGGGGCATTTTATGAAGATGAG
GATGCTTACCGATGAAGAATATCAGAACATGATTGAAAAGGGCTTCTCAGCAGAGGAAATAAGAGAGGCAGTCAATGAAC
TCCGGGAACAAGCATGGCTCAATTATTGTATTGATAATGACATTGACGATGAAGGTGAGGATGACTGGTATGATGATATG
GTAGAGACAGACAGGGTTAATCAGGAGATTGATGAGGCTATAGAGCGTGCCATGGAAGATCGTGGTGAATTCTACCAAAA
GAAGTCTCGCCTTACTTTTGTCGAGCAGGCCATGATGCATCTGATTCAAGTAAGTAAGGAGAGGAGCCAGACTGCCAAGT
TAGAAGTCCAGAAGGAGAATGAAGAACAACTAAAAAACATGTTTGAGCGGTGTGTCACAGATGAGAATACACCTGAGGGC
ACCACTTCAGTAGCAGTTTTGTCCACAGAGGAGGATGTTAGGCTTGTTGAAGGGAAAATCATTGACTTCTCCAAAGCAAA
AAATATTCCAGTTGACGGGGAGATAAGGAGAGAGATAATTCCCGGGACTAAGTGCACTGAGATTTCTACTGGACCCGAAA
ATAGGAAGAACATATTGAAGAAAAAGGATACACACATGACTGAGGGAAAAGTTGAGACTAAAACATCACAGCAACCGGTT
GACGTTAAAGATGATAAACCCGTAGCCTTGGAACAACGGAAGCCTAGAGCTTGTAAATGGTGCGGTTCATCACAAAAACA
CGATTACCGGGAATGTCGGTTTCAACGTGAAAAACGTTTCTGTGTGTATTGTGCAGCTATGCACTCAATGTTTGAGGGCC
ACATAAGATCGATAGAGTGCGCCAACTGTAAGAAGAGTTTCCCAGGaATTGAGAAGTTAGAAGACCATGTGGTCAGCGGA
GAGTGTCAAAAAAACTAG
```

FIG. 2D6

FIG. 4A

Avr II (6753)
Bcl I (6738)
SV40 PolyA
Hpa I
Mun I (6589)
Hind III
Kpn I
BamH I (6456)
Bst XI (6437)
EcoR I (6425)
Msc I (6272)
Avr II (6230)
Tth 111I (5783)
Alw NI (5702)
Bbs I (5672)
Mun I (5526)
TAstV Capsid Gene
Fsp I (5046)
Apa LI (4830)
Bst XI (4802)
Apa LI (4670)
Bcl I (4255)
Bbs I (4133)
Tth 111I (4112)
EcoR I (4067)
Pst I
EcoR I (4049)
BamH I (4042)
Ava I (4038)
Polh Promotor
Bst 1107I
Sna BI
Bbs I (3758)
Apa LI (3719)

7112 bp
pFastBac/TAstV-2 capsid

Tn7L
Apa LI (705)
Pvu I
Ampiccillin R
Fsp I (1154)
Ori
Alw NI (1856)
Apa LI (1951)
Sap I
Tn7 R
Msc I (2710)
Bst XI (2718)
Eco RV
Ava I (3133)
Esp 3I
Tth 111I (3229)
Gentamincin R
Ava I (3397)

METHOD TO DETECT ANTIBODIES SPECIFIC FOR TYPE-2 TURKEY ASTROVIRUS

BACKGROUND OF THE INVENTION

Acute gastroenteritis is one of the world's most significant disease problems. An estimated 3 to 5 million people die each year from gastroenteritis, mostly in the developing world (Glass et al., 2001). In the United States, viral gastroenteritis is one of the most common acute illnesses, second only to viral respiratory diseases (Glass et al., 2001). Although several viruses cause gastroenteritis, the most clinically relevant include rotaviruses, caliciviruses, astroviruses, and enteric adenoviruses (Cukor et al., 1984).

Viral gastroenteritis occurs in both an endemic and epidemic fashion, based on the routes of transmission and host response. The most common endemic viruses are group A rotaviruses, enteric adenoviruses, astroviruses and the Sapporo-like viruses (caliciviruses) (Glass et al., 2001). These infections are virtually universal in the first years of life. It is believed that during early childhood, immunity develops to these agents providing protection against recurring infection and explaining the decrease in cases in older children and adults (Kurtz et al., 1978; Kurtz et al., 1979; Mitchell, 2002). Epidemic viruses are best characterized by the Norwalk-like viruses (calicivirus) and the group B rotaviruses. These viruses affect people of all ages, and outbreaks are typically linked to contaminated water and/or food (Goodgame, 2001).

Astroviruses, small round, non-enveloped viruses, typically 28-30 nm in diameter, are implicated in epidemics, usually associated with an institutional setting like a hospital, retirement community, or military base, and they have been isolated from shellfish linked to food borne disease (Matsui et al., 2001). Astroviruses have been reported to cause acute disease in the young of multiple species, including humans, cattle, sheep, cats, dogs, deer, chickens, turkeys, and ducks (Bridger, 1980; Gough et al., 1984; Harboav et al., 1987; Madeley et al., 1975; McNulty et al., 1988; Snodgrass et al., 1977; Tzipon et al., 1981; Williams, 1980; Woode et al., 1978), and multiple serotypes have been described for human, bovine, and turkey astroviruses.

Astroviruses are commonly recognized as a problem in turkeys. Turkey astrovirus (TAstV) was first described by McNulty et al. (1980) in poults in the United Kingdom suffering from diarrhea and increased mortality. In the United States, TAstV was first identified in the 1980s (TAstV-1), and shown to be widely distributed (Reynolds et al., 1986; Reynolds et al., 1987b; Saif et al., 1985). Reynolds et al. (1987b) demonstrated that astroviruses could be isolated from 78% of diseased turkey flocks, more than any other virus identified. TAstV is generally associated with self-limiting mild enteritis, transient growth depression, moderate increases in mortality (Jonassen et al., 2003; Koci et al., 2000; McNulty et al., 1980; Reynolds, 1991; Reynolds et al., 1987b; Yu et al., 2000) and malabsorption (Reynolds et al., 1986; Reynolds et al., 1987a; Thouvenelle et al., 1995a; Thouvenelle et al., 1995b).

Recently, a TAstV isolate, TAsV-2, that is associated with poult enteritis and mortality syndrome (PEMS), was characterized (Koci et al., 2000). PEMS is a multifactorial, highly infectious emerging disease that affects young turkeys, typically between 7 and 28 days of age. The disease was first described in 1991 in an area along the western North Carolina/South Carolina border (Barnes et al., 1997). A PEMS-like disease has been described in most turkey producing states across the United States (Barnes et al., 1997; Brandenberger, 1999), and has been estimated to cost the turkey industry over $100 million (Brandenberger, 1999). TAstV-2 is genetically and immunologically distinct from previously described isolates (Koci et al., 2000).

Strict containment is the only known method of preventing and controlling infections with any of the known astroviruses. Infected flocks, especially those that exhibit severe loss in viability and production, need to be treated with the utmost concern for biosecurity, strictly adhering to the principles discussed in Zander & Mallinson (1991). Astroviruses are extremely stable in the environment and resistant to inactivation by most routinely used disinfectants (Kurtz et al., 1980; Abad et al., 1997; Schultz-Cherry et al., 2001) similar to chicken anemia virus or foot-and-mouth disease virus. For instance, partially purified TAstV-2 remains infectious following treatment with a panel of commercial disinfectants, including 10% bleach. TAstV-2 is also very heat stable, resisting inactivation following treatment at 60° C. for 10 minutes, and resistant to low pH (Schultz-Cherry et al., 2001). These findings suggest that, once a poultry production facility has been infected with astrovirus, complete sanitation of all materials and restricted access to facilities by personnel is required to contain the outbreak to an affected farm.

The combination of age susceptibility and highly stable virions suggests that multiple age farms may help prolong the period of poor production as older birds may recover and no longer exhibit clinical signs but still harbor virus. For example, new poults routinely develop enteritis soon after being placed in "cleaned" houses on farms with multiple aged birds (Edens & Doerfler, 1999). The most practical prevention method is to use strict biosecurity prophylactically. A nominal investment of time and energy spent on keeping each farm pathogen-free could greatly reduce the likelihood of contracting an astrovirus infection, and likewise periods of prolonged poor production.

Until recently the most common method to identify astrovirus infection in birds was electronmicroscopy (EM) (Reynolds, 1991). However, only 10% of particles may exhibit the 5- or 6-pointed starlike morphology making it difficult to accurately identify astroviruses using direct EM, especially when there are very few viral particles present (Caul & Appleton, 1982; Reynolds, 1991; Matsui & Greenberg, 2001). Because of this limitation, Reynolds (1991) suggested using immune EM (IEM) to encourage viral aggregation, however, the addition of purified antibody or convalescent sera to a virus sample can actually mask characteristic physical features or fail to detect new serotypes (Matsui & Greenberg, 2001).

Currently, the one diagnostic tool available for TAstV-2 is a reverse transcriptase-polymerase chain reaction (RT-PCR) assay (Koci et al., 2000). However, such assays require ongoing infection, and the results can be greatly affected by sampling methods. In addition, RT-PCR requires diagnostic facilities capable of performing molecular biology techniques, something many state diagnostic laboratories lack.

Thus, what is needed is an improved method to detect an animal exposed to an astrovirus, e.g., TAsV-2.

SUMMARY OF THE INVENTION

The invention provides a method to identify an animal, e.g., an avian, including but not limited to turkeys, chickens, ostrich, game birds and water fowl such as ducks and geese, or a mammal, e.g., including but not limited to a human, bovine, equine, porcine, feline, canine, caprine and ovine, exposed to turkey astrovirus-2 (TAsV-2). In one embodiment, a physiological fluid sample, such as a serum, bile, or sputum sample, from an animal suspected of being or having been infected with turkey astrovirus-2, is contacted with an antigen of turkey astrovirus-2, and the presence or amount of turkey astrovirus-2 specific antibodies in the sample detected or determined. As used herein, an "antigen" is a sequence in a peptide or polypeptide and optionally highly related sequences, e.g., those having at least 90% amino acid sequence identity, which is specifically bound by antibodies present in physiological fluids of turkey astrovirus-2 infected animals, and is immunogenic, i.e., capable of eliciting the production of specific antibodies in an animal to which the peptide or polypeptide is administered. As used herein, "turkey astrovirus-2" is an astrovirus which is associated with diarrhea or enteritis in young turkey flocks (<about 4 weeks in age) and/or PEMS, and causes diarrhea, growth depression and/or a reduction in thymic mass in susceptible animals, has at least about 80%, and preferably at least about 90%, nucleic acid sequence identity with at least 200, preferably at least 1,000, and up to at least 2,000 to 3,000 or more, e.g., up to about 8,000, contiguous nucleotides of SEQ ID NO:6, an open reading frame thereof, or the complement thereof, encodes a protein that shares at least about 60%, preferably at least 80%, and more preferably at least about 90%, contiguous amino acid sequence identity with at least 150, preferably at least 500, contiguous amino acid residues of, and up to the full-length of, one of SEQ ID NO:7 (encoded by SEQ ID NO:26), SEQ ID NO:8 (encoded by SEQ ID NO:27), or SEQ ID NO:9 (encoded by SEQ ID NO:28), and/or binds antibodies specific for residues 32 to 47, 194 to 221 or 676 to 691 of SEQ ID NO:9, or the corresponding residues in a capsid protein encoded by any one of SEQ ID NOs:10-14. In one embodiment, turkey astrovirus-2 is an astrovirus which is associated with PEMS, causes diarrhea, growth depression and/or a reduction in thymic mass in susceptible animals, and has at least 60% amino acid sequence identity to SEQ ID NO:9 and optionally binds antibodies specific for residues 32-47, 194-221 or 676-691 or SEQ ID NO:9.

The antigen employed in the method may be an isolated antigen, e.g., one which is separated from at least one contaminant with which is it ordinarily associated in its source, as a result of a process that removes the contaminant, thereby increasing the percent of the antigen. For instance, the antigen may be isolated from virus, an in vitro transcription/translation mixture or recombinant cells which express the antigen. In another embodiment, the sample is contacted with recombinant cells which express the antigen, or a lysate thereof. In one embodiment, the recombinant cells are live cells. In another embodiment, the recombinant cells are fixed, e.g., using paraformaldehyde, formalin, methanol, methanol:acetone or ethanol. The recombinant cells may be prepared by introducing, e.g., by transfection or infection, to a host cell, for instance, a prokaryotic or eukaryotic host cell, an expression vector comprising an expression cassette which encodes an antigen of turkey astrovirus-2. In one embodiment, the expression cassette encodes a turkey astrovirus-2 capsid protein or an antigenic portion thereof. The expression vector may encode a fusion protein, e.g., a fusion of a capsid protein or an antigenic portion thereof and another peptide or polypeptide, such as one which anchors the capsid on the outside of the cell membrane of the recombinant host cell, is a secretory sequence or is a purification tag. In one embodiment, the presence of turkey astrovirus-2 specific antibodies in physiological fluid is detected by immunofluorescence or immunohistochemistry, e.g., using an antibody comprising a label, such as a fluorescent molecule or enzyme, which binds turkey antibodies.

As described herein, a recombinant baculovirus (rAcNPV-TAstV-2), which expresses the capsid (outer coat) gene of turkey astrovirus-2 when replicating in insect cells, was prepared. The rAcNPV-TAstV-2 infected cells expressed levels of turkey astrovirus-2 capsid protein (primarily in the cytoplasm of infected cells), which were readily and reproducibly detected using fluorescent antibody or colorimetric techniques. Using monolayers of infected cells, the presence of turkey astrovirus-2 antibodies in serum from experimentally infected turkeys as well as serum isolated from commercial turkey flocks was detected. The present serological assay which employs monolayers of infected cells to detect turkey astrovirus-2 antibodies provided more reproducible results than an assay which employed a crude (unpurified) in vitro transcription/translation mixture for turkey astrovirus-2 capsid to detect an immune response in turkeys experimentally infected with turkey astrovirus-2. Antibodies to turkey astrovirus-2 (for instance, convalescent serum or isolated anti-turkey astrovirus capsid peptide antibodies) may serve as a positive control and non-specific turkey antiserum as a negative control. As turkeys are commonly infected with astrovirus within 2 weeks of birth, physiological fluid may be tested for antibodies to astrovirus, and optionally other pathogens, at 3-4 weeks after birth, and monitored at later times as well, since reinfection is common. In addition, as other animals, for instance chickens or cows, may be carriers of astrovirus, the assay may be employed with samples from animals that are not susceptible to turkey astrovirus-2 associated disease.

The assay utilizes tools and techniques which are widely used in state diagnostic facilities, allows for more routine surveillance of flocks, and does not require the presence of virus. Moreover, the assay can be performed in a 96-well plate format for large-scale testing and the results are available within several hours. This is critical when decisions on condemnation must be made quickly. The assay is the only specific serologic test available for turkey astrovirus, and is likely more sensitive than a RT-PCR assay (Koci et al., 2000) and more specific and sensitive than a commonly used non-astrovirus-specific test (Purdue Diagnostic Laboratory), which requires the isolation of intestines from suspicious birds, is labor intensive, and cannot rapidly be performed at many facilities.

Thus, the invention provides a method to detect or determine exposure of an animal to turkey astrovirus-2. The method includes providing one or more physiological fluid samples from one or more animals suspected of being exposed to turkey astrovirus-2. The one or more samples is contacted with an antigen of turkey astrovirus-2 and then it is detected or determined whether the one or more samples comprise antibodies specific for turkey astrovirus-2, thereby detecting or determining whether the animal was exposed to turkey astrovirus-2.

Also provided is a method to detect antibodies to turkey astrovirus-2 in a physiological fluid sample from an animal. The method includes contacting one or more physiological fluid samples from one or more animals with an antigen of turkey astrovirus-2, and detecting or determining the presence or amount of antibodies specific for turkey astrovirus-2 in the one or more samples.

The invention also provides an isolated nucleic acid molecule (polynucleotide) encoding at least one turkey astrovirus-2 protein or a portion thereof, or the complement of the nucleic acid molecule, wherein the nucleic acid molecule is not SEQ ID NO:6 or the complement thereof. In one embodiment, the isolated nucleic acid molecule comprises any one of SEQ ID NOs: 10-18 and 20-25, or the complement thereof, or encodes a protein or a portion thereof having substantially the same activity as a corresponding polypeptide encoded by one of SEQ ID NOs:10-18 and 20-25. As used herein, "substantially the same activity" includes an activity that is about 10%, 30%, 50%, 90%, e.g., up to 100% or more, the activity of the corresponding full-length polypeptide. In one embodiment, the isolated nucleic acid molecule encodes a polypeptide which is substantially the same as, e.g., having at least 60% or more, e.g., 80%, 90%, 92%, 95%, 97% or 99%, contiguous amino acid sequence identity to, a polypeptide encoded by one of SEQ ID NOs:10-18 and 20-25 but which polypeptide is not any one of SEQ ID NOs:7-9. In one embodiment, the isolated nucleic acid molecule comprises a nucleotide sequence which is substantially the same as, e.g., having at least 80% or 90%, or more, contiguous nucleic acid sequence identity to, one of SEQ ID NOs: 10-18 and 20-25, or the complement thereof, but which is not SEQ ID NO:6 or the complement thereof, and, in one embodiment, also encodes a polypeptide having at least 60%, e.g., 80%, 90%, 92%, 95%, 97% or 99%, contiguous amino acid sequence identity to a polypeptide encoded by one of SEQ ID NOs: 10-18 and 20-25 but which is not any one of SEQ ID NOs:7-9. In one embodiment, the isolated and/or purified nucleic acid molecule encodes a polypeptide with one or more, for instance, 2, 5, 10, 15, 20 or more, conservative amino acids substitutions relative to a polypeptide encoded by one of SEQ ID NOs: 10-18 and 20-25. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. Preferred conservative amino acid substitution groups are: valine-leucine-isoleucine; phenylalanine-tyrosine; lysine-arginine; alanine-valine; glutamic-aspartic; and asparagine-glutamine. The nucleic acid molecule of the invention may be employed to express turkey astrovirus-2 proteins, to prepare chimeric genes, e.g., with other viral genes, and/or to prepare recombinant virus. Thus, the invention also provides vectors, isolated polypeptides, recombinant virus, and host cells contacted with the nucleic acid molecules, vectors or recombinant virus of the invention.

Further provided is a kit for the diagnosis of turkey astrovirus-2 infection. In one embodiment, the kit comprises a substrate and isolated antigen of turkey astrovirus-2, e.g., one encoded by SEQ ID NO:6. In another embodiment, the kit comprises a substrate and recombinant cells which express an antigen of turkey astrovirus-2, e.g., a capsid protein or an antigenic portion thereof. Optionally, the kit includes a positive control, a negative control, diluent, an anti-avian antibody comprising a label, or any combination thereof. In one embodiment, the recombinant cells are fixed in the wells of a tissue culture plate, e.g., a 96-well plate.

Further provided is an immunogenic composition comprising an effective (immunogenic) amount of an antigen of turkey astrovirus-2, e.g., capsid protein. In particular, the antigen may be isolated from recombinant cells which express the antigen. In another embodiment, the immunogenic composition comprises recombinant cells which express an immunogenic amount of the antigen. In one embodiment, the antigen is the capsid protein, and when expressed in a recombinant cell, forms a structure found in an infected cell or virion, i.e., the antigen is full-length and optionally processed to 50 kDa and 30 kDa proteins from a 80 kDa precursor. Optionally, the composition further comprises an effective amount of an immunological adjuvant. The composition, once administered to an animal, e.g., a turkey hen, yields anti-turkey astrovirus-2 antibodies which preferably inhibit or prevent turkey astrovirus-2 infection, enteritis associated with turkey astrovirus-2 infection, and/or PEMS. Such antibodies may be useful for passive immunization. Thus, the invention also provides a method of inducing an immune response in an animal to an antigen of turkey astrovirus-2. The method includes administering to the animal an effective amount of a composition comprising an antigen of turkey astrovirus-2. The composition may be administered orally, mucosally or by subcutaneous or intramuscular injection.

BRIEF DESCRIPTION OF THE FIGURES

FIG. 1. Turkey astrovirus genome structure.

FIG. 2A. Nucleotide sequence of (SEQ ID NO:6), and inferred amino acid sequences encoded by (SEQ ID NOs:7, 8 and 9), one isolate of turkey astrovirus-2.

FIG. 2B. Nucleotide sequence of the capsid gene from exemplary turkey astrovirus-2 isolates (SEQ ID NOs:10-14 and 28).

FIG. 2C. An alignment of six turkey astrovirus-2 capsid genes (SEQ ID NOs:10-14 and 28) and a consensus sequence (SEQ ID NO:25).

FIG. 2D. Nucleotide sequence of ORF1a (SEQ ID NOs: 22-24) and ORF1b (SEQ ID NOs:15-18 and 20-21) from exemplary turkey astrovirus-2 isolates.

FIG. 3. TAsV-2 IgG and IgA responses following infection.

FIG. 4. Vectors for TAsV-2 protein expression in insect cells.

DETAILED DESCRIPTION OF THE INVENTION

Enteric disease is a common problem in young turkeys, resulting in substantial financial losses to the poultry industry. Unfortunately, the effects of enteric disease continue long after clinical recovery and can influence the life quality and value of the flocks. Many different viruses are known to cause enteric disease including retrovirus, coronavirus, enterovirus, and astrovirus. Astroviruses are involved in enteritis in young turkeys due to infection early in life, e.g., at weeks 2 and 3, and the presence of astrovirus increases the probability that a flock will develop PEMS and suffer from severe mortality, resulting in serious financial losses. Testing for astrovirus has become a common way to monitor young turkey flocks. The outcome of the test can determine the fate of a flock (i.e., if the flock is turkey astrovirus-2-positive at a young age, it will commonly be condemned rather than face the losses). Additionally, environmental testing of poultry houses and water for turkey astrovirus-2 is becoming more common given the stability and potential zoonotic transmission of the virus.

I. Astrovirus Genome Organization and Molecular Characterization

Astroviruses are small RNA viruses that are incredibly stable in the environment and resistant to many commercial disinfectants. Astroviruses contain a single stranded positive sense RNA genome typically 7-8 kb in length (Lukashov et al., 2002). The complete sequence of five human astroviruses (HAstVs) isolates (Jiang et al., 1993; Lewis et al., 1994; Willcocks et al., 1994) (GenBank accession AF141381, AF260508), two turkey isolates (Jonassen et al., 1998; Koci et al., 2000b), avian nephritis virus (ANV) (Imada et al., 2000), a sheep astrovirus (OAstV) (Jonassen et al., 1998), and a mink astrovirus (Englund et al., 2002) are available in GenBank.

The basic organization and replication strategy is conserved among all of the astroviruses sequenced. The astrovirus genome includes a 5' untranslated region (UTR), followed by three open reading frames (ORFs), a 3' UTR, and a poly-A tail (FIG. 1). The 3 ORFs are designated ORF1a, ORF1b, and ORF2 (Willcocks et al., 1994). The 5' reading frame, ORF1a, is predicted to encode nonstructural proteins including a viral serine protease likely important in processing and maturation of each of the polyproteins encoded in this first reading frame (Willcocks et al., 1994; Geigenmuller et al., 2002; Gibson et al., 1998; Kiang et al., 2002; Willcocks et al., 1999). This viral protease is similar to chymotrypsin-like proteases of other positive sense RNA viruses, although it differs in that a serine residue has been substituted for a cysteine in the third catalytic position (Gorbalenya et al., 1989; Matsui & Greenberg, 2001). Alignments of the 3 avian AstVs (AAstVs) ORF1a predicted amino acid (aa) sequences allowed for identification of a putative serine protease. When compared to the mammalian AstV (MAstV) serine protease sequence, the three predicted catalytic residues can be identified and are conserved. For instance, the serine residues do align, as well as many of the residues predicted to be important in substrate binding. There is a one-residue shift of the second catalytic aa (aspartic acid) between the AAstVs and the MAstVs.

Downstream of the serine protease, ORF1a is believed to encode a nuclear localization signal (NLS). This putative NLS is 664 aa from the N-terminus of the ORF1a polyprotein of HAstV1 (Willcocks et al., 1999). The need or function of an NLS in an RNA virus is still unclear, but several investigators described limited nuclear staining for astrovirus antigen (Aroonprasert et al., 1989; Willcocks et al., 1999). A similar motif was identified for ANV, corresponding to aa positions 719-735 (Imada et al., 2000). Similar aa sequences can be found in both turkey astrovirus (TAstVs), but none of the putative AAstV NLSs have been tested experimentally. Examination of HAstV ORF1a identified 4 potential transmembrane helical motifs, a putative bipartite nuclear localization signal (NLS), and a region referred to as the immune response element (IRE) identified by antiserum produced against purified particles (Gibson et al., 1998; Willcocks et al., 1999).

The overall ORF1a sequence similarities between the AAstVs and the MAstVs is quite low ranging from 20-25% nucleotide identity (12-15% amino acid identity). However, it is the presence of astrovirus-like nonstructural motifs that is most important. ORF1a is also the most conserved among the HAstVs, and has been used to define two distinct genogroups (Belliot et al., 1997). This is not the case for the AAstVs sequenced to date. There is a greater relatedness among the HAstVs, and to lesser extent sheep astrovirus (OAstVs), than among AAstVs. This suggests AAstV nonstructural proteins are allowed greater flexibility in sequence variation than their mammalian counterparts. This may be related to differences in host range (Schneider & Roossinck, 2001). There is no evidence that the MAstVs cross species lines (Matsui & Greenberg, 2001). However, based on surveillance studies of chicken and turkey farms, antibodies against ANV were isolated from both chickens and turkeys suggesting either support ANV replication (Nicholas et al., 1988; Cavanagh, 1992). Having greater genetic flexibility may increase the likelihood of replicating in whatever poultry species is available, so long as the overall functional motif is conserved (Schneider & Roossinck, 2001).

The first start codon of ORF1b for the HAstVs is found more than 400 nt inside the reading frame, in a suboptimal position according to Kozak's rules (Matsui & Greenberg, 2001). The ORF1a/ORF1b overlap region contains a heptameric shift sequence (A AAA AAC) and the potential for the formation of a downstream stem-loop and possible pseudoknot that would provide a ribosomal frameshift mechanism (Willcocks et al., 1994; Lewis & Matsui, 1995; Lewis & Matsui, 1996; Imada et al., 2000; Koci et al., 2000b). This mechanism is similar to that used by retroviruses and coronaviruses, however, unlike those viruses, the pseudoknot is not required for the astrovirus frameshift to occur (Lewis & Matsui, 1997). This heptameric sequence, and predicted secondary structure has been identified in all three avian AstVs. It is believed that this frameshift structure allows for the translation of ORF1a and ORF1b to occur as one polyprotein that is then cleaved into functional subunits. Analysis of ORF1b, indicates that it encodes for an RNA dependent RNA polymerase (RdRp) (Poch et al., 1989; Ishihama & Barbier, 1994; Lewis et al., 1994; Marczinke et al., 1994). This region of the astrovirus genome is the most conserved between the MAstVs and the AAstVs, as well as among the AAstVs. The RNA-dependent RNA polymerase is liberated from the polyprotein by the serine protease from ORF1a (Lewis et al., 1998).

The final ORF, ORF2, encodes the viral structural protein (Carter et al., 1996). This region encodes a precursor protein with a mass between 75 kilodalton (kDa) and 90 kDa (depending on species) (Jonassen et al., 2001; Wang et al., 2001). The intracellular processing of this sole structural precursor is not well understood (Bass et al., 2000; Menandez et al., 2002). ORF2 is transcribed into a subgenomic message, which is one of the key features, along with the ribosomal frameshift in ORF1a, which led to the classification of astroviruses into their own family.

The lengths of each of these features vary between species and serotypes. For instance, among the three AAstVs there is some variation in the overall lengths of the genomes and their respective internal components (Table 1; FIG. 1). In addition to variation in ORF lengths, there are also differences in the expression strategies for ORF2. Most MAstVs (with the exception of HAstV-8) have an overlap of approximately 8 nucleotides (nt) between the stop codon of ORF1b and the start codon of ORF2, which is in the same reading frame as ORF1a. However, the AAstVs deviate from this somewhat in their genome structure. The start codon for ORF2 of ANV is 19 nt downstream of the stop codon of ORF1b, though ORF2 is still in the same frame as ORF1a (FIG. 1). The space between the ORF1b stop codon and ORF2 start site for both TAstVs is 18 nt (FIG. 1), placing the TAstV ORF2 in the same frame as ORF1b (FIG. 1). There are also some differences among the AAstVs toward the end of the genome. Sequence analysis of the last 19 nt of ORF2 and adjacent 3' UTR by (Jonassen et al., 1998; Jonassen et al., 2001) described a conserved sequence and predicted secondary structure present in all astrovirus isolates sequenced, except for TAstV-2 (FIG. 1). This conserved motif is also present in infectious bronchitis virus (a coronavirus) and equine rhinovirus type 2 (a picornavirus) (Jonassen et al., 1998).

TABLE 1

Comparison of the nucleotide lengths of the AAstV genome regions.

| Avian astrovirus | Number of nucleotides in | | | | | |
|---|---|---|---|---|---|---|
| | 5' UTR | ORF 1a | ORF 1b | ORF 2 | 3' UTR | Total[a] |
| ANV | 14 | 3012 | 1527 | 2052 | 305 | 6927 |
| TAstV-2 | 21 | 3378 | 1584 | 2175 | 196 | 7325 |
| TAstV-1 | 11 | 3300 | 1539 | 2016 | 130 | 7003nt |

[a]excluding the poly-A tail

II. Immune Response to Astrovirus Infection

Both B cells and T cells respond to human astrovirus infection, and virus-neutralizing antibodies are considered key to astrovirus resistance in humans. Human volunteer studies demonstrated that those with pre-existing antibody titers did not show signs of astrovirus disease. The protective role of virus-specific antibodies has also been demonstrated therapeutically as intravenous immunoglobulin therapy has been used to treat persistent astrovirus infections in immune compromised patients. Astrovirus infections are typically associated with immature or infirmed immune systems. In these hosts, the role of humoral and cellular immunity is hindered or non-existent, however, astroviruses seldom establish persistent infections.

Figure 3:
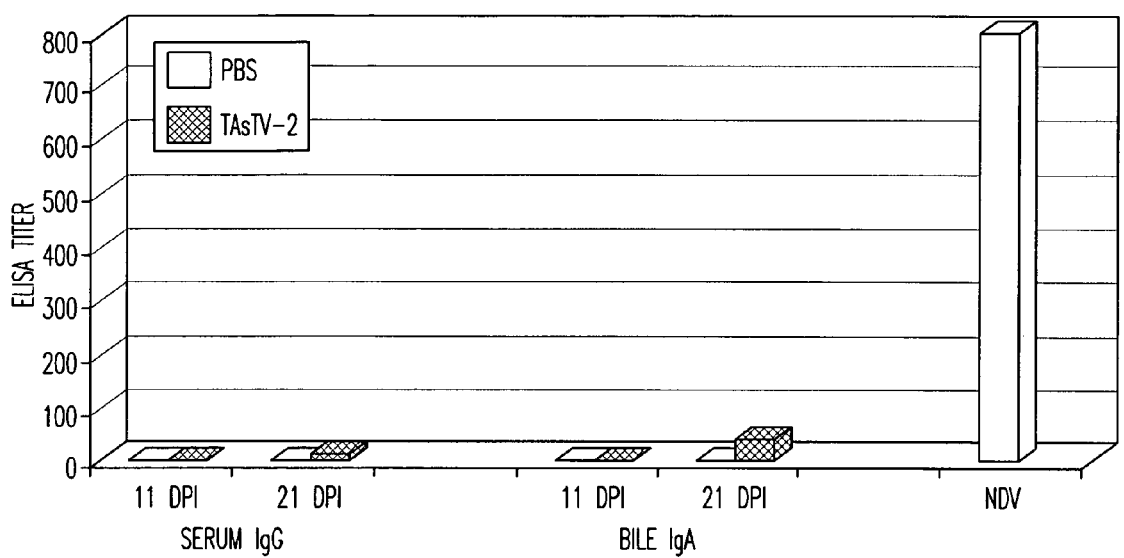
Figure 4B:
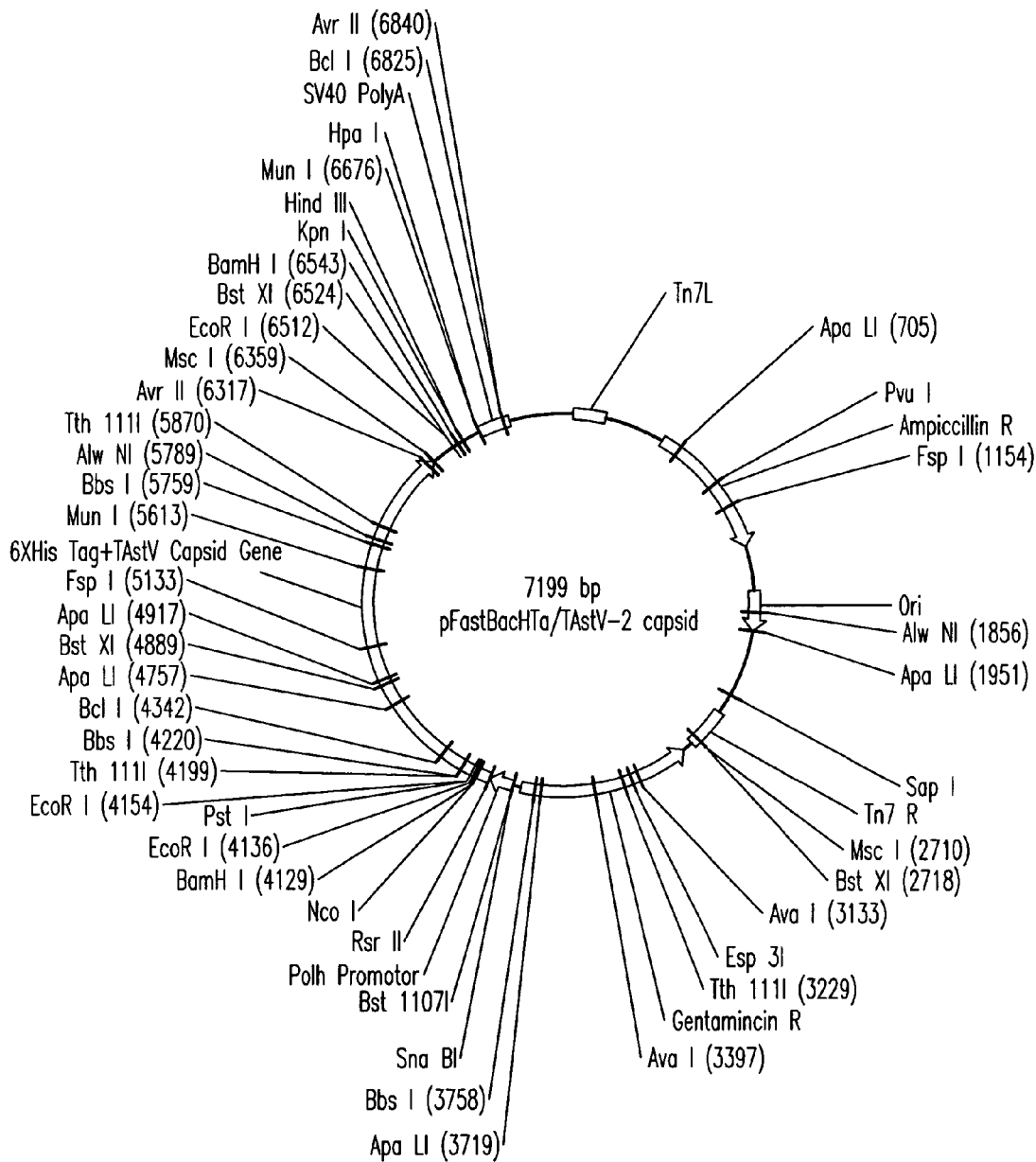
Figure 4C:
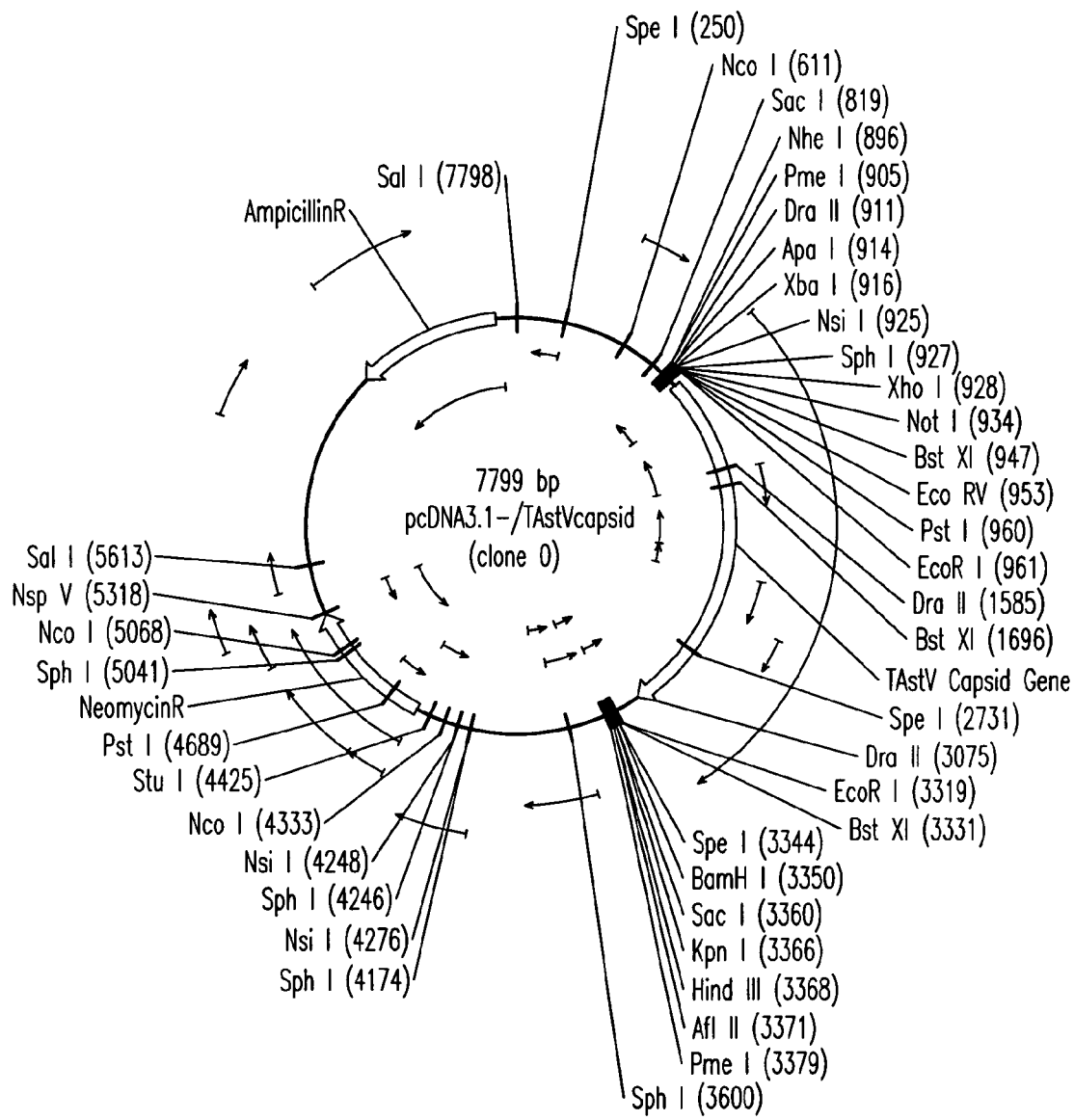

Serial dilutions of sera and bile isolated at 11 and 21 days post-infection of turkey poults with turkey astrovirus-2 were incubated with a crude in vitro transcription/translation mixture of turkey astrovirus-2 capsid prepared using pcDNA3.1⁻ as the expression vector (pcDNA3.1⁻/TAsV-cap10). In particular, microtiter plates with the capsid mixture were contacted with sera or bile, and IgG and IgA detected using alkaline phosphatase conjugated goat anti-chicken IgG or IgA (FIG. 3; ELISA titers are reported as the reciprocal of the dilution factor). In contrast to humans, there is little evidence of an adaptive immune response following astrovirus infection in otherwise healthy turkeys (FIG. 3). The lack of acquired immunity to turkey astrovirus-2 infection suggests the turkey model may reflect the host response in a non-competent immune host.

III. Serological Assay to Detect TAsV-2 Infection

The present invention provides a serologic test for astrovirus infection, e.g., turkey astrovirus-2. This test is specific to astrovirus, easy to adapt if the virus evolves, expandable to different types of enteric viruses, rapid, and can be used by any diagnostic laboratory such as those performing immunofluorescence or immunohistochemistry. Finally, because the test detects antibodies, there is no risk of missing the window of opportunity needed to detect virus using nucleic acid-based amplification strategies.

The invention employs an antigen of turkey astrovirus-2. In one embodiment, the antigen is provided in the form of recombinant cells transformed with an expression vector encoding one or more antigens of turkey astrovirus-2. In another embodiment, the antigen is provided as isolated turkey astrovirus-2 antigen, e.g., antigen isolated from virus, an in vitro transcription/translation reaction or a recombinant cell comprising an expression vector encoding one or more turkey astrovirus-2 antigens.

A. Preparation of Expression Cassettes and Recombinant Host Cells

Sources of nucleotide sequences from which the present nucleic acid molecules encoding an antigen of turkey astrovirus-2, or the nucleic acid complement thereof, include RNA or cDNA from any isolate of turkey astrovirus-2, e.g., from physiological fluid or tissue of an animal infected with turkey astrovirus-2, preferably an infected avian. Other sources of the DNA molecules of the invention include cDNA libraries derived from any turkey astrovirus-2-infected cellular source.

A nucleic acid molecule encoding an antigen of turkey astrovirus-2 can be identified and isolated using standard methods, as described by Sambrook et al., (1989). For example, reverse-transcriptase PCR (RT-PCR) can be employed to isolate and clone turkey astrovirus-2 cDNAs. A primer which is complementary to the RNA encoding a turkey astrovirus-2, and preferably hybridizes to the 3' two-thirds of the RNA can be employed as a primer in a reverse transcriptase reaction to prepare first-strand cDNAs from isolated RNA which contains RNA sequences of interest, e.g., total RNA isolated from an infected avian tissue. RNA can be isolated by methods known to the art, e.g., using TRIZOL™ reagent (Invitrogen). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7-8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al. (1987); Erlich, (1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other astrovirus genes. One primer is prepared which is predicted to anneal to the antisense strand, and another primer prepared which is predicted to anneal to the sense strand, of a DNA molecule which encodes an antigen of turkey astrovirus-2.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs. Alternatively, the gel-purified fragment can be directly sequenced.

As used herein, the terms "isolated and/or purified" refer to in vitro isolation of a nucleic acid molecule or polypeptide molecule from its natural cellular environment, and from association with other components of the cell, such as nucleic acid or polypeptide. For example, "isolated turkey astrovirus-2 nucleic acid" is RNA or DNA containing greater than 9, preferably 36, and more preferably 45 or more, sequential nucleotide bases that encode at least a portion of a protein of turkey astrovirus-2, or a RNA or DNA complementary thereto, that is complementary or hybridizes, respectively, to RNA or DNA encoding a protein of turkey astrovirus-2 and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other RNA or DNA. The phrase "free from at least one contaminating source nucleic acid with which it is normally associated" includes the case where the nucleic acid is reintroduced into the source or natural cell but is in a different location or is otherwise flanked by nucleic acid sequences not normally found in the source. An example of isolated turkey astrovirus-2 nucleic acid is RNA or DNA that shares at least about 80%, and more preferably at least about 90%, nucleic acid sequence identity with at least 15 contiguous nucleotides of SEQ ID NO:6, any one of SEQ ID NOs:10-18 and 20-28, or the complement thereof, or at least about 80% nucleic acid sequence identity with at least 200 and up to 1,500, e.g., up to 3,000, or more nucleotides of SEQ ID NO:6, an open reading frame therein, any one of SEQ ID NOs:10-18 and 20-28, or the complement thereof, or encodes a protein that shares at least about 60%, preferably at least about 80%, and more preferably at least about 90%, amino acid sequence identity with at least 15 contiguous residues of SEQ ID NO:7, SEQ ID NO:8, SEQ ID NO:9, or the protein encoded by any one of SEQ ID NOs:10-18 and 20-25, or at least about 60%, preferably at least about 80%, and more preferably at least about 90%, amino acid sequence identity with at least 150 and up to about 500 amino acids or more of, for instance, SEQ ID NO:9 or a protein encoded by any one of SEQ ID NOs:10-14.

As used herein, the term "recombinant nucleic acid" or "recombinant RNA or DNA sequence or segment" refers to a nucleic acid, e.g., to DNA, that has been derived or isolated from any appropriate viral or cellular source, that may be subsequently chemically altered in vitro, so that its sequence is not naturally occurring, or corresponds to naturally occurring sequences that are not positioned as they would be positioned in a genome which has not been transformed with exogenous DNA. An example of DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Therefore, "recombinant DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

Nucleic acid molecules encoding amino acid sequence variants of an antigen of turkey astrovirus-2 are prepared by a variety of methods known in the art. These methods include, but are not limited to, isolation from a natural source (in the case of naturally occurring amino acid sequence variants or serotypes) or preparation by oligo-nucleotide-mediated (or site-directed) mutagenesis, PCR mutagenesis, directed evolution, and cassette mutagenesis of an earlier prepared variant or a non-variant version of an antigen of turkey astrovirus-2.

In one embodiment, the nucleic acid sequence for an antigen of turkey astrovirus-2 is altered to encode a polypeptide or peptide with one or more amino acid substitutions relative to the polypeptide or peptide encoded by the unaltered nucleic acid sequence. Preferably, the altered nucleic acid sequence encodes a polypeptide or peptide that is antigenic, e.g., binds antibodies specific for turkey astrovirus-2. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Conservative substitutions within the scope of the invention include those shown in Table 2 under the heading of exemplary substitutions. More preferred substitutions are under the heading of preferred substitutions. After the substitutions are introduced, the variants are screened for activity, for binding to antibodies specific for turkey astrovirus-2.

TABLE 2

| Original Residue | Exemplary Substitutions | Preferred Substitutions |
|---|---|---|
| Ala (A) | val; leu; ile | Val |
| Arg (R) | lys; gln; asn | Lys |
| Asn (N) | gln; his; lys; arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | asn; gln; lys; arg | Arg |
| Ile (I) | leu; val; met; ala; phe norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala | Leu |
| Pro (P) | Gly | Gly |
| Ser (S) | Thr | Thr |
| Thr (T) | Ser | Ser |
| Trp (W) | Tyr | Tyr |
| Tyr (Y) | trp; phe; thr; ser | Phe |
| Val (V) | ile; leu; met; phe; ala; norleucine | Leu |

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions polypeptide or peptide variants with non-conservative substitutions. Non-conservative substitutions entail exchanging a member of one of the classes described above for another.

Once a particular nucleic acid sequence or molecule is selected, it is introduced into an expression cassette. Expression cassettes may be circular or linear, double-stranded or single-stranded. A DNA sequence which encodes an RNA sequence that is substantially complementary to a RNA sequence encoding an antigen of turkey astrovirus-2 is typically a "sense" DNA sequence cloned into a cassette in the opposite orientation (i.e., 3' to 5' rather than 5' to 3'). Generally, expression cassette is in the form of chimeric DNA that contains a coding region flanked by control sequences for the expression of the DNA sequence, or otherwise serve a regulatory or a structural function. "Chimeric" means that a vector comprises DNA from at least two different species or sources, or comprises DNA from the same species, which is linked or associated in a manner which does not occur in the "native" or wild type of the species (immature). Control sequences are DNA sequences for the expression of an operably linked coding sequence in a particular host cell organism. The control sequences that are suitable for prokaryotic cells, for example, include a promoter, and optionally an operator sequence, and a ribosome binding site. Eukaryotic cells are known to utilize promoters, polyadenylation signals, and enhancers. For example, the expression vector may comprise an expression cassette comprising a promoter that is active in eukaryotic cells operably linked to a coding sequence. Exemplary promoters in eukaryotes include viral promoters such as a CMV promoter, a SV40 late promoter, retroviral LTRs (long terminal repeat elements), and a baculovirus promoter, although many other promoter elements for eukaryotic, as well as prokaryotic cells, which are well known to the art, may be employed in the practice of the invention.

"Operably linked" is defined to mean that nucleic acids are placed in a functional relationship with each other. For example, a promoter or enhancer is operably linked to a coding sequence if it affects the transcription of the sequence; a ribosome binding site is operably linked to a coding sequence if it is positioned so as to facilitate translation; DNA for a presequence or secretory leader is operably linked to DNA for a peptide or polypeptide if it is expressed as a preprotein that participates in the secretion of the peptide or polypeptide; or a DNA for an epitope, purification tag or membrane-spanning domain is operably linked to DNA for a peptide or polypeptide if it is expressed as a fusion protein and facilitates detection, purification or localization of that fusion. Generally, "operably linked" means that the DNA sequences being linked are contiguous and, in the case of a secretory leader, epitope, purification tag or other domain, contiguous and in reading phase. However, enhancers do not have to be contiguous. Linking is often accomplished by ligation at convenient restriction sites. If such sites do not exist, the synthetic oligonucleotide adaptors or linkers are used in accord with conventional practice.

Elements such as introns, enhancers, polyadenylation sequences and the like, may or may not be necessary for the function of the DNA, but may provide improved expression of the DNA sequence by affecting transcription, stability of the mRNA, or the like. Such elements may be included in the expression cassette as desired to obtain the optimal performance of the expression cassette in the cell.

The recombinant DNA containing the expression cassette to be introduced into the cells may also contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Exemplary reporter genes include the chloramphenicol acetyl transferase gene (cat) from Tn9 of E. coli, the beta-glucuronidase gene (gus) of the uidA locus of E. coli, and the luciferase gene, e.g., from the firefly Photinus pyralis. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, Sambrook et al. (1989) provides suitable methods of construction.

A vector comprising a recombinant DNA, for instance, a vector comprising an expression cassette of the invention, can be readily introduced, e.g., transfected or via infection, into host cells, e.g., mammalian, bacterial, e.g., E. coli or Salmonella, fungal, yeast or insect cells, by any procedure useful for the introduction of nucleic acid into a particular cell, e.g., physical or biological methods, to yield a recombinant cell having the recombinant DNA. The host cells of the present invention are typically produced by transfection or infection with a DNA sequence in a plasmid expression vector, a viral expression vector, or as an isolated linear DNA sequence. The host cell is preferably of insect origin, but cell lines or host cells of non-insect origin may be employed, including avian, plant, mammalian, yeast, fungal or bacterial sources.

Physical methods to introduce a recombinant DNA into a host cell include calcium phosphate precipitation, lipofection, particle bombardment, microinjection, electroporation, and the like. Biological methods to introduce the DNA of interest into a host cell include the use of DNA and RNA viral vectors. Viral vectors can be derived from poxviruses, herpes simplex virus I, retroviruses, baculoviruses, adenoviruses and adeno-associated viruses, and the like.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; or "biochemical" assays, such as detecting the presence or absence of a turkey astrovirus-2 polypeptide, e.g., by immunological means (ELISAs, immunofluorescence, immunohistochemistry, and Western blots).

B. Isolated Antigen

Sources of antigen useful in the methods of the invention include turkey astrovirus-2 virions or degradation products thereof, turkey astrovirus-2 peptide or polypeptide products of an in vitro reaction such as a chemical synthesis or an in vitro transcription/translation mixture, and recombinant cells expressing one or more turkey astrovirus-2 peptides or polypeptides, or antigenic portions thereof. An antigenic "portion" is generally an amino acid sequence of at least about five consecutive amino acids of a particular peptide or polypeptide but less than the sequence of the full-length peptide or polypeptide. Virus may be propagated in eggs and isolated by known methods. Specific viral proteins in the turkey astrovirus-2 viral preparation may be separated by known techniques, yielding isolated turkey astrovirus-2 protein. Alternatively, turkey astrovirus-2 protein may be obtained synthetically, e.g., via chemical synthesis or recombinant means. As used herein, a turkey astrovirus-2 peptide or polypeptide includes turkey astrovirus-2 peptides or polypeptides having one or more modifications, e.g., insertions, deletions or substitutions, which do not substantially alter the binding of the resulting peptide or polypeptide to anti-turkey astrovirus-2 antibodies found in infected animals relative to the binding of the corresponding non-modified (wild-type) peptide or polypeptide to those antibodies.

Turkey astrovirus-2 peptides or polypeptides can be synthesized in vitro, e.g., by the solid phase peptide synthetic method or by recombinant DNA approaches. When a turkey astrovirus-2 polypeptide of the invention is expressed in a recombinant cell, the polypeptide may be purified from other recombinant cell proteins or polypeptides to obtain preparations that are substantially homogenous as to the turkey astrovirus-2 peptide or polypeptide. For example, the culture medium or lysate can be centrifuged to remove particulate cell debris. The membrane and soluble protein fractions are then separated. The turkey astrovirus-2 polypeptide may then be purified from the soluble protein fraction. Alternatively, the turkey astrovirus-2 polypeptide may be purified from the insoluble fraction, i.e., refractile bodies (see, for example, U.S. Pat. No. 4,518,526), if necessary. Turkey astrovirus-2 peptide or polypeptide may be purified from contaminant soluble or membrane proteins and polypeptides by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75;, or ligand affinity chromatography; ultracentrifugation, and the like.

If expressed as a fusion polypeptide, the fusion polypeptide may be purified by methods specific for the non-turkey astrovirus-2 polypeptide portion of the polypeptide. For example, if the fusion polypeptide is a glutathione-S transferase (GST) fusion polypeptide, GST 4B beads may be employed to purify the fusion polypeptide.

Turkey astrovirus-2 polypeptide or a portion thereof, can also be prepared by in vitro transcription and translation reactions. A turkey astrovirus-2 polypeptide expression cassette can be employed to generate turkey astrovirus-2 gene-specific transcripts which are subsequently translated in vitro so as to result in a preparation of substantially homogenous turkey astrovirus-2 peptide or polypeptide. The construction of vectors for use in vitro transcription/translation reactions, as well as the methodologies for such reactions, are well known to the art.

The solid phase peptide synthetic method is an established and widely used method to prepare peptides and polypeptides, which is described in the following references: Stewart et al., 1969; Merrifield, 1963; Meienhofer, 1973; and Bavaay and Merrifield, 1980). These polypeptides or peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given turkey astrovirus-2 polypeptide or peptide can be readily prepared. For example, amides of the turkey astrovirus-2 polypeptide, peptide or variants thereof of the present invention may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a polypeptide or peptide of the invention may be prepared in the usual manner by contacting the polypeptide or peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the polypeptide or peptide of the invention may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the polypeptide or peptide. Other amino-terminal modifications include aminooxypentane modifications (see Simmons et al., 1997).

In addition, the amino acid sequence of the polypeptide or peptide can be modified as described above and including substitutions which utilize the D rather than L form, as well as other well known amino acid analogs.

Acid addition salts of the polypeptide or peptide or of amino residues of the polypeptide or peptide may be prepared by contacting the polypeptide or peptide, or amine thereof with one or more equivalents of the desired inorganic or organic acid, such as, for example, hydrochloric acid. Esters of carboxyl groups of the polypeptides or peptides may also be prepared by any of the usual methods known in the art.

C. Exemplary Assays

The present invention relates to assays for use in veterinary medicine. In one embodiment, turkey astrovirus-2 antigen is employed to detect or determine the presence or amount of anti-turkey astrovirus-2 antibodies in an animal. In particular, the use of turkey astrovirus-2 antigen with physiological fluid from an animal can detect whether the animal has been exposed to turkey astrovirus-2, i.e., due to the presence of antibodies in physiological fluid which bind to a turkey astrovirus-2 polypeptide or peptide, and so is at risk of infecting other animals or succumbing to viral induced pathology. Animals which have anti-turkey astrovirus-2 antibodies may be at risk of developing or have PEMS, a convalescent animal or a carrier of turkey astrovirus-2.

The invention thus provides a method for detecting or determining the presence antibodies which are specific for turkey astrovirus-2 in an animal physiological fluid sample. The method comprises contacting an amount of antigen (native or recombinant) of turkey astrovirus-2, with the physiological sample which comprises antibodies suspected of specifically reacting with turkey astrovirus-2, for a sufficient time to form binary complexes between at least a portion of the antibodies and the antigen. Then the presence or amount of the complexes is detected or determined. In one embodiment, recombinant cells transfected or infected with nucleic acid encoding an antigen of turkey astrovirus-2, such as a lysate of those cells, can be employed as the antigenic material that is contacted with the physiological sample to be tested. The invention also provides kits useful to detect or determine the presence of antibodies that specifically react with an infectious agent which is associated with PEMS. Such a kit may comprise packaging, containing, separately packaged: (a) cells transfected with turkey astrovirus-2 nucleic acid or infected with turkey astrovirus-2, e.g., cells which are fixed; and (b) a solid phase capable of immobilizing the cells. Such a kit may also comprise packaging, containing, separately packaged: (a) isolated turkey astrovirus-2 antigen, e.g., capsid protein from cells transfected with turkey astrovirus-2 nucleic acid or infected with turkey astrovirus-2; and (b) a solid phase capable of immobilizing the antigen.

Exemplary means for detecting and/or quantitating turkey astrovirus-2 antibody in body fluids, including supernatants from homogenized tissue samples or tissue sample lysates, include affinity chromatography, Western blot analysis, immunoprecipitation analysis, agglutination, hemagglutination as well as immunoassays including but not limited to immunohistochemistry, ELISAs (enzyme-linked immunosorbent assays), RIA (radioimmunoassay), IFA (immunofluorescent assays), competitive EIA or dual antibody sandwich assays. Immunoassays are a preferred means to detect turkey astrovirus-2. The assays can be performed using standard protocols such as those described by Magnarelli et al., 1984; Craft et al., 1984; Enguall et al., 1971; and Russell et al., 1984.

Representative immunoassays involve the use and/or detection of at least one antibody specific for turkey astrovirus-2 in the body fluid of an animal. The moiety employed to detect the antigen bound antibodies may be detectable, e.g., a moiety which is labeled or otherwise capable of detection, e.g., using a molecule which interacts with the moiety. Unlabeled antibodies may be employed in agglutination; labeled antibodies or other binding molecules may be employed in a wide variety of assays, which can employ a wide variety of labels. Suitable detection means include the use of labels such as radionuclides, enzymes, fluorescent molecules, chemiluminescent molecules, enzyme substrates or co-factors, enzyme inhibitors, particles, dyes, beads, e.g., gold beads, and the like. Such labeled reagents may be used in a variety of well known assays. See for example, U.S. Pat. Nos. 3,766,162, 3,791,932, 3,817,837, and 4,233,402. For instance, the detectable moiety may allow visual detection of a precipitate or a color change, visual detection by microscopy, or automated detection by spectrometry, radiometric measurement, or the like. Examples of detectable moieties include fluorescein and rhodamine (for fluorescence microscopy or other fluorometric techniques), horseradish peroxidase (for either light or electron microscopy and biochemical detection), biotin-streptavidin (for light or electron microscopy), alkaline phosphatase (for biochemical detection by color change), and luciferase (for luminescence detection by a luminometer or fluorometric techniques). The detection methods and moieties used can be selected, for example, from the list above, or other suitable examples by the standard criteria applied to such selections (Harlow and Lane, 1988; herein incorporated by reference).

In one embodiment, an assay of the present invention can be constructed by coating on a surface (i.e., a substrate such as solid support), for example, a plastic bead, a microtitration plate, a membrane (e.g., nitrocellulose membrane) or an inert particle, for example, bentonite, polystyrene or latex, an antigen such as turkey astrovirus-2 peptide or polypeptide (natural, recombinant or synthetic), or a recombinant host cell expressing one or more turkey astrovirus-2 peptides or polypepides. The antigen is contacted with serum or other physiological fluid taken from an animal suspected of being exposed to turkey astrovirus-2 or having a turkey astrovirus-2 infection. Following removal of the physiological fluid, any antibody bound to antigen can be detected, for instance, by reacting the binary antibody-antigen complexes with a moiety that binds the antibody, the antigen, or the complex. In one embodiment, the moiety comprises a label (detectable molecule) or binds to a detectable molecule. For example, the moiety may be an antibody comprising a label or a binding site for a detectable molecule. Generally, the secondary antibody is selected for its ability to react with multiple sites on the primary antibody.

In one embodiment, a sample from a test subject is reacted with the antigen bound to a substrate (antigen/antibody complex) (e.g., 96 well plate), and excess sample is washed from away. A labeled monoclonal antibody is then reacted with the previously reacted antigen/antibody complex. The amount of inhibition of monoclonal antibody binding is measured relative to a control. The degree of monoclonal antibody inhibition is a very specific test for a particular variety or strain since it is based on monoclonal antibody binding specificity.

In another embodiment, a sample suspected of comprising antibodies to turkey astrovirus-2 is contacted with a surface and the antigen added to the sample. In one embodiment, the sample is covalently linked to the surface. Following removal of any unbound antigen, antigen bound to the sample can be detected, for instance, by reacting the binary antibody-antigen complexes with a moiety that binds the antibody, antigen or the complex. In one embodiment, the moiety comprises a label or binds to a detectable molecule.

In yet another embodiment, the sample and antigen are mixed, and complexes detected, for instance, by reacting the binary antibody-antigen complexes with a moiety that binds the antibody, the antigen, or the complex, e.g., a moiety which is attached to a support.

A micro-agglutination test can also be used to detect the presence of antibodies to avian astroviruses. Latex beads (or red blood cells) are coated with the antigen and mixed with a sample, such that antibodies in the sample that are specifically reactive with the antigen cross-link with the antigen, causing agglutination. The agglutinated antigen-antibody complexes form a precipitate, visible to the naked eye or capable of being detected by a spectrophotometer. In a modification of the above test, antibodies specifically reactive with the antigen can be bound, the beads and the antigen in the sample thereby detected.

IV. Dosages, Formulations and Routes of Administration of the Host Cells and Polypeptides of the Invention In another embodiment of the invention, turkey astrovirus-2 antigen is employed to elicit a humoral response, e.g., a protective response, in an animal. The antigen of the invention can thus be used in an immunogenic composition comprising an effective amount of the antigen and optionally a pharmaceutically acceptable carrier. The immunogenic composition may include the antigen, or a recombinant host cell which expresses the antigen, e.g., an insect cell or E. coli which expresses the antigen. The immunogenic composition can then be used in a method of reducing and or preventing complications of avian astrovirus infection.

Cells which express one or more turkey astrovirus-2 peptides or polypeptides, or isolated polypeptides or peptides, of the invention are preferably administered to an animal, e.g., a turkey, chicken or bovine, so as to result in an immune response specific for the virus or a related virus. These compounds and compositions can be administered to avians and mammals for veterinary use, such as for use with domestic or farm animals. The recombinant cells compositions may be administered as live, modified-live (attenuated) or inactivated cells, or optionally administered as a combination of attenuated, inactivated, and/or live cells, or in combination with a polypeptide or peptide of the invention, or any combination thereof. Moreover, the administration of more than one immunogenic agent of the invention to an animal may occur simultaneously or at different times. The cells may be inactivated by agents including, but not limited to, formalin, phenol, ultraviolet radiation, and β-propiolactone. In particular, for administration of polypeptide or peptide of the invention, e.g., subcutaneously, in ovo, orally or intramuscularly, to a bird, e.g., turkeys or chickens, the amount administered may be at dosages of at least about 1 μg to about 10 mg, preferably about 10 μg to about 1 mg, and more preferably about 100 μg to about 500 μg, although other dosages may provide beneficial results. For administration of recombinant cells, the amount administered may be at dosages of at least about $10^4$ to about $10^7$ cells, e.g., cells which may be administered subcutaneously, in ovo, orally or intramuscularly, although other dosages may provide beneficial results. Dosages within these ranges can be administered via bolus doses or via a plurality of unit dosage forms, until the desired effects have been obtained. The amount administered will vary depending on various factors including, but not limited to, the specific immunogen chosen, the weight, physical condition and age of the animal, and the route of inoculation. Thus, for peptides and polypeptides, the absolute weight of the polypeptide or peptide included in a given unit dosage form of vaccine can vary widely, and depends upon factors such as the species, age, weight and physical condition of the animal considered for vaccination, as well as the method of administration. Such factors can be readily determined by the veterinarian employing animal models or other test systems which are well known to the art. A unit dose of a polypeptide or peptide vaccine is preferably administered parenterally, e.g., by subcutaneous or by intramuscular injection.

The polypeptides or peptides of the invention may also be conjugated or linked to an immunogenic protein, such as KLH or albumin, to enhance their immunogenicity. For example, synthetic peptides are coupled to KLH through the C-terminal cysteine of the peptide using the heterobifunctional reagent N-γ-maleimidobutyric acid N-hydroxysuccinimide ester (GMBS; Sigma). Carrier protein [4 mg KLH ml$^{-1}$ in 100 μl phosphate buffered saline (PBS) pH 7.4] is activated by reaction with GMBS (0.5 mg per 5 μl dimethylformamide) for 1 hour at 25° C. under nitrogen gas. The activated protein is separated from excess GMBS by gel filtration on Sephadex G25 (Pharmacia). Column fractions containing the carrier protein (monitored by $A_{280}$) are pooled, and added to 4 mg peptide dissolved in an equivalent volume of PBS. The mixture is gassed with nitrogen, and incubated at 25° C. for 3 hours with gentle stirring. The progress of the conjugation is monitored colorimetrically from reactivity of free cysteine thiol groups with Ellman's reagent. Coupling is complete when no color change is observed. The carrier-conjugated peptides are stored at −20° C. until used.

Preferably, the administration of the antigen to a bird results in an immune response, e.g., the production of antibodies to turkey astrovirus-2, and/or inhibits or prevents PEMS and/or poult enteritis. Both local and systemic administration is contemplated.

Also envisioned is the administration of maternal antibody, which antibody is obtained from a female animal exposed to a recombinant cell, a nucleic acid molecule encoding an antigen of turkey astrovirus-2, or isolated peptide or polypeptide of the invention. For example, a hen is vaccinated with at least one of the immunogenic compositions of the invention. The hen then provides passive immunity to progeny through the transfer of maternal antibody to the embryo. Alternatively, an egg-laying animal may be immunized and the eggs from that animal collected. Antibody is recovered from the eggs and then administered to susceptible animals to provide passive protection.

Typically, immunogenic compositions are prepared for injection or infusion, either as liquid solutions or suspensions. Solid forms suitable for solution in, or suspension in, liquid vehicles prior to injection or infusion may also be prepared. The preparation may also be emulsified. The active ingredient can be mixed with diluents, carriers or excipients which are physiologically acceptable and compatible with the active ingredient(s). Suitable carriers can be positively or negatively charged or neutral avridine-containing liposomes, oil emulsions; live-in-oil; killed-in-oil, water-in-oil; Al(OH)$_3$; oil emulsion with terpene oils squalene or squalene; or aqueous. Suitable diluents and excipients are, for example, water, saline, PBS, glycerol, or the like, and combinations thereof. In addition, if desired, the compositions may contain minor amounts of auxiliary substances such as wetting or emulsifying agents, stabilizing or pH-buffering agents, and the like.

Such compositions are conventionally administered parenterally, by injection, for example in birds, either intravenously, intramuscular injection to breast, lung or thigh, subcutaneous injection, wing web injection, or administration via the beak, spraying the animals and their environment, e.g., their housing or yard, or administration in the drinking water or feed. The administration of maternal antibody or recombinant cells is preferably in feed or water, or in ovo. Polypeptide or peptide is preferably administered via injection. Formulations which are suitable for other modes of administration include suppositories, cloaca, insufflated powders or solutions, eye drops, nose drops, intranasal aerosols, and oral formulations, e.g., introduced into drinking water. Oral formulations include such normally employed excipients as, for example, pharmaceutical grades of alkylcelluloses, mannitol, dextrose, lactose, starch, magnesium stearate, sodium saccharin, cellulose, magnesium carbonate, and the like. Thus, these compositions can take the form of solutions, suspensions, tablets, pills, hard or soft gelatin capsules, sustained-release formulations such as liposomes, gels or hydrogels; or powders, and can contain about 10% to about 95% of active ingredient, preferably at about 25% to about 70%.

One or more suitable unit dosage forms comprising the cell preparations, or polypeptides or peptides of the invention, may optionally be formulated for sustained release. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

To prepare an immunogenic composition comprising a polypeptide or peptide, the polypeptide or peptide can be isolated as described hereinabove, lyophilized and stabilized. Alternatively, the polypeptide or peptide may be modified so as to result in a derivative polypeptide or peptide, as described above. The polypeptide or peptide antigen may then be adjusted to an appropriate concentration, optionally combined with a suitable carrier and/or suitable vaccine adjuvant, and preferably packaged for use as a vaccine. Suitable adjuvants include, but are not limited to, surfactants, e.g., hexadecylamine, octadecylamine, lysolecithin, di-methyldioctadecylammonium bromide, N,N-dioctadecyl-n'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, dimethylglycine, tuftsin, oil emulsions, alum, and mixtures thereof. Finally, the immunogenic product may be incorporated into liposomes for use in a vaccine formulation, or may be conjugated to polysaccharides or other polymers.

A pharmaceutically acceptable carrier can comprise saline or other suitable carriers (Arnon, R. (ed) Synthetic Vaccines I. 83-92, CRC Press, Inc., Boca Raton, Fla., 1987). An adjuvant can also be a part of the carrier of the vaccine, in which case, it can be selected by standard criteria based on the antigen used, the mode of administration and the subject (Arnon 1987; supra) Methods of administration can be by oral or sublingual means, or by injection, depending on the particular vaccine used and the subject to whom it is administered.

Vaccination schedules and efficacy testing for avians are well known to the art, e.g., see Rimler et al., 1979; Schlink et al., 1987; Wang et al., 1994a; Wang et al., 1994b; Zhang et al., 1994; and Rimler et al., 1981.

The invention will be further described by the following non-limiting examples.

EXAMPLE I

Materials and Methods

TAstV-2 Propagation. TAstV-2 was isolated and propagated as described in Koci et al. (2000a) and Schultz-Cherry et al. (2001). Briefly, the thymus or intestines from infected turkey poults were homogenized, 0.2 μm filtered, and inoculated into the yolk sac of 20-day-old specific pathogen-free (SPF) turkey embryos (from a closed flock of Small Beltsville White turkeys housed at Southeast Poultry Research Laboratory). Viral replication in embryo intestines was monitored by in situ hybridization at 1, 3, and 5 days post-inoculation (dpi). Virus was harvested at 5 dpi. Intestines were removed, homogenized, 0.2 μm filtered and centrifuged at 150×g for 10 minutes. Additionally, embryo intestinal fluid was collected separately, 0.2 μm filtered and centrifuged at 500×g for 10 minutes.

RNA Isolation and RT-PCR. Total RNA was isolated from purified virus, embryo intestines, or from tissues excised from experimentally-inoculated or control turkeys using Trizol™ following manufacturer instructions (Invitrogen, Carlsbad Calif.). RT-PCR was performed as previously described in Koci et al. (2000b).

TAstV-2 Quantitation. Viral load was assessed by developing a TAstV-2-specific competitive quantitative RT-PCR (CQ RT-PCR) system. Briefly, total RNA, isolated from 100 μl of infectious material, was analyzed by one-step RT-PCR (Qiagen, Valencia Calif.) in the presence of a competitor RNA (cRNA). The cRNA was generated by modifying a plasmid (pTAstVpol18) which contains nucleotides 2863 to 5296 of the TAstV-2 genome. pTAstVpol 18 was digested with Sca I following the manufacturer's instructions (Invitrogen), then two 30 bp randomly generated oligonucleotides were ligated to the cut plasmid to generate a construct with TAstV-2 pol gene with 60 bp of additional sequence (pTAstVpolC). This new construct was then digested with Sst I and Not I following the manufacturer's instructions (Invitrogen) and ligated into the corresponding sites in pGEM T-Easy vector (Promega, Madison Wis.). This final construct pTAstVpolCQ, was then used to generate positive sense cRNA using the RNA polymerase SP6 (Roche Molecular, Indianapolis, Ind.). cRNA was purified, and copy numbers quantitated using spectrophotometry as described in Sambrook et al. (1989). TAstV-2 polymerase gene specific primers, flanking the modified region in pTAstVpolCQ, were designed (CQ RT-PCR Fwd; CCATGATATGC-TACGGGGAT; SEQ ID NO:1) and CQ RT-PCR Rev; GACTCAACATCTGGTAGCCT; SEQ ID NO:2). Sample RNA was added at a uniform concentration to each tube of a serial log dilution of cRNA, and amplified under the following conditions; 50° C. for 30 minutes, 95° C. for 15 minutes, 30 cycles of 94° C. for 30 seconds, 55° C. for 30 seconcds, 72° C. for 30 seconds, and final 72° C. extension for 1 minute, using the Qiagen OneStep RT-PCR Kit (Qiagen, Valencia Calif.) in a total reaction volume of 25 μl. Products were then separated by electrophoresis in an agarose gel and the amplification products visualized with ethidium bromide. The copy numbers of viral RNA in the sample/ml were calculated using Kodak Imaging Software densitometry and plotting against the standard curve of the competitor as previously described in Frieman et al. (1999).

Animals. Two-day-old unvaccinated British United Turkey of America poults (male and female) were obtained from a commercial hatchery. Control and infected poults were housed in separate BL2 containment facilities in individual Horsfall units with HEPA filtered inlet and exhaust air valves. Birds were fed routine turkey starter from the University of Georgia and given free access to clean water. After a brief acclimation period, five-day-old poults were weighed (day 0) and randomly assigned to either a control group or a group infected with astrovirus (n=60 per group). Poults were orally inoculated with about $10^6$ genomic units of astrovirus in 200 μl total volume, or phosphate buffered saline (PBS) alone. Birds were monitored daily for signs of clinical disease and weighed on 0, 3, 5, 9, and 12 dpi. On days 1, 2, 3, 4, 5, 7, 9, and 12 pi, five random poults per group were euthanized by cervical dislocation and the small intestine, bursa, spleen, pancreas, thymus, liver, kidney, bone marrow, skeletal muscle (breast), feces and blood were collected. All tissues were stored at −70° C. or placed in 10% phosphate-buffered formalin. Blood was collected in syringes containing heparin, incubated overnight at 4° C. and then separated into red cell, lymphocyte, and plasma fractions using Histopaque 1077 (Sigma Chemicals, St. Louis, Mo.). The bursa, spleen, and thymus from each group were weighed to the nearest milligram prior to processing.

To perform RT-PCR analysis and virus isolation studies, the individual tissues at each time point were pooled, homogenized, and aliquoted for RNA isolation using Trizol™ or inoculation into 20-day-of-age turkey embryos. The animal experiments were repeated five times with different groups of poults with similar results.

In situ Hybridization. The TAstV-2-specific riboprobe was generated as described in Behling et al. (2002). Briefly, TAstV-2 plasmid p25.5 containing a 1.5 kb segment of the extreme 3' end of the TAstV-2 genome (Koci et al., 2000a) was digested with BamHI and transcribed with T7 RNA polymerase and digoxigenin labeled UTP (Roche Molecular), creating an antisense riboprobe of approximately 1.6 kb in length. Digoxigenin incorporation was verified by dot-blot. In situ hybridization was performed according to previously described techniques (e.g., see Brown, 1999). Briefly, tissue sections were deparaffinized with Citrisolv (Fisher Scientific, Norcross Ga.), digested with 35 µg/ml Proteinase K for 15 minutes at 37° C., and hybridized overnight at 42° C., using approximately 35 ng of digoxigenin-labeled riboprobe per slide in 5× standard sodium citrate (SSC), 50% formamide, 5% modified milk protein (Roche Molecular), 1% N-lauroylsarcosine, and 0.02% SDS. The following day, slides were washed in increasingly stringent solutions, i.e., 2×SSC with 1% SDS for 30 minutes at 50° C., 1×SSC with 0.1% SDS for 30 minutes at 50°, 1×SSC for 15 minutes three times at room temperature, and 0.1×SSC for 15 minutes at room temperature. After the posthybridization washes, sections were incubated with anti-digoxigenin antibody conjugated to alkaline phosphatase (Roche Molecular) for 2 hr at 37° C. and developed with nitroblue tetrazolium and bromcresylindolyl phosphate for 1 to 3 hours. Sections were counter-stained lightly with hematoxylin and coverslipped with Permount for a permanent record. Each group of slides was processed with a positive control tissue consisting of a section of positive embryo intestine, and negative control sections from uninfected poults.

Histopathology. Tissues from control and infected poults were fixed in 10% phosphate buffered formalin overnight, then processed, embedded, sectioned (0.3 µm), and stained with hematoxylin and eosin and examined by light microscopy.

Detection of TAstV-2 Antigen by Immunofluorescence. The distribution of TAstV-2 was monitored using a rabbit polyclonal antibody generated to a peptide sequence in the TAstV-2 capsid protein ($K_{676}$-$R_{691}$) (ResGen, Carlsbad Calif.), accession# AAF18464. Briefly, tissue sections from turkeys sacrificed at 1, 2, 3, 4, 5, 7, 9, and 12 days post-inoculation (dpi) were processed as described above, deparaffinized with Citrisolv, antigenic sites exposed by microwaving the tissues for 5 minutes in a citrate buffer, then incubated with primary antibody diluted 1:500 in phosphate buffered saline containing 0.1% Tween-20 (PBST) overnight at 4° C. After incubation in primary antibody, the slides were washed in PBST, incubated with a biotinylated goat anti-rabbit antibody (Vector Laboratories, Burlingame, Calif.) for 30 minutes at room temperature (RT), washed in PBST, then incubated with a Alexa488-streptavidin-labeled antibody (Molecular Probes, Eugene Oreg.) diluted 1:200 in PBST for 1 hour at RT. Slides were mounted in PBS+glycerol and fluorescence was examined on a motorized Zeiss Axioplan IIi equipped with a rear mounted excitation filter wheel, a triple pass (DAPI/FITC/Texas Red) emission cube, and a Zeiss AxioCam B&W CCD camera. Fluorescence images were pseudocolored, and merged using OpenLabs 3.0 software (Improvision Inc., Lexington Mass.).

Co-Localization of TAstV-2 Antigen and Apoptosis. To determine if TAstV-2 induced cell death, intestinal sections from control or TAstV-2-infected turkey poults were deparaffinized and antigenic sites exposed as described above, then incubated with terminal deoxynucleotide transferase labeled with tetramethylrhodamine red fluorescence (In situ End Labeling TUNEL analysis, Roche Molecular) for 1 hour at 37° C. following manufacturer's instructions. Immediately following TUNEL staining, the sections were washed three times with PBST and stained for TAstV-2 as described above.

Statistics. Data comparing body weights and lymphoid organ weights were analyzed by one-way analysis of variance (ANOVA) and pairwise multiple comparison using the Student Newman-Keuls method (SigmaStat, Jandel Scientific, San Rafael, Calif.). Significance level was defined at $P<0.05$.

Results

Propagation of TAstV-2 in Embryos.

Attempts to propagate TAstV-2 in cell culture using primary turkey embryo fibroblast, turkey embryo kidney cells, chicken embryo fibroblast, chicken embryo kidney cells, African Green Monkey kidney cells (Vero), mink lung epithelial cells (Mv1Lu), Madin-Darby canine and bovine kidney cells (MDCK and MDBK), a human colorectal adenocarcinoma cell line (Caco-2), and an ileocecal colorectal adenocarcinoma cell line (HCT-8), were unsuccessful. Therefore, specific pathogen-free (SPF) turkey embryos at 20 embryonic days of age were inoculated with a tissue filtrate prepared from healthy or TAstV-2-infected turkey poults and incubated for 1, 3 or 5 days at 39° C. Intestines were removed and tested for TAstV-2 RNA and replication by RT-PCR and in situ hybridization respectively. RT-PCR analysis on embryo intestines was positive for TAstV-2 at days 1 through 5 post inoculation. In situ hybridization showed extensive viral replication within 1 dpi. TAstV-2 replication increased until 3 dpi and then began to decrease by 5 dpi. No TAstV-2 in situ staining was detected in the control embryos. Interestingly at 5 dpi, TAstV-2-infected embryo intestines were enlarged, thin-walled, and distended. An immense accumulation of intestinal fluid was also observed in the intestines of TAstV-2-infected embryos but not the controls. These results demonstrate that turkey embryos support TAstV-2 replication and are a valuable source for in vitro propagation.

TAstV-2-Induced Disease.

Clinical Signs and Gross Lesions

Inoculation of naive poults with $10^6$ genomic units of TAstV-2 resulted in 100% of the infected birds developing diarrhea within 24 hours of challenge that continued throughout the course of the 12 day experiment. Diarrhea was watery, yellow, frothy, mucus-filled, but did not contain undigested food or blood. Control animals had no diarrhea. In addition to the diarrhea, infected birds exhibited statistically significant growth depression as compared to uninfected controls ($p<0.05$). At 5 dpi, there was a about 27% difference in the growth, and a 38% difference by 12 dpi. The TAstV-2-infected birds remained smaller throughout experiments extended to 28 dpi.

Upon necropsy, the intestines of infected poults were distended, dilated, and gasfilled. The intestines appeared to be three to five times the size of those of the noninfected controls. In addition to the macroscopic changes seen in the intestines, we noted that the bursa and thymus, and to a lesser extent the spleens, of the infected animals appeared reduced in size. To examine this further, these organs were removed, weighed, and compared to those of the mock-infected poults. Birds infected with TAstV-2 had a statistically significant decrease in the size of the thymus beginning 3 dpi and continuing through 9 dpi ($p<0.05$). Calculating the differences as a ratio of organ weight to body weight we found, at 3 dpi, the thymus of the TAstV-2-infected group was 36% smaller than the control group and 52% smaller at 9 dpi. However, by 12 dpi, there was no difference in the relative thymic size suggesting these changes were transient. There were no statistically significant differences in the sizes of the bursa or spleen as compared to controls.

Histopathological Lesions

To investigate the histologic changes resulting from TAstV-2 infection, tissues were examined by routine hematoxylin and eosin staining and light microscopy. In spite of the severe diarrhea, the intestinal lesions were mild. By 2 dpi, there were scattered single degenerating villous epithelial cells, predominantly in the basal portions of the villi. These degenerating cells were present through 9 dpi. Crypt hyperplasia was very mild at 3 dpi and continued through 12 dpi. By 5 dpi there was a minimal amount of mononuclear inflammatory infiltrate in the lamina propria that resolved by 12 dpi. Because of the gross changes seen in the thymus we also examined extra-intestinal tissues; bursa, spleen, pancreas, thymus, liver, kidney, bone marrow, skeletal muscle, and blood. No remarkable histologic changes were noted in any of these tissues. No lesions were seen in any of the control tissues. These findings demonstrate that TAstV-2 infection resulted in severe diarrhea, growth suppression, and reduction in thymic mass in the absence of widespread inflammation or cellular damage.

Localization of TAstV-2

TAstV-2 was originally isolated from the thymus suggesting that TAstV-2 is present outside the intestines (Schultz-Cherry et al., 2000). The distribution of TAstV-2 was examined at different times post-infection by RT-PCR, isolation of infectious virus, immunofluorescence, and in situ hybridization. Not surprisingly, infectious virus could be isolated from the feces and intestines at all time points in the experiment from day 2 onward; however, the levels of virus in the feces at 1 dpi were below the level of detection by RT-PCR. TAstV-2 RNA was also detected by RT-PCR in the thymus, bursa, spleen, liver, kidney, pancreas, skeletal muscle, bone marrow, and in the plasma fraction of infected birds, generally at 3 and 5 dpi; and the thymus and spleen were still positive at 7 dpi. Infectious virus could be isolated from all of the samples generally between 3 to 7 dpi. The presence of TAstV-2 outside the intestines was also detected by immunofluorescence. Mild, limited TAstV-2 capsid staining was detected in all tissues examined, most consistently between 3 and 5 dpi. No staining was observed in control tissues. Although there was infectious virus and viral antigen staining in extra-intestinal tissues, in situ hybridization data suggested that astrovirus replication was limited to the intestines. No replicating virus was detected in representative extra-intestinal tissues (thymus, bursa, and spleen). In situ staining of the TAstV-2 genome in the intestines was generally found in the deep edges of the villi and not in the crypts. A similar staining pattern for TAstV-2 capsid protein was observed, with antigen detected in the cytoplasmic portion of specific enterocytes at the mid-region of the villi.

TAstV-2 Infection Does Not Increase Cell Death

The lack of histologic lessions in the intestines of TAstV-2-infected animals was surprising given the levels of viral replication and diarrhea. To determine if TAstV-2-infected cells undergo cell death, intestinal sections from control and infected poults were double-labeled for TAstV-2 capsid protein and cell death using TUNEL analysis. Not surprisingly, there was a great deal of TUNEL staining in both control and TAstV-2-infected intestines. In contrast astrovirus staining was found only in the cytoplasm of enterocytes of infected but not control intestines. Double-labeling the tissues resulted in no overlap of TUNEL-positive cells with TAstV-2-infected cells, suggesting that astrovirus replication does not result in an increase in cell death. Identical results were observed in TAstV-2-infected embryos (data not shown). These experiments suggest that TAstV-2 does not increase cell death, which supports the histopathology observations.

Discussion

In these studies, an in ovo method to propagate high titers of infectious virus and a small animal model that will be useful to further understand astrovirus pathogenesis and the host response to infection, were described. The present studies examined the pathogenesis of astrovirus infection including the kinetics of astrovirus replication, the location of the virus and its ability to localize to extra-intestinal sites, and, most surprisingly, the induction of diarrhea in the absence of either cellular damage or an increased inflammatory response.

All of the human astrovirus (HAstV) strains were adapted to replicate in cell lines (Briner et al., 2000; Lee et al., 1981; Taylor et al., 1987). In contrast, TAstV-2 did not propagate in cell lines that support HAstV replication, or in primary turkey or chicken cells. Fortunately, TAstV-2 can be propagated in turkey embryos. Inoculation of TAstV-2 in the yolk sac of 20-day-of-age turkey embryos resulted in productive viral replication, accompanied by an accumulation of fluid in the intestines of infected embryos. This fluid typically contains $10^{11}$ viral genomic units/ml as determined by CQ RT-PCR. Limiting dilutions in embryos followed by immunofluorescent staining for the viral capsid protein suggested that the fluid contained at least $10^9$ infectious viral particles/ml.

TAstV-2 is highly infectious and extremely stable in the environment (Schultz-Cherry et al., 2001); therefore, control birds had to be housed in separate rooms to avoid cross contamination. Additionally, placing naive poults in contact with infected birds or in cages that previously housed TAstV-2 infected birds resulted in immediate infection and diarrhea. Similar to mammalian astroviruses, younger animals are more susceptible to TAstV-2 infection. Infecting older naive birds with TAstV-2 induced diarrhea; however, the duration of viral replication and the clinical signs were reduced in older animals. Infecting naive poults with TAstV-2 resulted in diarrhea in 100% of the birds within 24 hour post-infection. Infected poults had a reduced growth rate, and remained significantly smaller than controls throughout the experiment. In addition to the growth depression, infected poults also had significantly reduced thymus weights, although this difference had resolved by the end of the experiment. The mechanism for the reduced growth rate and undersized thymus is not understood; however, both are likely directly related to the diarrhea. Infected birds likely suffer some nutritional deficiencies. Infected birds consumed the same amount of feed as the age matched controls, but did not gain weight at the same rate. In additional studies, birds given nutritional additives did not have as severe weight loss or changes to the thymus.

TAstV-2 RNA and infectious virus were detected in every tissue examined, including the blood. To confirm that TAstV-2 RNA and infectious virus present in nonintestinal tissues was independent of contaminating blood, tissues were washed extensively in PBS or incubated overnight in large volumes of formalin followed by a second 48 hour incubation in PBS prior to processing. Thus, it is unlikely the TAstV-2 is due to contaminating blood. Additionally, we confirmed the presence of TAstV-2 in nonintestinal organs by immunofluorescent staining for the capsid protein. The distribution of viral antigen and RNA throughout non-intestinal organs peaked at 5 dpi then waned. By 12 dpi, only the intestine contained virus. There was limited capsid staining in lymphoid areas of the thymus and bursa and in the kidney epithelia. However, most of the TAstV-2 capsid staining in the extra-intestinal tissues was associated with vasculature. Previously it was unknown if astroviruses induced viremia. In this study, TAstV-2 RNA and low titers of virus were detected in plasma samples from infected poults. Many viruses induce viremia during which the viruses circulate in the blood, serum, or white blood cells (WBCs) and are spread to target organs to initiate infection (Mims et al., 1989). The mechanism by which TAstV-2 enters the blood stream and spreads to extra intestinal organs is unknown. Studies with astrovirus in lambs and calves suggested a possible role for macrophages, Peyer's patches, and M cells in infected animals (Behling-Kela et al., 2002). However, macrophages isolated from the spleens of TAstV-2-infected poults did not contain infectious virus. Collectively, these results suggest that viremia occurs following TAstV-2 infection and that the TAstV-2-positive sera contain infectious virus.

Although, extra-intestinal tissues contained TAstV-2 antigen and RNA, only the intestine appeared to support viral replication as determined by in situ hybridization. Limited replication was observed in the cecal tonsils and distal small intestine within 1 dpi. By 3 dpi, replication was pronounced in the cells of the mid-villus of the cecal tonsils and distal small intestine (duodenum) with expansion to the epithelium of the large intestine and small intestine. By 9 dpi, only minimal viral replication was observed (Behling-Klia et al., 2002).

Many enteric pathogens induce diarrhea by destroying enterocytes in the villous epithelium ultimately leading to cell death and villous atrophy (Lundgren et al., 2000). This does not appear to be the case with TAstV-2. In spite of the diarrhea, there were only minimal to mild histologic changes in the intestines during TAstV-2 infection. The lack of substantial histologic changes noted in the intestines was supported by TUNEL analysis. TUNEL staining demonstrated that cell death was not increased during infection, either in general or specifically in TAstV-2 infected cells. Similar results were obtained using the apoptosis-specific antibody, caspase 3 (data not shown).

EXAMPLE II

Methods

Recombinantly-expressed TAstV-2 capsid protein was generated utilizing the Bac-To-Bac Baculovirus Expression System (Invitrogen) following the manufacturer's instructions. Briefly, the TAstV-2 capsid gene was subcloned from pcDNA3.1−/TAstVcap10 into the pFastBac™ HTa expression vectors (Invitrogen) to generate pFastBacHT/TAstV-2capsid. The resultant plasmid was screened by sequence analysis to ensure generation of the fusion protein, and to confirm the integrity of the TAstV-2 gene. The construct was recombined into the *Autographa californica* nuclear polyhedrosis virus (AcNPV) genome via DH10Bac cells. The recombinant baculovirus (rAcNPV/TAstV-2capsidHis) was propagated in serum-free media (SFM)-adapted Sf9 or Sf21 insect cells and used to express TAstV-2 capsid protein. The infected cells were harvested at different times post-infection and monitored for capsid protein expression by Western blot analysis and immunofluorescence microscopy using TAstV-2-specific antibodies. Specifically, baculovirus infected insect cells were lysed with 50 mM Tris (pH 8) containing 1 mM phenylmethylsulfonyl fluoride (PMSF) and 1% NP40. Cells were frozen and thawed twice and cell debris removed by centrifugation. His-tagged rTAstV-2 capsid protein was purified using Ni—NTA agarose beads (Qiagen) following the manufacturer's instructions. Affinity purified His-tagged protein was purified over a D-Salt Excellulose GF-5 Desalting Column (Pierce) to remove the imidazole elution buffer, and samples were checked for protein by SDS PAGE and western blot using Penta-His Ab (Qiagen) or anti-KHL IgG sera (see below).

TAstV-2 Capsid Peptides

Three peptides derived from predicted amino acid antigenicity and surface probability analysis were synthesized commercially (Invitrogen) corresponding to amino acid positions 32-47 (RSRTKKTVKIIEKKPE, RSR; SEQ ID NO:3), 194-221 (HPRSALGPRQGWWNVDPGD, HPR; SEQ ID NO:4) and 676-691 (KHLEEEKNYWKNQCER, KHL; SEQ ID NO:5). These peptides were used to stimulate HD11 cell, in soluble form, immobilized on microtiter plates, or cross-linked using disuccinimidyl suberate (DSS, Pierce). HD11 cells ($1\times10^5$/well) were stimulated with 1-25 μg of peptides or bovine serum albumin (BSA) in each of the above forms.

Results

Recombinant TAstV-2 capsid protein (rTAstV-2cap) was produced in the baculovirus expression system. Western blot analysis and electron microscopy confirmed that recombinant capsid protein was expressed in infected insect cells (data not shown). In particular, high levels of astrovirus capsid protein were expressed at 48 hours to 72 hours post-infection (hpi).

His-tagged TAstV-2 capsid protein was affinity purified and added to HD11 cells. The addition of 1 μg of affinity purified rTAstV-2cap to HD11s stimulated NO production. NO levels were similar in cells treated with purified TAstV-2. These data demonstrated that the TAstV-2 capsid protein was sufficient to stimulate expression of NO.

Cells were also treated with peptides derived from the TAstV-2 capsid sequence. These peptides were selected based on surface probability and antigenicity index analysis, as well as sequence conservation. HD11 cells were treated with the peptides in soluble, bound, and cross-linked forms. None of the peptides stimulated NO production regardless of form. In addition, pre-incubating TAstV-2 with purified IgG specific to these peptide sequences failed to inhibit NO activity when added to HD11 cells, and pre-incubating the cells with the peptides did not inhibit binding. These results suggested that these peptides did not represent the cellular binding regions of the capsid protein.

EXAMPLE III

Methods

Cell Culture. Serum free adapted Sf9 (*Spodoptera frugiperda*) cells (Invitrogen)were grown in Sf-900 II SFM (Invitrogen), in 25 ml suspension cultures, using plastic 200 ml Erlenmeyer flasks, on an orbital shaker at 145 rpms, at 27° C. Cells were grown to a density of $2\times10^6$ cells/ml and 98% viability, and passaged at a cell density of $5\times10^5$ cells/ml.

Recombinant baculovirus. Recombinant baculovirus expressing the TAstV-2 capsid protein was generated utilizing the Bac-To-Bac Baculovirus Expression System (Invitrogen) following the manufacturer's instructions (see Example II). An additional construct was created from pFastBacHT/TAstV-2capsid, in which the hisitidine tag was removed. Briefly, pFastBacHT/TAstV-2capsid was digested with Nco I (Invitrogen), Rsr II (Invitrogen), and Mung Bean S1 nuclease (New England Biolabs), and re-ligated using T4 ligase (Invitrogen). The resultant plasmid was screened by sequence analysis. The constructs were each recombined into the *Autographa californica* nuclear polyhedrosis virus (AcNPV) genome via DH10Bac cells. The recombinant baculoviruses (rAcNPV/TAstV-2capsidHis, and rAcNPV/TAstV-2capsid) were propagated in serum-free media (SFM)-adapted Sf9 insect cells.

Antigen. Sf9 cells were seeded in 96 well plates at a concentration of $1 \times 10^5$ cells/well, and cultured at 27° C. for 2 hours. After cells attached to the wells, the culture media was removed and cells were infected with recombinant baculovirus or wild-type AcNPV (Paul Friesen, University of Wisconsin, Madison) at a multiplicity of infection (MOI) of 5. All wells were brought to a final volume of 100 μl in Sf-900 II SFM, and cells were incubated for 72 hours at 27° C. Following incubation, the culture media was removed and cells were washed with 200 μl of PBS. Cells were then fixed in cold methanol:acetone (1:1) for 10 minutes. Fixative was removed, the cells were washed with PBS, then PBS was removed, and the plates stored at −20° C. until needed.

Anti-TAstV-2 Immunofluorescence Assay. Fixed, frozen infected insect cells were warmed to room temperature, and rinsed once with PBS. Test serum from unknown turkeys was diluted 1:10 in PBS, and 25 μl added to both a rAcNPV/TAstV-2capsid infected well and an AcNPV infected well (negative control). As an assay control, a rabbit polyclonal sera generated against a peptide derived from the TAstV-2 predicted capsid sequence (amino acids 676-691, an "anti-KHL IgG" sera), was diluted 1:750 in PBS and added to both a positive and negative control well, respectively. The plate was incubated for 1 hour at room temperature. Following incubation, the wells were washed with 200 μl of PBS three times. Following the final wash, PBS was removed, and secondary antibody added. Unknown turkey samples were detected using secondary Goat Anti-Turkey IgG(H+L)–FITC (Southern Biotech) at a dilution of 1:100 in PBS. The assay control wells, were detected using an anti-rabbit IgG-rhodamine (Jackson Labs) secondary antibody diluted 1:750. Antibodies were added in 25 μl total volume and incubated at room temperature for 1 hour. Following secondary antibody binding, wells were washed with 200 μl of PBS three times, and once with water. Water was removed and 10 μl of PBS: glycerol (1:1) added to each well. Cells were then examined for fluorescence using an inverted UV microscope. The presence of TAstV-2 capsid protein specific antibodies in the unknown turkey serum samples was determined by comparing the level of FITC fluorescence between test well (rAcNPV/TAstV-2capsid infected Sf9 cells) and negative control well (wild-type AcNPV infected Sf9 cells).

Samples. Feces and intestines were collected from turkey poults infected with turkey astrovirus-2 or PEMS inoculum at 5 days post-infection (dpi). At 2 weeks post-infection, serum was collected and used for the serologic assay. In addition, intestines from 3 to 5 birds/PEMS-positive flock at 1 week of age and serum from the same flocks 3 weeks later, were collected.

Results

To determine whether recombinant cells expressing turkey astrovirus-2 capsid protein could detect anti-turkey astrovirus-2 antibodies present in a physiological sample, serum was collected from turkey poults infected with turkey astrovirus-2 or PEMS inoculum, and from a PEMS-positive flock. In addition, cRNA was isolated from the feces or intestines of PEMS-infected turkey poults and tested for the presence of turkey astrovirus-2 using a RT-PCR test (Example I).

Some of the results are shown in Table 3. Thus, the serological assay accurately detects the presence of turkey astrovirus-2 infected birds.

TABLE 3

Comparison of Turkey Astrovirus-2 Serologic Test to RT-PCR

| Samples | Total # of samples tested[a] | # Positive by Serologic Test[b] | # Positive by RT-PCR[c] |
|---|---|---|---|
| Experimental Study 1 | 5 | 3 | 4 |
| Experimental Study 2 | 8 | 6 | 6 |
| Experimental Study 3 | 5 | 5 | 5 |
| Samples from Commercial Turkey Flocks[d] | 6 | 4 | 6 |

[a]Feces and intestines were collected from turkey poults infected with TAstV-2 or PEMS inoculum at 5 days post-infection (dpi). At 2 weeks post-infection, serum was collected and used for the serologic assay.
[b]Serum was tested for the presence of astrovirus antibodies using insect cells infected with baculovirus expressing TAstV-2 capsid protein.
[c]RNA was isolated from the feces or intestines of PEMS-infected turkey poults and tested for TAstV-2 using described RT-PCR tests.
[d]A turkey company in North Carolina with PEMS-positive flocks collected intestines from 3 to 5 birds/flock at 1 week of age and serum from the same flocks 3 weeks later.

REFERENCES

Abad et al., *Applied and Environmental Microbiology*, 63:3119 (1977).
Aroonprasert et al., *Vet. Microbiol.*, 19:113 (1989).
Barnes et al., In B. W. Calnek and H. J. Barns and C. W. Beard and L. R. McDougald and Y. M. Saif (ed.), Diseases of Poultry, 10 ed. Iowa State University Press, Ames.
Bass et al., *J. Virol.*, 74:1810 (2000).
Bavaay and Merrifield, "The Peptides," eds. E. Gross and F. Meienhofer, Vol. 2 (Academic Press, 1980) pp. 3-285.
Behling-Kelly et al., *Vet. Path.*, 39:595 (2002).
Belliot et al., *Arch. Virol.*, 142:1323 (1997).
Brandenberger, PEMS Funding, The National Turkey Federation.
Bridger, *Vet. Rec.*, 107:532 (1980).
Brinker et al., *Arch. Virol.*, 145:1847 (2000).
Brown, *Vet. Pathol.*, 35:159 (1998).
Carter et al., *Arch. Virol. Suppl.*, 12:277 (1996).
Caul et al., *Journal of Medical Virology*, 9:257 (1982).
Craft et al., *J. Infect. Dis.*, 149, 789 (1984).
Cukor et al., *Microbiol. Rev.*, 48:157 (1984).
Edens et al., *Poult. Sci.*, 76:1665 (1997).
Edens et al., *World Poultry*, 15:43 (1999).
Englund et al., *Vet. Micro.*, 26:1 (2002).
Enguall et al., *Immunochemistry*, 8, 871 (1971).
Erlich, ed., *PCR Technology*, (Stockton Press, New York, 1989).
Freeman et al., *Biotechniques*, 26:112-22, 124-5 (1999).

Geigenmuller et al., *J. Virol.*, 76:2003 (2002).
Gibson et al., *Adv. Exp. Med. Biol.*, 440:387 (1998).
Glass et al., *Novartis Found. Symp.*, 238:5 (2001).
Goodgame, *Res. Immunol.*, 149:685 (1998).
Gorbalenya et al., *FEBS Lett.*, 243:103 (1989).
Gough et al., *Vet. Rec.*, 114:279 (1984).
Harbour et al., *Vet. Rec.*, 120:555 (1987).
Harlow and Lane, Antibodies; A Laboratory Manual, Cold Spring Harbor Laboratory, Cold Spring Harbor N.Y., 1988.
Imada et al., *J. Virol.*, 74:8487 (2000).
Jiang et al., *Proc. Natl. Acad. Sci. USA*, 90:10534 (1993).
Ishinama & Barbier, *Arch. Virol.*, 134:235 (1994).
Jonassen et al., *J. Gen. Virol.*, 82:1061 (2001).
Jonassen et al., *Journal of General Virology*, 79:715 (1998).
Jonassen et al., *Virus Res.*, 91:195 (2003).
Kiang et al., *J. Gen. Virol.*, 83:25 (2002).
Koci et al., *Journal of Virological Methods*, 90:79 (2000a).
Koci et al., *Journal of Virology*, 74:6173 (2000b).
Kriston et al., *Epidem. Infect.*, 17:159 (1996).
Kurtz et al., *J. Med. Virol.*, 3:221 (1979).
Kurtz et al., *Journal of Hospital Infection*, 1:321 (1980).
Kurtz et al., *Med Microbiol Immunol (Berl).*, 166:227 (1978).
Lee et al., *J. Gen. Virol.*, 57:421 (1981).
Lewis et al., *J. Virol.* 68:77 (1994).
Lewis & Matsui, *Arch. Virol.*, 140:1127 (1995).
Lewis & Matsui, *J. Virol.*, 70:2869 (1996).
Lewis & Matsui, *Adv. Exp. Med. Biol.*, 412:323 (1997).
Lukashov et al., *J. Gen. Virol.*, 83:1397 (2002).
Lundgren et al., *Science*, 287:491 (2000).
Madeley et al., *Lancet*, 2:451 (1975).
Magnarelli et al., *J. Clin. Microbiol.*, 20, 81 (1984).
Mahalingam et al., *J. Leukoc. Biol.*, 72:429 (2002.
Marczinke et al., *J. Virol.*, 68:5588 (1994).
Matsui et al., In D. M. Knipe, and P. M. Howley, (Eds.), Fields Virology, fourth edn, Vol. 1, (pp. 875-893). Balitmore: Lippincott Williams & Wilkins (2001).
McNulty et al., *Vet Rec.*, 106:561 (1980).
Meienhofer in "Hormonal Proteins and Peptides," ed.; C. H. Li, Vol. 2 (Academic Press, 1973), pp. 48-267.
Mendez et al., *J. Virol.*, 76:7996 (2002).
Merrifield, *J. Am. Chem. Soc.*, 85 2149 (1963).
Mims et al., (1984) Viral pathogenesis and immunology. In Blackwell (ed.). Blackwell, Oxford.
Mitchell, *Pediatr. Infect. Dis. J.*, 21:1067 (2002).
Mullis et al., *Cold Spring Harbor Symp. Quant. Biol.*, 51, 263 (1987).
Nicholas et al., *Veterinary Record*, 123:398 (1988).
Poch et al., *EMBO J.*, 8:3867 (1989).
Reynolds et al., *Avian Dis.*, 30:728 (1986).
Reynolds et al., *Avian Dis.*, 31:272 (1987a).
Reynolds et al., *Avian Dis.*, 31:89 (1987b).
Reynolds, (1991) In B. W. Calnek, (Ed.), Diseases of Poultry 9th edn, (pp. 635-638). Ames: Iowa State University Press.
Reynolds, In B. W. Calnek (ed.), Diseases of Poultry, 9th ed. Iowa State University Press, Ames (1991).
Russell et al., *J. Infect. Dis.*, 149, 465 (1984).
Sambrook et al., *Molecular Cloning: A Laboratory Manual*, Cold Spring Harbor Laboratory Press (2d ed., 1989)
Schneider & Roassinck, *J. Virol.*, 75:6566 (2000).
Schultz-Cherry et al., *Avian Dis.*, 44:256 (2000).
Schultz-Cherry et al., *Avian Dis.*, 45:76 (2001).
Schultz-Cherry et al., *Avian Diseases*, 45:76 (2001).
Snodgrass et al., *Arch. Virol.* 55:287 (1977).
Simmons et al., *Science*, 276, 276 (1997).
Stewart et al., *Solid Phase Peptide Synthesis*, W. H. Freeman Co., San Francisco (1969).
Taylor et al., *J. Virol Methods*, 67:13 (1997).
Thouvenelle et al., *Avian Dis.*, 39:328 (1995a).
Thouvenelle et al., *Avian Dis.*, 39:343 (1995b).
Tzipori et al., *Vet. Rec.*, 108:286 (1981).
Wang et al., *J. Med. Virol.*, 64:245 (2001).
Willcocks et al., *J. Gen. Virol.*, 75:1785 (1994).
Willcocks, *J. Gen. Virol.*, 80:2667 (1999).
Williams, *Arch. Virol.*, 66:215 (1980).
Woode et al., J. Med. Microbiol., 11:441 (1978).
Yu et al., *Avian Dis.*, 44:297 (2000).
Zander et al., (1991). Principles of Disease Prevention: Diagnosis and Control. In B. W. Calnek, (Ed.), Diseases of Poultry 9th edn, (pp. 3-34).Ames: Iowa State University Press.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to identify an animal exposed to turkey astrovirus-2, comprising:
   a) providing one or more blood samples from one or more animals suspected of being exposed to turkey astrovirus-2;
   b) contacting the one or more samples with a capsid antigen of turkey astrovirus-2, wherein the capsid antigen is present in fixed, recombinant insect cells comprising an expression cassette encoding the capsid antigen, or a lysate thereof; and
   c) detecting or determining whether the one or more samples comprise antibodies that bind the capsid antigen, thereby identifying whether the animal was exposed to turkey astrovirus-2.

2. A method to detect or determine antibodies to turkey astrovirus-2 in a physiological fluid sample from an animal, comprising:
   a) contacting one or more blood samples from one or more animals with a capsid antigen of turkey astrovirus-2; and
   b) detecting or determining the presence or amount of antibodies that bind the capsid antigen in the one or more samples, wherein the capsid antigen is present in fixed, recombinant insect cells comprising an expression cassette encoding the capsid antigen, or a lysate thereof.

3. The method of claim 1 or 2 wherein the blood sample is a serum sample or a plasma sample.

4. The method of claim 1 or 2 wherein the sample is from an avian or a mammal.

5. The method of claim 4 wherein the avian is a turkey or a chicken.

6. The method of claim 1 or 2 wherein the cells are attached to a substrate.

7. The method of claim 6 wherein the substrate comprises a material selected from the group consisting of plastic, glass, celluloid, paper, and particulate materials.

8. The method of claim 6 wherein the substrate is a well, a plate, a dipstick, a bead, a membrane, a filter, a tube, or a dish.

9. The method of claim 1 or 2 wherein the antibodies that are specific for the antigen of turkey astrovirus-2 are detected with a detectable moiety or a moiety capable of detection.

10. The method of claim 9 wherein the moiety is an antibody.

11. The method of claim 9 wherein the detectable moiety comprises an enzyme, a radionuclide, a fluorescent molecule, a chemiluminescent molecule, a chromophore, or a ligand.

12. The method of claim 10 wherein the antibody comprises an enzyme, a radionuclide, a fluorescent molecule, a chemiluminescent molecule, a chromophore, or a ligand.

13. The method of claim 1 or 2 wherein the antigen is not denatured.

14. The method of claim 1 or 2 wherein the detecting or determining comprises an assay selected from the group consisting of an enzyme-linked immunoassay, a radioimmunoassay, or a fluorescence immunoassay.

15. A kit for the diagnosis of turkey astrovirus-2 infection, comprising a substrate and a capsid antigen of turkey astrovirus-2, wherein the capsid antigen is present in fixed, recombinant insect cells comprising an expression cassette encoding the capsid antigen, or a lysate thereof.

16. The kit of claim 15 further comprising a positive control.

17. The kit of claim 15 further comprising a negative control.

18. The kit of claim 15 further comprising a diluent.

19. The kit of claim 15 further comprising an anti-avian antibody comprising a label.

20. The kit of claim 19 wherein the label is an enzyme, a radionuclide, a fluorescent molecule, a chemiluminescent molecule, a chromophore, or a ligand.

21. The method of claim 3 wherein the one or more blood samples are one or more avian serum samples that are contacted with the fixed, recombinant insect cells comprising the expression cassette.

* * * * *

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: A synthetic primer

<400> SEQUENCE: 1
ccatgatatg ctacggggat                                              20

<210> SEQ ID NO 2
```

```
<211> LENGTH: 20
<212> TYPE: DNA
<213> ORGANISM: Artificial Sequence
<220> FEATURE:
<223> OTHER INFORMATION: A synthetic primer

<400> SEQUENCE: 2
gactcaacat ctggtagcct                                            20

<210> SEQ ID NO 3
<211> LENGTH: 16
<212> TYPE: PRT
<213> ORGANISM: Turkey Astrovirus-2

<400> SEQUENCE: 3

Arg Ser Arg Thr Lys Lys Thr Val Lys Ile Ile Glu Lys Lys Pro Glu
 1               5                  10                  15

<210> SEQ ID NO 4
<211> LENGTH: 19
<212> TYPE: PRT
<213> ORGANISM: Turkey Astrovirus-2

<400> SEQUENCE: 4

His Pro Arg Ser Ala Leu Gly Pro Arg Gln Gly Trp Trp Asn Val Asp
 1               5                  10                  15

Pro Gly Asp

<210> SEQ ID NO 5
<211> LENGTH: 16
<212> TYPE: PRT
<213> ORGANISM: Turkey Astrovirus-2

<400> SEQUENCE: 5

Lys His Leu Glu Glu Glu Lys Asn Tyr Trp Lys Asn Gln Cys Glu Arg
 1               5                  10                  15

<210> SEQ ID NO 6
<211> LENGTH: 7355
<212> TYPE: DNA
<213> ORGANISM: Turkey astrovirus

<400> SEQUENCE: 6
ccgaaagtgt tgtcggggcg atggcccagg cgggtcgcag tggcgatgct tttgcatccc    60
ttgatcaacg gcgggagcgc caagaagaac aggcgcagtc cggccttgac aaggtgttct   120
acttccaagg cgtggttgaa ctattcaacc gtatgaaaat cgcctatgga aggacaccgg   180
cttggacggc cctcatgaag tgtaacgcca tatacttgaa agattttaaa acagcagttg   240
gcgttgaggg taccgctat gggctctttt tcgcagaaga agtgactaaa ccaacttggt   300
cacccgacat tggagcaaac ttgataactt gggcgaaaa ggcctgttta gacgcccaaa   360
atgcaaaata tgaaagattg caagcctcac ttaaaacaac tagtggcctt gtgcatcaag   420
tgatggaaaa aactagggaa gctaaagaga acctagagaa agccaataag atccaagagc   480
aacttgacaa ggtcattgag agcaacaaag ctttacaccg taagatacag gagagaaacc   540
gagaaaagat gcaggaatac atggtaaggt tgcataacac gcagaaagat cgtgatgatt   600
gggttcagag atgctccagg ttagaacagg agaatgtcac attgcagaaa aggttgaagg   660
agaaagagaa cgcgctggta tctgttgggt gggatctttt aggctggata gttatttcag   720
tgcttgtatt cggcctgatt tcactcgcag acgcgcaaaa cttgactcca ccagccaaga   780
```

-continued

```
ttgtgataac tccagggcaa gcagagttca tggacctagc taaattggaa aaaatccagg      840
tcagaaagta ccgactggat agttgtgaat taccacctga gaaaggttgc gtgttgtaca      900
aggattacct taccaccagg ccggtaagct ttttggagtt gatggccaaa tgttcaaaac      960
ctgactgggt ctcggagagc agttacaatg aaacaaccct aatggaagaa tgcatccaga     1020
tctttggtgc agagtggtgt gaagggaagc tcgttgatct tgtaccaaga agtgtggcg      1080
agcaacatgt cttagttaac atcatagagc aaattgaaaa aaccagagaa gttgtgaccc     1140
ttatatatgg taaggtgatg tcatacaggc tagatatgtg gataacatct attttagtt      1200
tagttttggc aggtaataag gaaaaattgt ttaaaatggc tcccttcatt tttgtagcat     1260
ggttttaaa cataccagtg tttttaactt gtgtggcagt caacattttt ccagttgttt      1320
ccctgccttt cattttgttc cagatttta tgccacagtt tgttttggta aatgcctttc      1380
ttctatggtt aacactcact ttaacagcat tttattggag tgaggggccc aaaatactga     1440
tggagataag ttatgccctt gtgtatacca tcggctttgt tttatggtcc cttggactag     1500
ctgtgggggt gacgctcaaa ttgacaatgg tacatcagat attaatgttt tgtgttgttg     1560
ccgcagctat ttgcggaacc aagtttgcat gcacaacaat aacagtgcaa cacccagatg     1620
gaacaaccgc aaaatacacc cgggttggta agctaaagaa taatgttgtg aaccagtgca     1680
aaaaggtagt cacgacattg cagacaagag gcgttatacc agcaacgcct gcgaaaacag     1740
catctattgt tattgttgag ggcaaaaatg gaacaggtgt tgggttcagg tttatgaatt     1800
atattcttac agcagaacac gtggttcagg gatcagatat agcaacactt aaaaatggca     1860
gtgttagtgt gaaatccaaa gtcatcaaaa cgatcccaat atttgagagt gttgacaatg     1920
ttgcagtgtt aaaattgcca cctgagctca atagcgtgaa gcctatcaaa ttagcaaaga     1980
aggttcaaag tgactatctg acactgacag cctatgatcc aaattttcaa catgccgcca     2040
cttttaccgg gtggtgtatt atagatgaa attggcttaa taactccttt gatacaaaat      2100
ttgggaatag tggtgcacct tattgtgatc atgatggtag gctagttggt atccacctag     2160
gcacacaggt tgttctttcc caaggcatag tcattgtaga cgcattgaaa aatacattcc     2220
agcttgcgga tcagtgtaga ccacagaatt ttgacatgga tgagttcctt gagaaagtta     2280
tagcaggaac aaaagtgtca catgcagcga tcctaaaaga actggaagaa cttagagaag     2340
aggtgcaatt tttaaagaaa aaatgtgtca cctatgatga ctactggcta tgccaaacca     2400
tctttgggca ggccaaaggg aagacgaaga aaacagtcag aggccgtaaa caccttgtta     2460
ccaaaagagc tcttgggaaa ggccacttca tgaagatgag gatgctcact gatgaagaat     2520
atcagaatat gattgaaaag ggcttctcag cagaggaaat aagggaggca gtcaacgcac     2580
tccgagaaca agcatggctt aattattgta ttgataatga tgttgatgac gaaggtgagg     2640
aagattggta tgatgacatg gtagagacag atagagttaa ccaggagatc gatgaggcca     2700
tagagcgggc catggaagat cgtggtgagt tctaccagaa gaaatcccgc cttacctttg     2760
ttgaacaggc catgatgcat ttgattcaag tgagcaagga gagaagccag actgctaaac     2820
tagaagttca aaaggagaat gaagcccaac tagtgaagat gtttgagcgg tgtgtcacag     2880
atgagaatac acctgagggt accacctcta tagcggcttt gtccacagaa gatgatgtta     2940
ggcttgttga agggaaagtc attgatttca ccaaagcaaa gaacatccca gttgacgggg     3000
aaattaggag agagatcatc cctggaacaa aatgtactga gatttccact ggacctgaaa     3060
ataagaagaa catattgaag aaaaaggata cacacatagc tgagggtaaa gttgaaacta     3120
agtcatcaca gcagccggtt gacgtcaagg atgataaacc cgtagccttg aacaacgta     3180
```

```
agcctagagc ttgtaaatgg tgcggttcat cacagaaaca tgattaccgg gaatgtcggt    3240
ttcaacgtga aaacgctttt tgtgtgtatt gtgcagctat gcactcaatg tttgagggcc    3300
atataagacc aatagagtgc actagttgca agaaaagttt ttcaggaatt gagaagttag    3360
aagatcatgt ggtcagtgga gagtgtcaaa aaaactaata gagggcctg tgacaacaaa     3420 ggcccctacc cccgtaccag attggcttaa aatatttgca tgggaagatg acatattacc    3480
acctgaaggt aaaactgcct taccagaaaa tgttactcta attggacata taccagttga    3540
taagttggtc tcgcgcacca agaaagtcca ggatccatta ttaggccttg taacaccatg    3600
gaaacaagat atgtatgatt caacaacatg gactgtaaag gcttacacca aatgtttga    3660 gaaattccat taccacgacc cagttgactt tgtggaacag tatgctgagt ttgtgctgtt    3720
gtgtgacaat atggtgttga gagagcatga ctatatggca aatagcaaca tcacaccaat    3780
catgtcaaca gagaaaaatg tcaatagtac accagcatac ccaaaattcc aagcctatga    3840
cagcgaagcc gagtatttgg aagattgtgg gtggcaagag tacctggatg ttgtgtctga    3900
tccagaaact ataaatcgta gaccccctatg gtggtgcttc ctcaaaaatg aagttctcaa    3960
aagagagaaa attgaggaca gtgacattcg aatgatattg tgcaccgacc cgattttac     4020 caggattggg gctatgtttg agcaggatca gaacaacaga atgaaacaac agactgaaat    4080
aaggtctgca caggtcggat ggaccccctt tttcggcggc ttggatcgca gggttcgcag    4140
gttgtatggt gatggagata ggtattttgt tgagatggac tggacacggt atgatgggac    4200
tataccaaaa tcactatttt ggagaattag gcaaatcagg ttcttcttcc tccatgattc    4260
tcataagact ccaaagatgc ggcgcttgta caactggtat gtgaaaaatc tgttggaaaa    4320 aattattta ttgccaactg gagaagtttg ccaggtcaag aaaggaaatc caagtggtca     4380 gtttcaaca actgtggata ataatatgat caatgtctgg ctaacaacat ttgaggtttc    4440
atacctattt ttcaaacagc gtggtagact gccaacagag aaagagctgc aagagaactg    4500
ctccatgata tgctacgggg atgacagact tctttccatc cgtaaagggt tgttgagta    4560 cgaacctgat acagtcattg atatgtacaa aaacatcttt ggaatgtggg tgaaaagaaa    4620
caacatcaaa atccaagata cacctgaagg gctctctttt tgtgggctta caatagtaaa    4680
atcaagtact ggtgcatatg ttggtgttcc caatgtgaac aaaaatactgt caactttgga    4740 aaatccagta cgtaggctac cagatgttga gtctcttttgg ggtaaattgg ttccctgcg    4800 catattgtgt gaaaatgctc ccagcaatgt taaacactt cttgatgagc agattagcaa    4860
tgttgaggag ttcgccgcca gagaaaacat acaacttcct gaggtcgggc ccgacttcta    4920
ttccagaata tggtgagagg aggaccgaaa gaagatggcg gcgatggccg acaaggtcgt    4980
tgtcaagaag acaactacaa ggcgcagggg caggagtaat tcccgctccc gtagcaggag    5040
taggagcagg agcagaacta aaagacagt caaaattatt gagaaaaagc cagaaaaatc      5100
catcctaaag aaaattgatc aggctgaaag aagagatgca aaacagctta ggcggattcg    5160
taagaaagtg cagggaccgc cagtaaaattc caggatgaca acagtagtca cacttggtca    5220
gataacaggc aataaagaca cacccctaga gcggaaacac aagtgctttc tgaatccgct    5280
gttgatgaag agtcaggaaa ctggtcaaac tgcaacaccc ttatctgtta ggcatcccaa    5340
atataatctg tggaagctat ccagactcca tgtcagactt atacccttg caggaaagc     5400 gaatattttg gggtcagtgg tgttcttaga tcttgaacag gaggcaaaca cagcaggacc    5460
agaatcagta gataccatca aggcaagacc ccatgttgaa gttcccatag ggtcgaaaac    5520
```

-continued

```
cgtttggaaa gtgcacccta gaagcgctct aggacctaga cagggtggt ggaatgttga    5580
ccctggtgac agcccaactg attctcttgg gccagcactc aacatgtgga cctacctgca   5640
aactgtcaat gcactccaga gcgctggggg cactcaaacg ccttacacca gtgcactttt   5700
tcttgtggag gtcttggtca cttatgagtt ttcaaactat ggcccaaagc ctgcactgtc   5760
tcaaatggta tcagacagct ttccaccagc ctccggttct actgcaacct taaaaaacac   5820
cagtgatggg gctgtagcaa tacaactctc aggcgctatc gcccgaaaga tggaggaggt   5880
tgagcccaag ggtaggcgct caaatgcgca acatcaggt gtcggtgaag tgttctgggc    5940
agtgtccact gaagtagtca atacagtagc agatgccata ccaggctggg gctggctcct   6000
gaaaggtggc tggtttgtcc ttaggaaaat ctttggggcc gcaaatgacc agaatggcac   6060
ttacttgata tactcttcag tggcagatgc acaaggtgac aacaggatat acacatcagt   6120
gaaacagaca cagttgacat caagcaggat caacctcgtc caactcaccc agcccaatgt   6180
gaaccaagca gcagtaggtg gcagtgttgg tgcggcaaac tccatctatt tgccactacc   6240
acaagcagat gaccaataca cccctactt tgtctataat tttcaagggg aaagggtgtc    6300
aaccaccgag actggggtat tttgtctggc agccatacca gctgcgacta catctagtag   6360
gtataataat cagatcacca ctccatcaat ggctacagg aatgctagtg gtacaggaac    6420
atcattccta ctagatgctg catcatggtg gaatatattg gatgtaactc agactggagt   6480
gcttttttgga caaccaagat tgggtgttgg tgtcatgcag acaatgaaga ctctcaaaca  6540
gcatatcaag gattacacag agcctgcaat acagaaatat tatcctggaa caactaacct   6600
tgatgagcag ttgaagcaga gattgaacct ggcagagggt gacccggtca tctcaatggg   6660
ggacacaaac ggtaggaggg ctgcactctt ttataggact agtgatgaaa atatatattt   6720
atttttctca accacagaag atccaggggc acagtatcaa aatctgaaaa tgttgtactt   6780
ctggaactgg tcctattctg acacaaaaca gcaattttg gaccaccta gaacagtgca    6840
gtttgcaaat ttgatgaca gccagccagc ccctatgat agtgatgatg atgaccttc     6900
tgatgtaaca tcacttttg agcaggctga tttgggggat gagacagact tcaaatttaa   6960
tatgtccatc caaacctcca acatcttga ggaggagaaa aattactgga aaaccagtg    7020
tgagaggatg atgatggaga aggcccttc gggcacctca cagcctcttg tccggtttga   7080
gaaagctgga cctagggcag accaatcttc tgccagtggt cattcttgaa tggccacact   7140
ttctctgcgg tggaaatgga aatcaccatt ccacctaaga tgattagccg atccaacgga   7200
aatcacccgt gggtggtgc gcggtttacg catcgggaaa tcaacccggt gtattacccg    7260
cacttccggc tcaacagttt tttaaaactg atataaattt atgaaatttt tattagcatt   7320
ttaagaaaaa aaaaaaaaaa aaaaaaaaaa aaaaa                              7355
```

<210> SEQ ID NO 7
<211> LENGTH: 1125
<212> TYPE: PRT
<213> ORGANISM: Turkey astrovirus

<400> SEQUENCE: 7

```
Met Ala Gln Ala Gly Arg Ser Gly Asp Ala Phe Ala Ser Leu Asp Gln
 1               5                  10                  15

Arg Arg Glu Arg Gln Glu Glu Gln Ala Gln Ser Gly Leu Asp Lys Val
            20                  25                  30

Phe Tyr Phe Gln Gly Val Val Glu Leu Phe Asn Arg Met Lys Ile Ala
        35                  40                  45
```

```
Tyr Gly Arg Thr Pro Ala Trp Thr Ala Leu Met Lys Cys Asn Ala Ile
         50                  55                  60
Tyr Leu Lys Asp Phe Lys Thr Ala Val Gly Val Glu Gly Thr Arg Tyr
 65                  70                  75                  80
Gly Leu Phe Phe Ala Glu Glu Val Thr Lys Pro Thr Trp Ser Pro Asp
                     85                  90                  95
Ile Gly Ala Asn Leu Ile Thr Leu Gly Glu Lys Ala Cys Leu Asp Ala
                 100                 105                 110
Gln Asn Ala Lys Tyr Glu Arg Leu Gln Ala Ser Leu Lys Thr Thr Ser
             115                 120                 125
Gly Leu Val His Gln Val Met Glu Lys Thr Arg Glu Ala Lys Glu Asn
         130                 135                 140
Leu Glu Lys Ala Asn Lys Ile Gln Glu Gln Leu Asp Lys Val Ile Glu
145                 150                 155                 160
Ser Asn Lys Ala Leu His Arg Lys Ile Gln Glu Arg Asn Arg Glu Lys
                     165                 170                 175
Met Gln Glu Tyr Met Val Arg Leu His Asn Thr Gln Lys Asp Arg Asp
                 180                 185                 190
Asp Trp Val Gln Arg Cys Ser Arg Leu Glu Gln Glu Asn Val Thr Leu
             195                 200                 205
Gln Lys Arg Leu Lys Glu Lys Glu Asn Ala Leu Val Ser Val Gly Trp
         210                 215                 220
Asp Leu Leu Gly Trp Ile Val Ile Ser Val Leu Val Phe Gly Leu Ile
225                 230                 235                 240
Ser Leu Ala Asp Ala Gln Asn Leu Thr Pro Pro Ala Lys Ile Val Ile
                     245                 250                 255
Thr Pro Gly Gln Ala Glu Phe Met Asp Leu Ala Lys Leu Glu Lys Ile
                 260                 265                 270
Gln Val Arg Lys Tyr Arg Leu Asp Ser Cys Glu Leu Pro Pro Glu Lys
             275                 280                 285
Gly Cys Val Leu Tyr Lys Asp Tyr Leu Thr Thr Arg Pro Val Ser Phe
         290                 295                 300
Leu Glu Leu Met Ala Lys Cys Ser Lys Pro Asp Trp Val Ser Glu Ser
305                 310                 315                 320
Ser Tyr Asn Glu Thr Thr Leu Met Glu Glu Cys Ile Gln Ile Phe Gly
                     325                 330                 335
Ala Glu Trp Cys Glu Gly Lys Leu Val Asp Leu Val Pro Arg Lys Cys
                 340                 345                 350
Gly Glu Gln His Val Leu Val Asn Ile Ile Glu Gln Ile Glu Lys Thr
             355                 360                 365
Arg Glu Val Val Thr Leu Ile Tyr Gly Lys Val Met Ser Tyr Arg Leu
         370                 375                 380
Asp Met Trp Ile Thr Ser Ile Phe Ser Leu Val Leu Ala Gly Asn Lys
385                 390                 395                 400
Glu Lys Leu Phe Lys Met Ala Pro Phe Ile Phe Val Ala Trp Phe Leu
                     405                 410                 415
Asn Ile Pro Val Phe Leu Thr Cys Val Ala Asn Ile Phe Pro Val
                 420                 425                 430
Val Ser Leu Pro Phe Ile Leu Phe Gln Ile Phe Met Pro Gln Phe Val
             435                 440                 445
Leu Val Asn Ala Phe Leu Leu Trp Leu Thr Leu Thr Leu Thr Ala Phe
         450                 455                 460
Tyr Trp Ser Glu Gly Pro Lys Ile Leu Met Glu Ile Ser Tyr Ala Leu
```

-continued

```
            465                 470                 475                 480
Val Tyr Thr Ile Gly Phe Val Leu Trp Ser Leu Gly Leu Ala Val Gly
                    485                 490                 495
Val Thr Leu Lys Leu Thr Met Val His Gln Ile Leu Met Phe Cys Val
                500                 505                 510
Val Ala Ala Ile Cys Gly Thr Lys Phe Ala Cys Thr Thr Ile Thr
                515                 520                 525
Val Gln His Pro Asp Gly Thr Thr Ala Lys Tyr Thr Arg Val Gly Lys
            530                 535                 540
Leu Lys Asn Asn Val Val Asn Gln Cys Lys Lys Val Val Thr Thr Leu
545                 550                 555                 560
Gln Thr Arg Gly Val Ile Pro Ala Thr Pro Ala Lys Thr Ala Ser Ile
                    565                 570                 575
Val Ile Val Glu Gly Lys Asn Gly Thr Gly Val Gly Phe Arg Phe Met
                580                 585                 590
Asn Tyr Ile Leu Thr Ala Glu His Val Val Gln Gly Ser Asp Ile Ala
                595                 600                 605
Thr Leu Lys Asn Gly Ser Val Ser Val Lys Ser Lys Val Ile Lys Thr
            610                 615                 620
Ile Pro Ile Phe Glu Ser Val Asp Asn Val Ala Val Leu Lys Leu Pro
625                 630                 635                 640
Pro Glu Leu Asn Ser Val Lys Pro Ile Lys Leu Ala Lys Lys Val Gln
                    645                 650                 655
Ser Asp Tyr Leu Thr Leu Thr Ala Tyr Asp Pro Asn Phe Gln His Ala
                660                 665                 670
Ala Thr Phe Thr Gly Trp Cys Ile Ile Asp Gly Asn Trp Leu Asn Asn
            675                 680                 685
Ser Phe Asp Thr Lys Phe Gly Asn Ser Gly Ala Pro Tyr Cys Asp His
            690                 695                 700
Asp Gly Arg Leu Val Gly Ile His Leu Gly Thr Gln Gly Val Leu Ser
705                 710                 715                 720
Gln Gly Ile Val Ile Val Asp Ala Leu Lys Asn Thr Phe Gln Leu Ala
                    725                 730                 735
Asp Gln Cys Arg Pro Gln Asn Phe Asp Met Asp Glu Phe Leu Glu Lys
                740                 745                 750
Val Ile Ala Gly Thr Lys Val Ser His Ala Ala Ile Leu Lys Glu Leu
            755                 760                 765
Glu Glu Leu Arg Glu Glu Val Gln Phe Leu Lys Lys Lys Cys Val Thr
            770                 775                 780
Tyr Asp Asp Tyr Trp Leu Cys Gln Thr Ile Phe Gly Gln Ala Lys Gly
785                 790                 795                 800
Lys Thr Lys Lys Thr Val Arg Gly Arg Lys His Leu Val Thr Lys Arg
                    805                 810                 815
Ala Leu Gly Lys Gly His Phe Met Lys Met Arg Met Leu Thr Asp Glu
                820                 825                 830
Glu Tyr Gln Asn Met Ile Glu Lys Gly Phe Ser Ala Glu Glu Ile Arg
            835                 840                 845
Glu Ala Val Asn Ala Leu Arg Glu Gln Ala Trp Leu Asn Tyr Cys Ile
            850                 855                 860
Asp Asn Asp Val Asp Asp Glu Gly Glu Glu Asp Trp Tyr Asp Asp Met
865                 870                 875                 880
Val Glu Thr Asp Arg Val Asn Gln Glu Ile Asp Glu Ala Ile Glu Arg
                    885                 890                 895
```

```
Ala Met Glu Asp Arg Gly Glu Phe Tyr Gln Lys Lys Ser Arg Leu Thr
            900                 905                 910

Phe Val Glu Gln Ala Met Met His Leu Ile Gln Val Ser Lys Glu Arg
            915                 920                 925

Ser Gln Thr Ala Lys Leu Glu Val Gln Lys Glu Asn Glu Ala Gln Leu
            930                 935                 940

Val Lys Met Phe Glu Arg Cys Val Thr Asp Asn Thr Pro Glu Gly
945                 950                 955                 960

Thr Thr Ser Ile Ala Ala Leu Ser Thr Glu Asp Val Arg Leu Val
                965                 970                 975

Glu Gly Lys Val Ile Asp Phe Thr Lys Ala Lys Asn Ile Pro Val Asp
                980                 985                 990

Gly Glu Ile Arg Arg Glu Ile Ile Pro Gly Thr Lys Cys Thr Glu Ile
                995                 1000                1005

Ser Thr Gly Pro Glu Asn Lys Lys Asn Ile Leu Lys Lys Lys Asp Thr
        1010                1015                1020

His Ile Ala Glu Gly Lys Val Glu Thr Lys Ser Ser Gln Gln Pro Val
1025                1030                1035                1040

Asp Val Lys Asp Lys Pro Val Ala Leu Glu Gln Arg Lys Pro Arg
        1045                1050                1055

Ala Cys Lys Trp Cys Gly Ser Ser Gln Lys His Asp Tyr Arg Glu Cys
        1060                1065                1070

Arg Phe Gln Arg Glu Lys Arg Phe Cys Val Tyr Cys Ala Ala Met His
        1075                1080                1085

Ser Met Phe Glu Gly His Ile Arg Pro Ile Glu Cys Thr Ser Cys Lys
        1090                1095                1100

Lys Ser Phe Ser Gly Ile Glu Lys Leu Glu Asp His Val Val Ser Gly
1105                1110                1115                1120

Glu Cys Gln Lys Asn
                1125

<210> SEQ ID NO 8
<211> LENGTH: 527
<212> TYPE: PRT
<213> ORGANISM: Turkey astrovirus

<400> SEQUENCE: 8

Glu Val Arg Arg Ser Cys Gly Gln Trp Arg Val Ser Lys Lys Leu Ile
1               5                   10                  15

Glu Gly Pro Val Thr Thr Lys Ala Pro Thr Pro Val Pro Asp Trp Leu
            20                  25                  30

Lys Ile Phe Ala Trp Glu Asp Asp Ile Leu Pro Glu Gly Lys Thr
        35                  40                  45

Ala Leu Pro Glu Asn Val Thr Leu Ile Gly His Ile Pro Val Asp Lys
    50                  55                  60

Leu Val Ser Arg Thr Lys Lys Val Gln Asp Pro Leu Leu Gly Leu Val
65                  70                  75                  80

Thr Pro Trp Lys Gln Asp Met Tyr Asp Ser Thr Thr Trp Thr Val Lys
                85                  90                  95

Ala Tyr Thr Lys Met Phe Glu Lys Phe His Tyr His Asp Pro Val Asp
            100                 105                 110

Phe Val Glu Gln Tyr Ala Glu Phe Val Leu Leu Cys Asp Asn Met Val
        115                 120                 125

Leu Arg Glu His Asp Tyr Met Ala Asn Ser Asn Ile Thr Pro Ile Met
```

-continued

```
                130                 135                 140
Ser Thr Glu Lys Asn Val Asn Ser Thr Pro Ala Tyr Pro Lys Phe Gln
145                 150                 155                 160

Ala Tyr Asp Ser Glu Ala Glu Tyr Leu Glu Asp Cys Gly Trp Gln Glu
                165                 170                 175

Tyr Leu Asp Val Val Ser Asp Pro Glu Thr Ile Asn Arg Arg Pro Leu
            180                 185                 190

Trp Trp Cys Phe Leu Lys Asn Glu Val Leu Lys Arg Glu Lys Ile Glu
                195                 200                 205

Asp Ser Asp Ile Arg Met Ile Leu Cys Thr Asp Pro Ile Phe Thr Arg
210                 215                 220

Ile Gly Ala Met Phe Glu Gln Asp Gln Asn Asn Arg Met Lys Gln Gln
225                 230                 235                 240

Thr Glu Ile Arg Ser Ala Gln Val Gly Trp Thr Pro Phe Phe Gly Gly
                245                 250                 255

Leu Asp Arg Arg Val Arg Arg Leu Tyr Gly Asp Gly Asp Arg Tyr Phe
                260                 265                 270

Val Glu Met Asp Trp Thr Arg Tyr Asp Gly Thr Ile Pro Lys Ser Leu
            275                 280                 285

Phe Trp Arg Ile Arg Gln Ile Arg Phe Phe Phe Leu His Asp Ser His
            290                 295                 300

Lys Thr Pro Lys Met Arg Arg Leu Tyr Asn Trp Tyr Val Lys Asn Leu
305                 310                 315                 320

Leu Glu Lys Ile Ile Leu Leu Pro Thr Gly Glu Val Cys Gln Val Lys
                325                 330                 335

Lys Gly Asn Pro Ser Gly Gln Phe Ser Thr Thr Val Asp Asn Asn Met
                340                 345                 350

Ile Asn Val Trp Leu Thr Thr Phe Glu Val Ser Tyr Leu Phe Phe Lys
                355                 360                 365

Gln Arg Gly Arg Leu Pro Thr Glu Lys Glu Leu Gln Glu Asn Cys Ser
                370                 375                 380

Met Ile Cys Tyr Gly Asp Asp Arg Leu Leu Ser Ile Arg Lys Gly Phe
385                 390                 395                 400

Val Glu Tyr Glu Pro Asp Thr Val Ile Asp Met Tyr Lys Asn Ile Phe
                405                 410                 415

Gly Met Trp Val Lys Arg Asn Asn Ile Lys Ile Gln Asp Thr Pro Glu
                420                 425                 430

Gly Leu Ser Phe Cys Gly Leu Thr Ile Val Lys Ser Ser Thr Gly Ala
                435                 440                 445

Tyr Val Gly Val Pro Asn Val Asn Lys Ile Leu Ser Thr Leu Glu Asn
450                 455                 460

Pro Val Arg Arg Leu Pro Asp Val Glu Ser Leu Trp Gly Lys Leu Val
465                 470                 475                 480

Ser Leu Arg Ile Leu Cys Glu Asn Ala Pro Ser Asn Val Lys His Phe
                485                 490                 495

Leu Asp Glu Gln Ile Ser Asn Val Glu Glu Phe Ala Ala Arg Glu Asn
                500                 505                 510

Ile Gln Leu Pro Glu Val Gly Pro Asp Phe Tyr Ser Arg Ile Trp
                515                 520                 525
```

<210> SEQ ID NO 9
<211> LENGTH: 724
<212> TYPE: PRT
<213> ORGANISM: Turkey astrovirus

<400> SEQUENCE: 9

```
Met Ala Ala Met Ala Asp Lys Val Val Lys Lys Thr Thr Thr Arg
 1               5                  10                  15
Arg Arg Gly Arg Ser Asn Ser Arg Ser Arg Ser Arg Ser Arg
             20                  25                  30
Ser Arg Thr Lys Lys Thr Val Lys Ile Ile Glu Lys Lys Pro Glu Lys
             35                  40                  45
Ser Ile Leu Lys Lys Ile Asp Gln Ala Glu Arg Arg Asp Ala Lys Gln
         50                  55                  60
Leu Arg Arg Ile Arg Lys Val Gln Gly Pro Val Asn Ser Arg
 65                  70                  75                  80
Met Thr Thr Val Val Thr Leu Gly Gln Ile Thr Gly Asn Lys Asp Asn
                 85                  90                  95
Thr Leu Glu Arg Lys His Lys Cys Phe Leu Asn Pro Leu Leu Met Lys
            100                 105                 110
Ser Gln Glu Thr Gly Gln Thr Ala Thr Pro Leu Ser Val Arg Ala Ser
            115                 120                 125
Gln Tyr Asn Leu Trp Lys Leu Ser Arg Leu His Val Arg Leu Ile Pro
        130                 135                 140
Leu Ala Gly Lys Ala Asn Ile Leu Gly Ser Val Val Phe Leu Asp Leu
145                 150                 155                 160
Glu Gln Glu Ala Asn Thr Ala Gly Pro Glu Ser Val Asp Thr Ile Lys
                165                 170                 175
Ala Arg Pro His Val Glu Val Pro Ile Gly Ser Lys Thr Val Trp Lys
            180                 185                 190
Val His Pro Arg Ser Ala Leu Gly Pro Arg Gln Gly Trp Trp Asn Val
        195                 200                 205
Asp Pro Gly Asp Ser Pro Thr Asp Ser Leu Gly Pro Ala Leu Asn Met
210                 215                 220
Trp Thr Tyr Leu Gln Thr Val Asn Ala Leu Gln Ser Ala Gly Gly Thr
225                 230                 235                 240
Gln Thr Pro Tyr Thr Ser Ala Leu Phe Leu Val Glu Val Leu Val Thr
                245                 250                 255
Tyr Glu Phe Ser Asn Tyr Gly Pro Lys Pro Ala Leu Ser Gln Met Val
            260                 265                 270
Ser Asp Ser Phe Pro Pro Ala Ser Gly Ser Thr Ala Thr Leu Lys Asn
        275                 280                 285
Thr Ser Asp Gly Ala Val Ala Ile Gln Leu Ser Gly Ala Ile Ala Arg
290                 295                 300
Lys Met Glu Glu Val Glu Pro Lys Gly Arg Arg Ser Asn Ala Gln Thr
305                 310                 315                 320
Ser Gly Val Gly Glu Val Phe Trp Ala Val Ser Thr Glu Val Val Asn
                325                 330                 335
Thr Val Ala Asp Ala Ile Pro Gly Trp Gly Trp Leu Leu Lys Gly Gly
            340                 345                 350
Trp Phe Val Leu Arg Lys Ile Phe Gly Ala Ala Asn Asp Gln Asn Gly
        355                 360                 365
Thr Tyr Leu Ile Tyr Ser Ser Val Ala Asp Ala Gln Gly Asp Asn Arg
    370                 375                 380
Ile Tyr Thr Ser Val Lys Gln Thr Gln Leu Thr Ser Ser Arg Ile Asn
385                 390                 395                 400
Leu Val Gln Leu Thr Gln Pro Asn Val Asn Gln Ala Ala Val Gly Gly
```

-continued

```
                    405                 410                 415
Ser Val Gly Ala Ala Asn Ser Ile Tyr Leu Pro Leu Pro Gln Ala Asp
                420                 425                 430

Asp Gln Tyr Thr Pro Tyr Phe Val Tyr Asn Phe Gln Gly Glu Arg Val
            435                 440                 445

Ser Thr Thr Glu Thr Gly Val Phe Cys Leu Ala Ala Ile Pro Ala Ala
        450                 455                 460

Thr Thr Ser Ser Arg Tyr Asn Asn Gln Ile Thr Thr Pro Ser Ile Gly
465                 470                 475                 480

Tyr Arg Asn Ala Ser Gly Thr Gly Thr Ser Phe Leu Leu Asp Ala Ala
                485                 490                 495

Ser Trp Trp Asn Ile Leu Asp Val Thr Gln Thr Gly Val Leu Phe Gly
                500                 505                 510

Gln Pro Arg Leu Gly Val Gly Val Met Gln Thr Met Lys Thr Leu Lys
            515                 520                 525

Gln His Ile Lys Asp Tyr Thr Glu Pro Ala Ile Gln Lys Tyr Tyr Pro
        530                 535                 540

Gly Thr Thr Asn Leu Asp Glu Gln Leu Lys Gln Arg Leu Asn Leu Ala
545                 550                 555                 560

Glu Gly Asp Pro Val Ile Ser Met Gly Asp Thr Asn Gly Arg Arg Ala
                565                 570                 575

Ala Leu Phe Tyr Arg Thr Ser Asp Glu Lys Tyr Ile Leu Phe Phe Ser
                580                 585                 590

Thr Thr Glu Asp Pro Gly Ala Gln Tyr Gln Asn Leu Lys Met Leu Tyr
            595                 600                 605

Phe Trp Asn Trp Ser Tyr Ser Asp Thr Lys Gln Gln Phe Leu Asp His
        610                 615                 620

Leu Arg Thr Val Gln Phe Ala Asn Leu Asp Asp Ser Gln Pro Ala Pro
625                 630                 635                 640

Tyr Asp Ser Asp Asp Asp Leu Ser Asp Val Thr Ser Leu Phe Glu
                645                 650                 655

Gln Ala Asp Leu Gly Asp Glu Thr Asp Phe Lys Phe Asn Met Ser Ile
            660                 665                 670

Gln Thr Ser Lys His Leu Glu Glu Lys Asn Tyr Trp Lys Asn Gln
        675                 680                 685

Cys Glu Arg Met Met Met Glu Lys Ala Leu Ser Gly Thr Ser Gln Pro
690                 695                 700

Leu Val Arg Phe Glu Lys Ala Gly Pro Arg Ala Asp Gln Ser Ser Ala
705                 710                 715                 720

Ser Gly His Ser
```

<210> SEQ ID NO 10
<211> LENGTH: 2175
<212> TYPE: DNA
<213> ORGANISM: Turkey astrovirus-2

<400> SEQUENCE: 10

```
atggcggcga tggccgacaa ggtcgttgtc aagaagacaa ctacaaggcg caggggcagg     60
agtaattccc gctcccgtag caggagtagg agcaggagca gaactaaaaa gacagtcaaa    120
attattgaga aaaagccaga aaatccatc taaagaaaa ttgaccaggc tgaaagaaga      180
gatgaaaagc aaattaggcg aatgcggaaa aaattgcagg ggccaccagt aaattccagg    240
atgacaacag tagtcacact tggtcagata acaggcaata aagacaacac cttagagcgg    300
```

-continued

```
aaacacaagg ttttttctgaa tccactgttg atgaagagtc aggaaactgg tcaaactgca      360
acacccttgt ctgttagagc atcccaatac aatctgtgga agctatccag actccatgtc      420
agacttatac cccttgcagg aaaagcgaat attctgggt cagtggtgtt tctagatctt       480
gaacaagagg caaatacagc aggaccagaa tcagtagata ccatcaaagc aagaccccat      540
gttgaagttc catagggtc gaaaactgtt tggaaagtgc acccctagaag tgctctgggg     600
cctagacagg ggtggtggaa tgttgaccct ggtgacagcc caactgattc ccttgggcca     660
gcactcaaca tgtggaccta cctgcaaact gttaatgcac tccagagcgc tgggggcaac    720
caaacacctt acaccagtgc acttttcctt gtggaggtct tggttaccta tgagttttca    780
aattatggtc caaagcctgc actgtcccaa atgatatcgg acagttttcc accagcctcc    840
ggttctactg caactcttaa aaacaccagt gatggggctg tagcaataca actttcaggc    900
gctatcgccc gaaaaatgga ggagcttgag cctaagggta gatgctcaaa tgcacagaca    960
tcaggtgttg gagaagtgtt tgggcagtg tcaactgagg tggttaacac agtagcagat    1020
gctataccag gttggggttg gctcttgaaa ggtggctggt ttgtccttag aaaattattt   1080
ggagctgcga atgacgcaaa tggcacctac ctgttatatt catcggtggc cgatgcacag   1140
caggataaca gattatatac aaaagtgaaa caaggacaat taacatcgag tgtgatcaac   1200
ctcgtccaac tcactcagcc aatgtgaac caagcagcag taggtggcag tgttggctcg    1260
gcaaattcca tctatttgcc attaccacaa gcagatgacc aatatacacc ccatcttgtt  1320
tatgatttcc aagggaatag ggtgtcaacc gctgagactg gggtattttg tctggcatcc   1380
ataccagccg caactacatc cagtaggtac aatggtcaaa tcaccagtcc ttcaattggc   1440
tataagagtg ctagtggcac aggaacatct ttctcactag atgaagcatc atggtggaac   1500
atcttggatg taactcagac tggggtcctc tttggacaac caaaattggg cattggtgtc   1560
atgcaaacaa tgaagaccct taaacaacac atcagggatt atacagagcc tgcaataaaa   1620
aaatattacc ctggaacaac taacattgct gaagaattga acagaggat gaaactggca    1680
gagggtgatc cggtcatctc gatgggagac acaaatggta ggagagctgc actttttat    1740
aggactagtg atgaaaggta cattttgttc ttttcaacaa caggagatcc agggtcacaa   1800
tttgaaaatt tgaagatgtt gtacttttgg aactggtcct attctgacaa caaacagcaa   1860
tttctggacc gccttagaac agtgcaattt gcaaatgcgg atgacagcca gccaacccct   1920
tgtgatagtg atgatgatga cctctctgat gtaacatcac tcttgagca ggctgatttg     1980
ggggatgaga cagatttcaa atttaatatg tccatccaga cctccaaaca tcttgaggag   2040
gagaaaaatt actggaaaaa ccagtgtgag aggatgatga tggagaaggc cctctcggc    2100
acctcacaac ctcttgtccg gtttgagaaa gctggactta gggcagacca atcttctgcc   2160
agtggtcatt cttga                                                    2175
```

<210> SEQ ID NO 11
<211> LENGTH: 2173
<212> TYPE: DNA
<213> ORGANISM: Turkey astrovirus-2

<400> SEQUENCE: 11

```
atggccgata aggtcgttgt caagaagaca actacaaggc gcaggggcag gagtaattcc       60
cgctcccgta gcaggagtag gagcaggagc agaaataggg ttagaaagac agtcaaaatt     120
gttgagaaaa agccagaaaa atccatttg aagaaaattg accaggctga agaagagat       180
gaaaaacaaa tcaggcgaat gcggaaaaaa ttgcaaggac caccagtgaa ttccaggatg    240
```

```
acaacagtgg tcacacttgg tcagataaca ggtaacaaag acaacaccct agagcggaaa      300
cataagtgct ttctgaatcc gctgttgatg aagagtcagg aaaccggtca aactgcaacc      360
cccttatctg ttagggcatc ccaatataat ctgtggaagc tatccagact ccatgtcaga      420 cttataccccc ttgcaggaaa agcgaatatt ttggggtcag tggttttttct agatcttgag     480 caggaggcaa atacagcagg accagaatca gtagatacca tcaaagcaag accccatgtt      540
gaagttccca tagggtcaaa accgtctgg aaagtgcacc ctagaagtgc tctaggacct       600
agacaggggt ggtggaatgt tgatcctggt gacagcccaa ctgattctct ggggccagca      660
ctcaacatgt ggacctacct gcaaactgtc aatgcactcc agagcgccac tggtacacaa      720
acaccgtaca ccagtgcact tttccttgtg gaggtcttgg ttacgtatga gttttcaaat      780
tatggtccaa agcccgcact gtcccagatg gtatcagaca gctttccacc agcttccggc      840
tctactgcaa ccttaaaaaa caccagtgat ggggctgtag caatacaact ctcaggcgct      900
attgcccgaa agatggagga ggttgagccc aagggtaggc gctcaaatgc gcaaacatca      960
ggtgtcggtg aagtgttctg ggcagtgtcc actgaagtgg tcaacacagt agcagatgcc     1020
ataccaggct ggggctggct cctgaaaggt ggctggtttg tcctcaggaa aatctttggg     1080
gccgcgaatg accagaatgg cacttacttg atatactctt cagtggcaga tgcacaaggt     1140
gacaacagga tatacacatc agtgaaacag acacagttga catcaagcag gatcaacctc     1200
gtccaactca cccagcccaa tgtgaaccaa gcagcagtag gtggcagtgt tggtgcggca     1260
aactccatct atttgccact gccacaagca gatgatcaat acacacccta ttttgtttat     1320
aattttcaag gggaaagggt gtcaaccacc gagactgggg tattttgtct ggcagccata     1380
ccagcagcga ctacaactag taggtataat aatcagatca ccactccatc aattggctac     1440
aggaatgata gtggtacagg aacatcattc ctactagatg ctgcatcatg gtggaatata     1500
ttggatgtaa ctcaaactgg agtgctcttt ggacaaccaa gattgggtgt tggtgtcatg     1560
cagacaatga agactcttaa acagcatatc aaggattata cagagcctgc aatacagaaa     1620
tattatcctg gaacaaccaa ccttgatgag cagttgaaac agagattgaa cctggcagag     1680
ggtgacccgg tcatctcaat gggggacaca accggtagga gggctgcact cttttatagg     1740
actagtgatg aaaaatatat tttattttc tcaactacag aagatccagg gcacagtat     1800 caaaatctga aatgttgta cttttggaac tggtcctatt ctgacacgaa acagcaattt     1860
ttggaccacc tcagaacagt gcagtttgca aatttggatg acaaccatcc agcccctat     1920 gatagtgatg atgatgacct ttctgatgta acatcacttt ttgagcaggc tgatttgggg     1980
gatgagacag acttcaaatt taatatgtcc atccaaacct ccaaacatct tgaggaggag     2040
aaaaattact ggaaaaacca gtgtgagagg atgatgatgg agaaggccct ttcgggcacc     2100
tcacagcctc ttgtccggtt tgagaaagct ggacctaggg cagaccaatc ttctgccagt     2160
ggtcattctt gaa                                                       2173

<210> SEQ ID NO 12
<211> LENGTH: 2253
<212> TYPE: DNA
<213> ORGANISM: Turkey astrovirus-2

<400> SEQUENCE: 12
atgctctcca cagcaataac ggcacacaaa caccttacac cagtgcactt ttcattgtgc        60
aggtcttggt cacatatgag ttttcaatct atggtcccaa acctgcactg tcccacgatg       120
```

```
atttgggata gctttccacc agctgctggt tcagaagcaa ctctaaggaa caccagtgat      180
tgggttgttg cagtgcagct ttcgggtggt atcgcccgta ggatggagga agtgttgaac      240
ctaagagcag gcggtctaat gcacagacat caggtgttgg aaaagtgttt tgggcagtgt      300
ctgactgatg tagttaacac agtagcagat gatataccag ggtgggttgg gcttcctgaa      360
aggtggttgg tttgtgcctt aggtaagatt tccgctggtt atgaagagtc aggagaccgg      420
ccaaactgcg aacaccattg tcagttaggg catctcagta taattctgtg gaagttgtcc      480
agactccatg ttaggctgat acccctgca ggaaaagcaa acatcttggg atcagtggtg       540
ttcttagatc tagagcagga gtacgtgcag cgggaccag agtctgtgga taccatcaaa       600
gcaagacccc atgttgaagt tcctattggg gcgaaaactg tctggaaagt gcaccctaga      660
agtgccttag gtcccagaca agggtggtgg aatgttgacc ctggtgatag tccaactgat      720
tctcttggac cggcacttaa catgtggact tatttgcaaa ctgtcaatgc actccacagc      780
aataacggca cacaaacacc ttacaccagt gcacttttcc ttgtggaggt cttggtcaca      840
tatgagtttt caaactatgg tcccaaacct gcactgtccc agatgatttc ggatagcttt      900
ccaccagctg ctggttcaac tgcaactcta aaaaacacca gtgatggggc tgttgcagtg      960
cagctttcgg gtgctatcgc ccgtaggatg gaggaggttg aacctaagag caggcggtca     1020
aatgcacaga catcaggtgt tggagaagtg ttttgggcag tgtcaactga tgtagttaac     1080
acagtagcag atgctatacc aggctggggt tggctcctga aggtggctg gttcgtcctt      1140 aggaagatat ttggagctgc gaatgacgca aatagcacct acctgttgta ttcatcggta     1200
gctgatgcac agcaagacaa cagaatatat acaacaataa acaaggaca aggacaacta      1260 acatcaagtg tgatcaatct ggttcaactc acccagccaa atgtaaatca agcagctgtt     1320
ggtggtagtg ttggttctgc aaattccatc tacctaccct gccacaagc agaggatcaa      1380 tatacaccgc actttgttta tgatttccag ggaacgaggg tgtcaacaac agagtctgga     1440
gtcttttgcc tgtcctcaat accaagtgct gacagtaaga gcagatataa caaccagatg     1500
aactctccaa cagtgggata taagaatgaa ggtggtactg aacatcatt cgctatggac      1560 aatgccccgt ggtggagcat cctggatgtt actcaaacag gtgtcatctt tggccagccc     1620
aggttaggtg ttgggggttat acaaacaatg aaaaacactga acaacacat tacagatttt    1680 actgaacctg cagtaaagaa atattatcct ggcactacca acttggacca gacactcaaa    1740
gatagaatga aattaacaga aggagaccccg gtcgtctcta tgggagatgt gacagggaga    1800
agagcagcac tcttttatag aactagtgat gagaggtaca tcttgctcat ttcatcaaca    1860
gaagatcccg ggtcacaatt tgagaggctg aaggtgacaa cttcctggaa ctggtcccttt    1920 tctgacaaca aaagtgagtt cttaaatagg ttgagaacca tacagtatgc aaatgcacat    1980
caagaagaaa tgtctcattg tgatagcgac gatgatgggc tgtcagatgt aacgtcgctg    2040
tttgaacagg ccgacctgga ggatgagaca gatttttaaat ttaaaatgtc tattcaaacc    2100
tctaaagatc ttgaggatga gaaaaattac tggaaaaacc agtgtgagag gatgatgatg    2160
gagaaggccc tttcgggcac ctcacagcct cttgtccggt ttgagaaagc tggacctagg    2220
gcagaccaat cttctgccag tggtcatttt tga                                 2253
```

<210> SEQ ID NO 13
<211> LENGTH: 2182
<212> TYPE: DNA
<213> ORGANISM: Turkey astrovirus-2

<400> SEQUENCE: 13

```
atggcggcaa tggccgacaa ggtcgttgtt aagaagacaa ctacaaggcg caggggcagg        60
agtatttccc gctcccgtag caggagtagg agcaggagca gaactaggat taaaaagaca       120
gtcaagattg ttgagaaaaa gccagaaaaa tccatcttaa agaaaattga tcaggctgaa       180
aggagagatg aaaagcagat taggcggatt cgcaagaaaa tgcagggacc gccagtgaat       240
tctaggatga caacagtagt cacacttggt cagataacag gcataaaga caacaccta        300
gagcggaaac ataagtgctt tctgaatccg ctgctgatga agagtcagga aactggtcaa       360
actgcaacac ccttatctgt tagggcatcc aatataatc tgtggaagct atccagactc       420
catgtcagac ttataccct tgcaggaaaa gcaaatattt tggggtcagt ggtgttccta       480
gatcttgaac aggaggcaaa cacagcagga ccagaatcag tagataccat caaagcaaga       540
ccccatgttg aagttcccat agggtcaaaa actgtttgga aagtgcaccc tagaagtgct       600
ctaggaccta gacaggggtg gtggaatgtt gatcccggtg acagcccaac tgattctctt       660
gggccagcac tcaatatgtg gacctacctg caaactgtca atgcactcca gagcaccagt       720
ggtacacaaa caccttatac cagtgcactt tccttgtgg aggttttggt tacttatgag       780
tttcaaatt atggtccaaa gcccgcactg tcccagatgg tatcagacag ctttccacca       840
gcttccggct ctactgcaac cttaaaaaac accagtgatg gggctgtagc aatacaactc       900
tcaggcgcta ttgcccgaaa gatggaggag gttgagccca gggtaggcg ctcaaatgcg        960
caaacatcag gtgtcggtga agtgttctgg gcagtgtcca ctgaagtagt caatacagta      1020
gcagatgcca taccaggctg gggctggctc ctgaaaggtg gctggttttgt cctcaggaaa      1080
attttgggg ccgcgaatga ccagaatggc acttacttga tatactcttc agtggcagat       1140
gcacaaggtg acaacaggat atacacttca gtgaaacaga cacagttgat atcaagcagg      1200
atcaacctcg tccagctcac ccagcccaat gtgaaccaag cagcagtagg tggcagtgtt      1260
ggcacggcaa actccatcta cttgccacta ccacaagcag atgatcaata cacaccctat      1320
tttgtttata atttcaagg ggatagggtg tcaaccaccg aaactgggt attttgtctg        1380
gcagccatac cagctgcgac tacaactagt aggtataata atcagattac cactccatca      1440
attggctaca ggaatgctag tggtacagga acatcattcc tactagatgc tgcatcatgg      1500
tggaatata tggatgtaac tcagactgga gtgctctttg acaaccaag attgggtgtt        1560
ggtgttatgc agacaatgaa gactcttaaa cagcatatca aggattacac agagcctgca      1620
atacagaaat attatcctgg aacaaccaac cttgatgagc agttgaaaca gagattgaac      1680
ctggcagagg gtgacccggt catctcaatg ggggacacaa ccggtaggag ggctgcactc      1740
ttttatagga ctagtgatga aaaatatatt ttatttttct caaccacaga gatccaggt      1800
gcacagtatc aaaatttgaa aatgctgtac ttttggaact ggtcctactc tgacactaaa      1860
cagcaatttt tggaccacct tagaacagtg cagttcgcaa atttggatga cagccagcta      1920
gcccctatg atagtgatga tgatgacctt tctgatgtaa catcactttt tgagcaggct      1980
gatttggggg atgagacaga tttcaaattt aacatgtcca tccaaacctc caaacatctt     2040
gaggaggaga aaaattactg gaagaaccag tgtgagagga tgatgatgga aaggcccttt      2100
tcgggcacct cacagcctct tgtccggttt gagaaagctg gacctagggc agatcaatct      2160
tctgccagtg gtcattcttg ag                                              2182
```

<210> SEQ ID NO 14
<211> LENGTH: 2182
<212> TYPE: DNA

<213> ORGANISM: Turkey astrovirus-2

<400> SEQUENCE: 14

```
atggcggcaa tggccgacaa ggtcgttgtc aagaagacaa ctacaaggcg caggggcagg      60
agtaattccc gttcccgcag caggagtagg agcaggagca gaaccaggat taaaaagaca     120
gtcaaaattg ttgagaaaaa gccagaaaaa tccatcctaa aaaaaattga tcaggctgaa     180
agaagagatg aaagacagct caggcggatc cgtaagaaag tgccagggcc gccagtaaat     240
tccaggatga caacagtagt cacacttggt cagataacag gcaataaaga caacaccttta    300
gagcggaaac acaagtgctt tctgaatccg ctgttgatga agagtcagga aactggtcaa     360
actgcaacac ccttatctgt tagggcatcc aatataatc tgtggaacta ccaggactc      420
catgtcagac ttataccct tgcaggaaaa gcgaatattc tggggtcagt ggtgttttta     480
gaccttgaac aggaggcaaa tacagcagga ccagaatcag tagacaccat caaagcaaga    540
ccccatgttg aagttcccat agggtcgaaa accgtttgga aagtgcaccc tagaagtgct    600
ctaggaccta gacaggggtg gtggaatgtt gaccctggtg acagcccaac tgattctctt    660
gggccagcac tcaacatgtg gacctacctg caaactgtca atgcactcca gagcgctggg    720
ggcaaccaaa cgccttacac cagtgcactt ttccttgtgg aggtcttggt tacttatgag    780
tttttcaaact atggtccaaa gcctgcactg tctcaaatgg tatcagatag ttttccacca    840
tcctccggtt ctactgcaac cctaaaaaac accagtgatg gggctgtagc aatacaactc    900
tcaggcgcta tcgcccgaaa gatggaggag gttgagccca aggttaggcg ctcaaatgcg    960
caaacatcag gtgtcggtga agtgttctgg gcagtgtcca ctgaagtagt caatacagta   1020
gcagatgcca taccaggctg gggctggctc ctgaaggggtg gctggtttgt cctcaggaaa   1080
atctttgggg ccgcgaatga ccagaatggc acttacttga tatactcttc agtggcagat   1140
gcacaaggtg acaacaggat atacacatca gtgaaacaga cacagttgac atcaagcagg   1200
atcaacctcg tccaactcac ccagcccaat gtgaaccaag cagcagtagg tggcagtgtt   1260
ggtgcggcaa actctatata tttgccacta ccacaagcag atgaccaata tacaccctac   1320
tttgtctata attttcaagg ggaaagggtg tcaaccaccg agactggggt attttgtttg   1380
gcagccatac cagctgcgac tacatccagt aggtataata atcagatcac cactccatca   1440
ataggctaca ggaatgctag tggtacagga acatcattcc tactagatgc tgcatcatgg   1500
tggaatatat tggatgtaac tcagactgga gtgctctttg gacaaccaag attgggtgtt   1560
ggtgttatgc agacaatgaa gactctcaaa cagcatatca aggattacac agagcctgca   1620
atacagaaat attatcctgg aacaaccaac cttgatgagc agttgaaaca gagaytgaac   1680
ctggcagagg gtgacccggt catctcaatg ggggacacaa ccggtaggag ggctgcactc   1740
ttttatagga ctagtgatga gaaatacatt ttatttttct caaccacaga agatccaggg   1800
gcacagtatc aaaatctgaa aatgttgtac ttttggaact ggtcctattc tgacacgaaa   1860
cagcaatttt tggaccacct tagaacagtg cagtttgcaa atttggatga cagccatcca   1920
gcccctatg atagtgatga tgatgacctt tctgatgtaa catcactttt tgagcaggct    1980
gatttggggg atgagacaga cttcaaattt aatatgtcca tccaaacctc caaacatctt    2040
gaggaggaga aaaattactg gaaaaaccag tgtgagagga tgatgatgga gaaggccctt    2100
tcgggcacct cacagcctct tgtccggttt gagaaagctg gacctagggc agaccaatct    2160
tctgccagtg gtcattcttg aa                                               2182
```

<210> SEQ ID NO 15
<211> LENGTH: 1585
<212> TYPE: DNA
<213> ORGANISM: Turkey astrovirus-2

<400> SEQUENCE: 15

```
gaagttagaa gatcatgtgg tcagtggaga gtgtcaaaaa aactaataga ggggcctgtg      60
acaacaaagg cccctacccc cgtaccagat tggcttaaaa tatttgcatg ggaagatgat     120
atattaccac ccgaaggaaa aatcgcattg ccagaaaatg tcactctaat cgggcatata     180
ccagttgaca agttggtttc acgtaccaag aaagtccagg acccattgtt aggccttgta     240
acaccttgga acaggatgt gtatgactca acaacatgga ctgtaaaagc ttataacaaa      300
atgtttgaga aattccatta ccacgaccca gttgattttg tagagcaata tgctgagttt     360
gtgcttctgt gtgacaatat ggtgttgaga gagcatgatt atatggcaaa cagtcatatt     420
acaccaatta tgtcaacaga gaaaaatgtc aacagtacac cagcataccc gaaatttcaa     480
gcctatgata gtgaagctga gtatctggaa gattgtgggt ggcaagagta cctggatgtt     540
gtrtccgatc cagagtctat aaatcataga cccctatggt ggtgcttcct caaaaatgaa     600
gttctcaaga aagagaaaat tgaggataat gacatccgaa tgatactgtg caccgaccca     660
gttttcacca ggattggggc tatgtttgaa caggatcaga acaacagaat gaaacaacag     720
actgaaacaa gatctgcaca ggtaggatgg acacccttt tcggtggctt ggatcgcagg      780
gttcgtaggt tgtgtggaga tggagacagg tatttgttg agatggactg gacacggtat      840
gatgggacta taccaaaatc attattttgg agaattaggc aaattaggtt cttcttcctt     900
catgattctc ataagacccc aaagatgcgg cgtttgtaca attggtatgt gaaaaatttg     960
ttggaaaaaa ttatcttatt gccaactgga gaagtttgcc aggtcaagaa aggaaatccg    1020
agtggtcagt attcaacaac tgtggataat aatatgatca atgtctggct aacaacattt    1080
gaggtttcat acctattctt caaacagcgt ggtagactgc caacagagaa agagctgcaa    1140
gagaactgct ccatgatatg ctacggggat gacagacttc tttctatccg taaagggttt    1200
gttgagtacg aacctgacac agtcattgag atgtacaaga acatcttcgg gatgtgggta    1260
aaaagaaaca acatcaaaat ccaggacaca cctgaagggc tctcttttg tgggcttaca    1320
atagtgaaat caaatactgg tgcatatgtt ggtgttccca atgtgaacaa atattgtca     1380
accttggaaa atccagtacg taggctacca gatgttgagt ctctttgggg taaactggtt    1440
tccctgcgca tattgtgtga aaacgctccc agcaatgtta aacactttct tgatgagcag    1500
attagcaatg ttgaggagtt cgccgccaga gaaaacatac aacttcctga ggtcgggccc    1560
gacttctatt ccagaatatg gtgag                                         1585
```

<210> SEQ ID NO 16
<211> LENGTH: 804
<212> TYPE: DNA
<213> ORGANISM: Turkey astrovirus-2

<400> SEQUENCE: 16

```
aacaagatct gcacaggtag gatggacacc cttcttcggt ggcttggatc gcagggttcg      60
taggttgtgt ggggatggag acaggtattt tgttgagatg gactgacgc ggtatgatgg      120
gactataccaa agccattat tctggagaat tagacagatc aggttttct tcctccatga      180
ttcccataag accccaagaa tgcggcgcct gtacaattgg tatgttaaaa atttgctgga     240
aaaaatcatt ttgctaccaa ctggggaggt ctgccaggtt aagaaaggaa atccgagtgg     300
```

-continued

```
acaatattca acaactgtgg ataacaatat gataaatgtc tggctaacag cgtttgaaat    360
ttcatacctc tttttcaaac agtttggtag actgccaaca gagaaagaac tgcaagagaa    420
ctgctccatg atatgctacg gagatgacag acttctttcc atccgcaaag gatttgttga    480
gtatgaacct gatacagtca ttgagatgta caagaacatc tttggaatgt gggttaaaaa    540
aaataacatc aaaattcagg atacacccga agggctctct ttctgcgggc ttacaatagt    600
gaagtcaaga accggggcat atgttggagt cccaaatgtg aacaaaatat tgtcaacttt    660
ggaaaatcca gtccgcaggt tgccagatgt tgagtccttg tggggtaaat tggtttccct    720
gcgcatattg tgtgaaaatg ctcccagcaa tgttaaacat tttcttgatg agcagatgag    780
caatgttgag gagttcgccg ccag                                           804
```

<210> SEQ ID NO 17
<211> LENGTH: 807
<212> TYPE: DNA
<213> ORGANISM: Turkey astrovirus-2

<400> SEQUENCE: 17

```
aataaggtct gcacaggtcg gatggacacc ctttttcggt ggcttggatc gcagggttcg     60
taggttgtgt ggggatggag acaggtattt tgttgagatg gactggacgc ggtatgatgg    120
gactatacca aagccattat tctggaggat cagacagatt aggtttttct tcctccatga    180
ttcccataaa acctcaaaaa tgcggcgctt atacaattgg tatgtaaaaa atttgttgga    240
aaaaatcatc ttactgccaa ctggggaggt ctgccaggtt aagaaaggaa atccaagtgg    300
acaatattca acaactgtgg ataacaacat gataaatgtc tggctaacag catttgaaat    360
ttcatacctc tttttcaaac agtttggtag gctgccaaca gagaaagaac tgcaagagaa    420
ctgctccatg atatgctacg gagatgacag acttctttcc attcgcaaag ggtttgttga    480
gtatgaacct gaaacagtca ttgagatgta taagaacatc tttgggatgt gggttaaaaa    540
gactaacatc aagattcagg atacacccga agggctctct ttctgcgggc taacaatagt    600
gaaatcaaaa actggaacat atgttggtgt cccaaatgtg gacaaaatat tgtcaacttt    660
ggaaaatcca gtccgcaggt tgccagatgt tgagtccttg tggggtaaat tagtttccct    720
gcgcatattg tgtgaaaatg ctcccagcaa tgtcaaacat tttctcgatg agcagattgg    780
caatgttgtt gaggagttcg ccgccar                                        807
```

<210> SEQ ID NO 18
<211> LENGTH: 1564
<212> TYPE: DNA
<213> ORGANISM: Turkey astrovirus-2

<400> SEQUENCE: 18

```
tggagagtgc caaaaaaact agtagagggg cctgtgacaa caaaggcccc tacccccgta     60
ccagattggc ttaaaatatt tgcatgggaa gatgacatat taccacctga aggaaaaatt    120
gctttaccag aaaatgttac tctaattggg cacataccag ttgacaaatt ggtctcgcgt    180
accaagaaag tccaagaccc attgctaggc cttgtaacac catggaaaca agatgtgtat    240
gattcaacaa catggactgt aaaagcttac aacaaaatgt ttgagaaatt ccattaccac    300
gacccagttg attttgtaga gcaatatgct gagttcgtgc ttctgtgtga caacatggtg    360
ttgagagagc atgattatat ggcaaacagt catattacac caattatgtc aacagagaag    420
aatgtcaaca gtacaccagc atacccgaaa ttccaagcct atgatagtga agccgagtat    480
ttggaagatt gtgggtggca agagtatctg gatgttgtat ccgatccaga gtctataaat    540
```

```
catagacccc tatggtggtg cttcctcaaa aatgaagttc tcaaaaaaga gaaaattgag      600
gataatgata ttcgaatgat attgtgcacc gacccgattt tcaccaggat tggggctatg      660
tttgagcagg atcagaacaa cagaatgaaa caacagactg aaacaagatc tgcacaggtc      720
ggatggaccc ccttttttcgg cggcttggat cgcagggttc gtaggttgtg tggagatgga     780
gacaggtatt ttgttgagat ggactggacg cgatatgatg ggactatacc aaaatcacta     840
ttttggagga ttagacagat taggttttc ttccttcatg attcccataa gaccccaaaa      900
atgcagcgct tgtacaattg gtatgtaaaa aatttgctgg agaaaatcat tctattgcca      960
actggggagg tctgccaggt caagaaagga aatccgagtg gacaatattc aacaactgtg     1020
gacaacaata tgataaatgt ctggctaaca gcgtttgaaa tttcatacct cttcttcaaa     1080
cagtttggta gactgccaac agagaaagaa ctgcaagaga actgctccat gatatgctac     1140
ggagacgaca gacttctttc catccgcaag gggtttgttg agtatgaacc tgaaacagtc     1200
attgagatgt ataagaacat ctttggaatg tgggttaaaa agactaacat caagattcag     1260
gatacacccg aagggctctc tttctgtggg ctaacaatag tgaagtcaaa accgggaca      1320 tatgttggtg tcccaaatgt ggacaaaata ttgtcaactt tggaaaatcc agtccgtagg     1380
ttgccagatg ttgagatact tgtggggtaa agttcggttt ccctgcgcat attgtgtgaa     1440
aatgctccca gcaatgtcaa acattttctt gatgaacaga ttggcaatgt tgaggagttc     1500
gccgccaaag aaaacataca acttcctgag gtcgggcccg acttctattc cagaatatgg     1560
tgag                                                                  1564

<210> SEQ ID NO 19

<400> SEQUENCE: 19

000

<210> SEQ ID NO 20
<211> LENGTH: 803
<212> TYPE: DNA
<213> ORGANISM: Turkey astrovirus-2

<400> SEQUENCE: 20
ataaggtctg cacaggtcgg atggaccccc tttttcggcg gcttggatcg cagggttcgc       60
aggttgtgtg gtgatggata taggtatttt gttgagatgg actggacacg gtatgatggg     120
actataccaa aatcattatt ttggagaatt aggcaaatta ggttcttctt ccttcatgat     180
tctcataaga ccccaaagat gcggcgcttg tataattggt atgtgaaaaa tctgttggaa     240
aaaatcatct tattgccaac tggagaagtt tgccaggtta agaaaggaaa tccaagtggt     300
cagtattcaa caactgtgga taataatatg atcaatgtct ggctaacaac atttgaggtt     360 tcataccta tcttttaaaca gcgtggtaga ctgccaacag agaaagagct gcaagagaac     420
tgctccatga tatgctacgg ggatgacaga cttctttcca tccgtaaagg gtttgttgag     480
tacgaacctg atacagtcat tgagatgtac aagagcatct ttgggatgtg ggtaaaaaga     540
agcaacatca aaatccaaga tacacctgaa gggctctctt tttgtgggct acaatagta      600 aaatcaagtc tggtgcata tgttggtgtt cccaatgtga acaaaatatt gtcaaccttg      660
gaaaatccag tacgtaagct accagatgtt gagtctcttt ggggtaaatt ggtttccctg     720
cgcatattgt gtgaaaacgc tcccagcaat gttaaacact tcttgatga gcagattagc      780 aatgttgagg agttcgccgc caa                                             803
```

-continued

<210> SEQ ID NO 21
<211> LENGTH: 1585
<212> TYPE: DNA
<213> ORGANISM: Turkey astrovirus-2

<400> SEQUENCE: 21
gaagttagaa gaccatgtgg tcagcggaga gtgtcaaaaa aactagtaga ggggccygtg 60
acaacaaagg cccctacccc cgtaccagat tggcttaaaa tatttgcatg ggaagatgac 120
atattaccac ctgaaggaaa aattgcctta ccagaaaatg ttgccttaat tggacacata 180
ccagttgaca aattggtctc gcgtaccaag aaggtccaag accccctgtt aggccttgta 240
acgccttgga aacaggatgt gtatgactca acaacatgga ctgtaaaagc ttacaacaaa 300
atgtttgaga aatttcatta ccacgaccca gttgattttg tagagcagta tgctgagttt 360
gtgcttttgt gtgacaatat ggtgttgaga gagcatgact atatggcaaa tagttacatc 420
acaccaatta tgtcaacaga gaaaaatgtc aacagcacac cagcataccc gaaatttcag 480
gcctatgaca gtgaagccga gtatctggaa gattgtgggt ggcaagagta cctggatgtt 540
gtgtctgatc cagaaactat aaatcataga cccctgtggt ggtgcttcct caagaatgaa 600
gttctcaaaa aagagaaaat tgaggatagt gacattcgga tgatactgtg caccgaccca 660
gttttcacca ggattggggc tatgtttgaa caggaccaga acaacagaat gaaacaacag 720
actgaaacaa gatctgcaca ggtaggttgg acacccttct tcggcggctt ggatcgcagg 780
gttcgcaggt tgtgtggtga tggagacagg tattttgttg aaatggactg gacgcggtat 840
gatgggacta taccaaagcc actttttgg agaattagac agattaggtt tttctttctt 900
catgactccc ataaaactcc aaaaatgcgg tgtttgtaca attggtatgt aaaaaatttg 960
ttggaaaaag tcattttatt gccaactgga gaggtctgcc aagttaaaaa aggaaatccg 1020
agtggacaat attcaacaac tgtggataac aacatgataa atgtctggtt aacaacattt 1080
gagatttcat ttctcttttt caaacagcgt ggtagattgc caacagagaa agaattgcaa 1140
gagaactgct ccatgatatg ctatggggat gacagacttc tttctatccg caaagggttt 1200
gttgagtatg aacctgatac agttattgag atgtacaaga acatctttgg gatgtgggta 1260
aaaaggaata acattaaaat ccaagataca cctgaagggc tctctttttg tggacttaca 1320
attgtaaaat caagcaatgg ggcatatgtt ggagttccaa atgtgaacaa gatactgtca 1380
actttggaaa acccagtccg cagactgcca gatgttgagt ccttgtgggg taaattggtt 1440
tccctgcgca tattgtgtga aaatgctccc agcaatgtca aacactttct tgatgaacag 1500
attggcaatg ttgaggagtt cgccgccaga gaaaatatac aactgcctga agtcgggccc 1560
gacttctatt ccaaaatatg gtgag 1585

<210> SEQ ID NO 22
<211> LENGTH: 4080
<212> TYPE: DNA
<213> ORGANISM: Turkey astrovirus-2

<400> SEQUENCE: 22
aagtggggcg atggcccagg cgggtcgcag tggcgatgct tttgcatccc ttgatcaacg 60
gcgggagcgc caagaagaac aggcgcagtc cggccttgac aaggtgttct atttccaagg 120
cgtggttgaa ctattcaacc gtatgaaaat cgcctatgga aggacaccgg cttggacagc 180
cctcatgaag tgtaacgcca tatacttgaa agattttaaa acagcagttg gcgttgaggg 240

```
tacccgctat gggctctttt tcgcagaaga agtgactaaa ccaacttggt cacccgacat    300
tggagcaaac ttgataactt tgggcgaaaa ggcctgttta gacgcccaaa atgcaaaata    360
tgaaagattg caagcctcac ttaaaacaac tagtggcctt gttcatcaag tgatggaaaa    420
aactagggaa gctaaagaga acctagagaa agccaataag atccaagagc aacttgacaa    480
ggttattgag agcaacaaag ctttacaccg aagatacag gagaaaaacc gagagaagat    540
gcaggaatac atggtaaggt tgcataacac gcagaaagat cgtgatgatt gggttcaaag    600
atgctccagg ttagaacagg agaatgtcac gttgcagaaa aggttgaagg agaaagagaa    660
cgcgctggta tctgttgggt gggatctttt aggctggata gttatttcag ttctcgtgtt    720
cggcctgatt tcactcgcag acgcgcaaaa cttgactcca ccagccaaga ttgtgataac    780
tccagggcaa gcagagttta tggacctagc caaattggaa aaaatccaga tcagaaagta    840
ccgactggat agttgtgaat taccacctga gaaaggttgc gtgttgtaca aggattacct    900
taccaccagg ccggtaagct ttttggagtt gatggccaaa tgttcaaaac ctgactgggt    960
ctcggagagc agttacaatg aaacaactct aatggaagaa tgcgtccaga tctttggtgc   1020
agagtggtgt gaaggaaagc ttgttgatct tgtaccaaga aagtgtggcg agcaacatgt   1080
cttagttaac atcatagagc aaattgaaaa aactagagaa gttgtgaccc ttatatatag   1140
taaggtgatg tcatacaggc tagatatgtg gataacatct atttttagtt tagttttggc   1200
aggtaataag gaaaaattgt ttaaaatggc tccctttatc tttgtagcat ggttttttaaa   1260 tataccagtg ttttttaactt gtgtggcagt taacattttt ccagttgttt ccctgccttt   1320
cattttgttc cagattttta tgccacagtt tgttttggta aatgcctttc ttctatggtt   1380
aacactcact ttaacagcat tttattggag tgaggggccc aaaatactga tggagataag   1440
ctatgccctt gtgtatacca tcggctttgt tttatggtcc cttggactag ctgtgggggt   1500
gacgctcaaa ttgacaatgg tacatcagat attaatgttt tgtgttgttg ccgcagctat   1560
ttgcggaacc aagtttgcat gcacaacaat aacagtgcaa catccagatg aacaaccgc   1620 aaaatatacc cgggttggta agctaaagaa taatgttgtg aatcagtgca agaaggtagt   1680
cacgacattg cagacaagag gcgtgatacc agcaacgcct gcgaaaacag catctattgt   1740
tattgttgag ggcaaaaatg gaacaggcgt tgggttcagg tttatgaatt atattctcac   1800
agcagaacac gtggttcagg gatcagatat agcaacactt aaaagtggca gtgttagtgt   1860
gaaatccaaa gtcatcaaaa cgatcccaat atttgagagt gttgacaatg ttgcagtgct   1920 aaaaattgcca cctgagctca atagcgtgaa gcctatcaaa ttagcaaaga aggttcaaag   1980
tgactatctg acactgacag cctatgatcc aaatttccaa catgccgtta ctttcaccgg   2040
gtggtgtatt atagatggaa attggcttaa taactccttt gatacaaaat tgggaatag   2100 tggtgcacct tattgtgatc atgacggtag gctagttggt atccacctag gcacacaggg   2160
tgttctgtcc caaggcatag tcattgtaga cgcattgaag aatacattcc agcttgcgga   2220
tcagtgtaga ccacagaact tgacatggga tgagttcctt gagaaagtta tagcaggaac   2280
aaaagtgtca catgcagcga tcctaaaaga actggaagaa cttagagaag aggtgcaatt   2340
tttaaagaaa aaatgtgtca cttatgatga ctactggcta tgccaaacca tctttgggca   2400
ggccaaaggg aagacgaaga aaacagtcag aggccgtaaa caccttgtta ccaaaagagc   2460
tcttgggaaa ggccacttca tgaagatgag gatgctcact gatgaagaat atcagaatat   2520
gattgaaaag gcttctcag cagaggaaat aaggagagca gtcaacgcac tccgagagca   2580
agcatggctt aattactgta ttgataatga tgttgatgac gaaggtgagg aagattggta   2640
```

-continued

```
tgatgacatg gtagagacag atagagttaa ccaggagatc gatgaggcca tagagcgtgc    2700
catggaagat cgtggtgagt tctaccagaa gaaatcccgc cttacctttg ttgaacaggc    2760
catgatgcat ttgatccaag tgagcaaaga gagaagccag actgctaaat tagaagttca    2820
gaaggagaat gaagctcaac tagtgaagat gtttgagcgg tgtgtcacag atgagaatac    2880
acctgagggt accacctcta tagcggcttt gtccacagaa gatgatgtta ggcttgttga    2940
agggaaagtc attgatttca ccaaagcaaa gaatatccca gttgatgggg aaattagaag    3000
agagatcatt cctggaacaa aatgcactga gatttccact ggacctgaaa ataagaagaa    3060
catattgaag aaaaaggata cacacatagc tgagggtaaa gttgaaaata agtcatcaca    3120
gcagccggtt gacgttaagg atgataaacc cgtagccttg gaacaacgca agcctagagc    3180
ttgtaaatgg tgcggttcat cacaaaaaca tgattaccgg gaatgtcggt ttcaacgtga    3240
aaaacgcttt tgtgtgtatt gtgcagctat gcactcaatg tttgagggcc atataagacc    3300
aatagagtgc actagttgta agaaaagttt ttcaggaatt gagaagttag aagatcatgt    3360
ggtcagtgga gagtgtcaaa aaactagtga gagggcctg tgacaacaaa ggcccctacc    3420
cccgtaccag attggcttaa aatatttgca tgggaagatg cacatattac cacctgaagg    3480
taaaactgcc ttaccagcaa atgttaytc taattggtac atataccagt tgttkaagtt    3540
ggtctcgcgc accaagaaag tccaggatcc attgttaggc cttgtaacac catgraaaca    3600
agatgtgtat gattcawcaa catggactgy wrwagcttac accaamaatg ttkgagaart    3660
tccattacca cgacccagtt gactttgtag agcagtatgc tgagtttgtg ctgytgtgtg    3720
acaayatgrt gktgwkrarr saksaykaya tgryrrmtar caayatcaca ccaatcatsw    3780
cracagarra aaatrwyrwc artacamcas catmcymmmc tttgaagccc gggtgtcaca    3840
gatgagaaca cacctgaggg taccacctct atagcggctt tgtccacaga agatgatgtt    3900
aggcttgttg aagggaaagt cattgatttt accaaagcaa agaatatccc agttgatggg    3960
gaaattagaa gagagatcat tgcctggaac aaaatgcact gagatttgcc actggacctg    4020
aaaataagaa ggaacatatg taagaaaaag gcatacacac atagatgagg ckgaaaktga    4080
```

<210> SEQ ID NO 23
<211> LENGTH: 4922
<212> TYPE: DNA
<213> ORGANISM: Turkey astrovirus-2

<400> SEQUENCE: 23

```
ggcgatggcc caggcgggtc gcagtggcga tgcttttgca tcccttgatc aacggcggga     60
gcgccaagaa gaacaggcgc agtccggcct tgacaaggtg ttctacttcc aaggcgtggt    120
tgaattattc aaccgtatga aaatcgccta tggaaggaca ccggcttgga cggccctcat    180
gaagtgtaac gccatatact tgaaagattt taaaacagca gttggcgttg agggtacccg    240
ctatgggctc ttttcgcag aagaagtgac taaaccaact tggtcacccg acattggagc    300
aaacttgata actttgggcg aaaaggcctg tttagacgcc caaatgcaa atatgaaag    360 attgcaagcc tcactcaaaa caactagtgg ccttgtgcat caagtgatgg aaaaaactag    420
ggaagctaaa gagaacctag agaaagccaa taagatccaa gagcaacttg acaaggtcat    480
tgagagcaac aaagctttac accggaagat acaggagaaa aaccgagaaa agatgcagga    540
atacatggta aggttgcaca atacgcgaaa agatcgtgat gattgggttc agagatgctc    600
caggttagaa caggagaatg tcactttgca aaaaaggttg aaggagaaag agaacgcgct    660
```

-continued

```
ggtatctgtt gggtgggatc ttttaggctg gatagttatt tcagtgcttg tattcggcct    720
gatttcactc gcagacgcgc aaaacttgac tccaccagcc aagattgtga taactccagg    780
gcaagcagag ttcatggacc tagccaaatt ggaaaaaatc cagatcagaa agtaccgact    840
ggatagttgt gaattaccac ctgagaaagg ttgcgtgttg tacaaggatt accttaccac    900
caggccggta agcttttggg agttgatggc caaatgttca aaacctgact gggtttcgga    960
gagcagttac aatgaaacaa ctctaatgga agaatgcatc cagatctttg cgcagagtg    1020
gtgtgaagga aagcttgttg atctcgtacc aagaaagtgt ggcgagcaac atgtattagt   1080
taacatcata gagcaaattg aaaaaaccag agaagttgtg acccttatat atggtaaggt   1140
gatgtcatac aggctagata tgtggataac atctattttt agcctagttt tggcaggtaa   1200
caaggaaaaa ttgtttaaaa tggctcccct cattttgta gcatggtttt taaacatacc    1260
agtgttttta acttgtgtgg cagtcaacat ttttccagtt gtttccctgc ctttcatttt   1320
gttccagatt tttatgccac agtttgtttt ggtaaatgcc tttcttctat ggttaacact   1380
cactttaaca gcattttatt ggagtgaggg gcccaaaata ctgatggaga taagctatgc   1440
ccttgtgtat accatcggct ttgttttatg gtcccttgga ctagccgtgg gggtgacgct   1500
caaattgaca atggtacatc agatattaat gttttgtgtt gttgccgcag ctatttgcgg   1560
aaccaagttt gcatgcacaa caataacagt gcaacaccca gatggaacaa ccgcaaaata   1620
cacccgagtt ggtaagctaa agaataatgt tgtgaatcag tgcaagaagg tagtcacgac   1680
attgcagaca agaggcgtta taccagcaac gcctgcgaaa acagcatcta ttgttattgt   1740
tgagggcaaa aatggaacag gtgttgggtt caggtttatg aattatattc ttacagcaga   1800
acacgtggtt cagggatcag atatagcaac actcaaaaat ggcagtgtta gtgtgaaatc   1860
caaagttatc aaaacgatcc caatatttga gagtgttgac aatgttgcag tgttaaaatt   1920
accacctgag ctcaatagcg tgaagcctat caaattagca aagaaggttc aaagtgacta   1980
tctgacattg acagcctatg atccaaattt ccaacatgcc gttacttta ccgggtggtg    2040
tattatagat ggaaattggc ttaataactc ctttgacaca aaatttggga atagtggtgc   2100
accttattgt gatcatgacg gtaggctagt tggtatccat ctaggcacac agggtgttct   2160
gtcccaaggc atagtcattg tagatgcatt gaaaaataca ttccagcttg cggatcagtg   2220
tagaccacag aattttgaca tggatgagtt ccttgagaaa gttatagcag aacaaaagt    2280
gtcacatgca gcgatcctaa agaactgga agaacttaga gaagaggtgc aattttttgaa   2340
gaaaaaatgt gttacctatg atgactactg gctatgccaa accatctttg ggcaggccaa   2400
agggaagacg aagaaaacag tcagaggccg taaacacctt gttaccaaaa gggctcttgg   2460
gaaaggccac ttcatgaaga tgaggatgct cactgatgaa gaatatcaga atatgattga   2520
aaagggcttc tcagcagagg aaataaggga ggcagtcaac gcactccgag aacaagcatg   2580
gcttaattac tgtattgata tgatgttga tgacgaaggt gaggaagatt ggtatgatga    2640
catggtagag acagatagag ttaaccaaga gatcgatgag gccatagagc gtgctatgga   2700
agatcgtggt gagttctacc agaagaaatc ccgccttacc tttgttgaac aggccatgat   2760
gcatctaatc caagttagca aggagagaag ccagactgct aaattagaag ttcagaagga   2820
gaatgaagct caactagtga agatgtttga acggtgtgtc acagatgaga atacacctga   2880
gggtaccacc tctatagcgg ctttgtccac agaagatgat gttaggcttg ttgaagggaa   2940
agtcattgat ttcaccaaag caagaatat cccagttgat ggggaaatta ggagagagat   3000
catccctgga acaaaatgca ctgagatttc cactggacct gaaaataaga agaacatatt   3060
```

-continued

```
gaagaaaaag gacacacaca tagctgaggg taaagttgaa actaagtcat cacagcagcc      3120
ggttgacgtc aaggatgata aacccgtagc cttggaacaa cgtaagccta gagcttgtaa      3180
atggtgcggt tcatcacaga acatgatta ccgggaatgt cggtttcaac gtgaaaagcg       3240
cttttgtgtg tattgtgcag ctatgcactc aatgtttgag ggccacataa gatcaataga      3300
gtgcactagt tgcaagaaaa gttttcagg aattgagaag ttagaagatc atgtggtcag       3360
tggagagtgt caaaaaaact aatagagggg cctgtgacaa caaggcccc tacccccgta       3420
ccagattggc ttaaaatatt tgcatgggaa gatgacgtat taccacctga aggtaaaact     3480
gccttaccag aaaatgttac tttaattgga catataccag ttgataagtt ggtctcgcgc     3540
accaagaaag tccaggatcc attgttaggc cttgtaacac catggaaaca agatgtgtat     3600
gactcaacaa cgtggactgt aaaagcttac accaaaatgt ttgagaaatt ccattaccac     3660
gacccagttg actttgtaga gcaatatgct gagtttgtgc tgttgtgtga taatatggtg     3720
ttgagagagc atgactatat ggcaaatagc aatatcacac caatcatgtc aacagagaaa     3780
aatgtcaata gtacaccagc ataccccaaaa tttcaagcct atgatagtga agccgagtat    3840
ttggaagatt gtgggtggca agagtacctg gatgttgtgt ctgatccaga aactataaat    3900
cgtagacccc tatggtggtg cttcctcaaa aatgaagttc tcaaaaaaga gaaaattgag   3960
gacagtgaca ttcgaatgat attgtgcacc gacccagttt ttaccaggat tggggctatg    4020
tttgaacagg atcagaacaa cagaatgaaa caacagactg aaacaagatc agcacaggta    4080
ggatggacac ccttcttcgg cggcttggat cgcagggttc gcaggttgtg tggtgatgga   4140
gataggtatt tgttgagat ggactggacg cgatatgatg ggactatacc aaaatcacta    4200
ttttggagga ttaggcaaat taggttcttc ttccttcatg attctcataa gaccccaaag   4260
atgcggcgct tgtacaattg gtatgtgaaa aatctgttgg aaaaaaattat tttattgcca    4320
actggagaag tttgccaggt caagaaagga atccaagtg gtcagtattc aacaactgtg   4380
gataataata tgatcaatgt ctggctaaca acatttgagg tttcataccct attcttcaaa   4440
cagcgtggta gactgccaac agagaaagag ctgcaagaga actgctccat gatatgctac   4500
ggggatgaca gacttctttc catccgtaaa gggtttgttg agtacgaacc tgatacagtc   4560
attgagatgt acaagaacat ctttgggatg tgggtaaaaa gaaacaacat taaaatccaa   4620
gatacacctg aagggctctc ttttttgtggg cttacaatag taaaatcaag tgctggtgca   4680
tatgttggtg ttcccaatgt gaacaaaata ctgtcaaccct tgggaaatcc agtacgtagg  4740
ctaccagatg ttgagtctct ttgggggtaaa ttggtttccc tgcgcatatt gtgtgaaaac  4800
gctcccagca atgttaaaca cttttcttgat gagcagatta gcaatgttga ggagttcgcc  4860
gccagagaaa acatacaact tcctgaggtc gggcccgact tctattccag aatatggtga  4920
ga                                                                   4922
```

<210> SEQ ID NO 24
<211> LENGTH: 3378
<212> TYPE: DNA
<213> ORGANISM: Turkey astrovirus-2

<400> SEQUENCE: 24

```
atggcccagg cgggtcgcgg cagcgatgct tttgcatccc ttgatcaacg ccgggagcgc       60
caagaagaac aggcgcaaac cggccttgac aaggtgtttt tcttccaagg cgtggttgag      120
ttattcaacc gcatgaaaat tgcctatgga aggacaccgg cgtggacagc cctcatgaag     180
```

-continued

```
tgtaacgcca tatatttgaa agatttcaaa acagcaattg gcgttgaggg tacccgctat    240
gggttattct tcgcagaaga agtgaccaaa ccaacctggt cacccgacat ggagcaaat     300 ttgatgacct tgggcgaaaa ggcttgtata gacgcccaga atgcaaaata tgaaagattg    360
caagcatcac ttaaaacaac cagtgcccta gtgcaccaag tgatggaaaa aactagggag    420
gctaaagaga atttggagaa agctaataag atccaagatc agcttgacaa ggttgttgaa    480
agcaataaga ccttacaccg gaggatacag agaaaaacc gagagaagat gcaggagtat     540
atggtgaggt tgcataacac gcagaaggat cgtgatgact gggttcagag atgctctagg    600
ctggaacagg agaatgtcaa tctgcagaaa aggttaaagg agaaagagaa tgcgctgata    660
tctgttggat gggatctttt aggctggata gttatttcag tgcttgtatt cggcctgatt    720
tcacttgcag acgcgcagaa cctgactcca ccagccaaga ttgtgataac tccaggacaa    780
gcagagttca tggacctagc taaattggaa aaaatccaga tcagaaagta tcgactggag    840
agttgtgagt taccacctga gaaaggttgc gtattgtata aggattatct caccaccagg    900
tcagtaagct tcttggagtt gatggccaaa tgtacaaaac ctgactggat ctcggagagc    960
agttataatg aaacaaccct tatggaagag tgcattcaga ttttcggtgc agagtggtgt   1020
gaaggaaaac ttgttgacct tgtgccaagg aaatgtagtg aacaacatat tctagttaat   1080
tttatggagc aaattgaaaa aactagagaa gttgtaaccc tcatatatgg gaaggtgatg   1140
tcatacaggt tggatatgtg gataacatcc atcttcagct tagttttagc aggtaataag   1200
gaaaaattgt ttaaaatggc tccttttatt cttgtggcat ggttttttgcg tataccagtg   1260 tttttgacct gcgtggcagt taacattttt ccgcttgttt cactgccctt tatattgttt   1320
cagatcttta tgccacagtt tgtcctgata aatgctttcc tcttatggtt aacactcact   1380
ttaacagctt tttattggaa tgaggggccc aaaatactta tggaggtgag ctatgccctt   1440
gtgtatacca tcggctttgt tttatggtct cttggattgg ctgtgggtgt gacgcttaaa   1500
ttgacaatgg tacatcagat attgatgttt tgtgttgttg tcgcaaccat tgtgggacc    1560 agatttgcat gcgcaacaat aacagtgcaa cacccagatg gaacaaccac aaaatacacc   1620
cgggttggta agttaaagac aaatgtagtg aatcagtgta gaagatggt cacgacactg     1680 caaacaagag gcgtaatacc agcaacgcct gcaaaaacag catccattgt tattgttgag    1740
ggaaaaaatg gaacaggtgt cggtttcagg tttatgaatt atatccttac agcagagcat    1800
gtggttcagg gatcggatat agcaacactt aaaaatggca gtgttagtgt gaaatccaaa    1860
gttattaaaa cgatcccaat atttgaaagt gttgataatg ttgcagtgtt aaaattacca    1920
cctgagctta atggcgtgaa acctattaaa ttagcaaaga gggttcaaag tgactatttg    1980
acactgacag cytatgatcc aacatttcaa cacgccgtca cttacaccgg gtggtgtata    2040
gtggatggga attggcttaa taattctttt gatacaaaat ttggaaatag tggtgcacca    2100
tattgcgacc atgatggtag ctagttggt atccacctag gcacacaggg tgttctgtcc    2160
caaggcatag tcattgtaga tgcattgaag aatacattcc agcttgcaga tcagtgtaga    2220
ccacagaact ttgatatgga tgagttcctt gagaaagtca tagcaggaac aaaagtttca    2280
cacgcagcga tcttaaaaga actggaagaa cttagagaag aggtgcaatt tttgaaaaga    2340
aaatgtgtca cctacgatga ctactggcta tgccaaacca tctttgggca ggccaaaggg    2400
aagacgaaga aaacagtcag aggccgtaaa caccttgtta ctaaaagagc tcttagtaag    2460
gggcatttta tgaagatgag gatgcttacc gatgaagaat atcagaacat gattgaaaag    2520
ggcttctcag cagaggaaat aagagaggca gtcaatgaac tccgggaaca agcatggctc    2580
```

```
aattattgta ttgataatga cattgacgat gaaggtgagg atgactggta tgatgatatg    2640
gtagagacag acagggttaa tcaggagatt gatgaggcta tagagcgtgc catggaagat    2700
cgtggtgaat ctaccaaaa gaagtctcgc cttacttttg tcgagcaggc catgatgcat    2760
ctgattcaag taagtaagga gaggagccag actgccaagt tagaagtcca aaggagaat    2820 gaagaacaac taaaaaacat gtttgagcgg tgtgtcacag atgagaatac acctgagggc    2880
accacttcag tagcagtttt gtccacagag gaggatgtta ggcttgttga agggaaaatc    2940
attgacttct ccaaagcaaa aaatattcca gttgacgggg agataaggag agagataatt    3000
cccgggacta agtgcactga gatttctact ggacccgaaa ataggaagaa catattgaag    3060
aaaaaggata cacacatgac tgagggaaaa gttgagacta aacatcaca gcaaccggtt    3120 gacgttaaag atgataaacc cgtagccttg gaacaacgga agcctagagc ttgtaaatgg    3180
tgcggttcat cacaaaaaca cgattaccgg gaatgtcggt ttcaacgtga aaaacgtttc    3240
tgtgtgtatt gtgcagctat gcactcaatg tttgagggcc acataagatc gatagagtgc    3300
gccaactgta agaagagttt cccaggaatt gagaagttag aagaccatgt ggtcagcgga    3360
gagtgtcaaa aaaactag                                                  3378
```

<210> SEQ ID NO 25
<211> LENGTH: 2162
<212> TYPE: DNA
<213> ORGANISM: Artificial Sequence
<220> FEATURE:
<223> OTHER INFORMATION: A synthetic consensus sequence

<400> SEQUENCE: 25

```
atggcggcaa tggccgacaa ggtcgttgtc aagaagacaa ctacaaggcg cagggggcagg      60 agtaattccc gctcccgtag caggagtagg agcaggagca gaacaggtta aaaagacagt    120
caaaattttg agaaaagcc agaaaaatcc atcttaaaga aaattgacca ggctgaaaga    180
agagatgaaa acagatcagg cggatcggaa aaatgcaggg gccgccagtg aattccagga    240
tgacaacagt agtcacactt ggtcagataa caggcaataa agacaacacc ttagagcgga    300
aacataagtg ctttctgaat ccgctgttga tgaagagtca ggaaactggt caaactgcaa    360 caccctatc tgttagggca tcccaatata atctgtggaa gctatccaga ctccatgtca    420
gacttatacc ccttgcagga aaagcgaata ttttggggtc agtggtgttc ttagatcttg    480
aacaggaggc aaaacagcag gaccagaatc agtagatacc atcaaagcaa acccccatgt    540
tgaagttccc atagggtcga aaactgtttg gaaagtgcac cctagaagtg ctctaggacc    600
tagacagggg tggtggaatg ttgaccctgg tgacagccca actgattctc ttgggccagc    660
actcaacatg tggacctacc tgcaaactgt caatgcactc cagagcgcta gggcacacaa    720
acaccttaca ccagtgcact tttccttgtg gaggtcttgg ttactatgag ttttcaaact    780
atggtccaaa gcctgcactg tcccagatgg tatcagacag ctttccacca gcttccggtt    840
ctactgcaac cctaaaaaac accagtgatg gggctgtagc aatacaactc tcaggcgcta    900
tcgcccgaaa gatggaggag gttgagccca agggtaggcg ctcaaatgcg caaacatcag    960
gtgtcggtga agtgttctgg gcagtgtcca ctgaagtagt caacacagta gcagatgcca   1020
taccaggctg gggctggctc ctgaaaggtg gctggtttgt ccttaggaaa attttggggc   1080
cgcgaatgac cagaatggca cttacttgat atactcttca gtggcagatg cacaaggtga   1140
caacaggata tacacatcag tgaaacagac acagttgaca tcaagcagga tcaacctcgt   1200
```

-continued

```
ccaactcacc cagcccaatg tgaaccaagc agcagtaggt ggcagtgttg gtcggcaaac    1260
tccatctatt tgccactacc acaagcagat gatcaatata cccctactt tgtttataat    1320 tttcaagggg aagggtgtca accaccgaga ctggggtatt tgtctggca gccataccag    1380 ctgcgactac aacagtaggt ataataatca gatcaccact ccatcaattg gctacaggaa    1440
tgctagtggt acaggaacat cattcctact agatgctgca tcatggtgga atatattgga    1500
tgtaactcag actggagtgc tctttggaca accaagattg ggtgttggtg ttatgcagac    1560
aatgaagact ctaaacagca tatcaaggat tatacagagc ctgcaataca gaaatattat    1620
cctggaacaa ccaaccttga tgagcagttg aaacagagat gaacctggca gagggtgacc    1680
cggtcatctc aatgggggac acaaccggta ggagggctgc actcttttat aggactagtg    1740
atgaaaaata cattttattt ttctcaacac agaagatcca ggggcacagt atcaaaatct    1800
gaaaatgttg tacttttgga actggtccta ttctgacaca acagcaatt tttggaccac    1860 cttagaacag tgcagtttgc aaatttggat gacagccacc agcccctat gatagtgatg    1920 atgatgacct ttctgatgta acatcacttt ttgagcaggc tgatttgggg gatgagacag    1980
atttcaaatt taatatgtcc atccaaacct ccaaacatct tgaggaggag aaaaattact    2040
ggaaaaacca gtgtgagagg atgatgatgg agaaggccct ttcgggcacc tcacagcctc    2100
ttgtccggtt tgagaaagct ggacctaggg cagaccaatc ttctgccagt ggtcattctt    2160
ga                                                                  2162
```

<210> SEQ ID NO 26
<211> LENGTH: 3375
<212> TYPE: DNA
<213> ORGANISM: Turkey astrovirus

<400> SEQUENCE: 26

```
atggcccagg cgggtcgcag tggcgatgct tttgcatccc ttgatcaacg gcgggagcgc      60
caagaagaac aggcgcagtc cggccttgac aaggtgttct acttccaagg cgtggttgaa     120
ctattcaacc gtatgaaaat cgcctatgga aggacaccgg cttggacggc cctcatgaag     180
tgtaacgcca tatacttgaa agatttcaaa acagcagttg gcgttgaggg tacccgctat     240
gggctctttt tcgcagaaga agtgactaaa ccaacttggt cacccgacat tggagcaaac     300
ttgataactt tgggcgaaaa ggcctgttta gacgcccaaa atgcaaaata tgaaagattg     360
caagcctcac ttaaaacaac tagtggcctt gtgcatcaag tgatggaaaa aactagggaa     420
gctaaagaga acctagagaa agccaataag atccaagagc aacttgacaa ggtcattgag     480
agcaacaaag ctttacaccg taagatacag gagagaaacc gagaaaagat gcaggaatac     540
atggtaaggt tgcataacac gcagaaagat cgtgatgatt gggttcagag atgctccagg     600
ttagaacagg agaatgtcac attgcagaaa aggttgaagg agaaagagaa cgcgctggta     660
tctgttgggt gggatctttt aggctggata gttatttcag tgcttgtatt cggcctgatt     720
tcactcgcag acgcgcaaaa cttgactcca ccagccaaga ttgtgataac tccagggcaa     780
gcagagttca tggacctagc taaattggaa aaaatccagg tcagaaagta ccgactggat     840
agttgtgaat taccacctga gaaaggttgc gtgttgtaca aggattacct taccaccagg     900
ccggtaagct ttttggagtt gatggccaaa tgttcaaaac ctgactgggt ctcggagagc     960
agttacaatg aaacaacccct aatggaagaa tgcatccaga tctttggtgc agagtggtgt    1020
gaagggaagc tcgttgatct tgtaccaaga aagtgtggcg agcaacatgt cttagttaac    1080
atcatagagc aaattgaaaa accagagaa gttgtgaccc ttatatatgg taaggtgatg    1140
```

-continued

| | |
|---|---|
| tcatacaggc tagatatgtg gataacatct attttagtt tagttttggc aggtaataag | 1200 |
| gaaaaattgt ttaaaatggc tcccttcatt tttgtagcat ggttttaaa cataccagtg | 1260 |
| tttttaactt gtgtggcagt caacatttt ccagttgttt ccctgccttt cattttgttc | 1320 |
| cagattttta tgccacagtt tgttttggta aatgcctttc ttctatggtt aacactcact | 1380 |
| ttaacagcat tttattggag tgaggggccc aaaatactga tggagataag ttatgccctt | 1440 |
| gtgtatacca tcggctttgt tttatggtcc cttggactag ctgtgggggt gacgctcaaa | 1500 |
| ttgacaatgg tacatcagat attaatgttt tgtgttgttg ccgcagctat ttgcggaacc | 1560 |
| aagtttgcat gcacaacaat aacagtgcaa cacccagatg aacaaccgc aaaatacacc | 1620 |
| cgggttggta agctaaagaa taatgttgtg aaccagtgca aaaaggtagt cacgacattg | 1680 |
| cagacaagag gcgttatacc agcaacgcct gcgaaaacag catctattgt tattgttgag | 1740 |
| ggcaaaaatg gaacaggtgt tgggttcagg tttatgaatt atattcttac agcagaacac | 1800 |
| gtggttcagg gatcagatat agcaacactt aaaaatggca gtgttagtgt gaaatccaaa | 1860 |
| gtcatcaaaa cgatcccaat atttgagagt gttgacaatg ttgcagtgtt aaaattgcca | 1920 |
| cctgagctca atagcgtgaa gcctatcaaa ttagcaaaga aggttcaaag tgactatctg | 1980 |
| acactgacag cctatgatcc aaattttcaa catgccgcca cttttaccgg gtggtgtatt | 2040 |
| atagatggaa attggcttaa taactccttt gatacaaaat ttgggaatag tggtgcacct | 2100 |
| tattgtgatc atgatggtag gctagttggt atccacctag gcacacaggg tgttcttccc | 2160 |
| caaggcatag tcattgtaga cgcattgaaa aatacattcc agcttgcgga tcagtgtaga | 2220 |
| ccacagaatt ttgacatgga tgagttcctt gagaaagtta tagcaggaac aaaagtgtca | 2280 |
| catgcagcga tcctaaaaga actggaagaa cttagagaag aggtgcaatt tttaaagaaa | 2340 |
| aaatgtgtca cctatgatga ctactggcta tgccaaacca tctttgggca ggccaaaggg | 2400 |
| aagacgaaga aaacagtcag aggccgtaaa caccttgtta ccaaaagagc tcttgggaaa | 2460 |
| ggccacttca tgaagatgag gatgctcact gatgaagaat atcagaatat gattgaaaag | 2520 |
| ggcttctcag cagaggaaat aagggaggca gtcaacgcac tccgagaaca agcatggctt | 2580 |
| aattattgta ttgataatga tgttgatgac gaaggtgagg aagattggta tgatgacatg | 2640 |
| gtagagacag atagagttaa ccaggagatc gatgaggcca tagagcgggc catggaagat | 2700 |
| cgtggtgagt tctaccagaa gaaatcccgc cttacctttg ttgaacaggc catgatgcat | 2760 |
| ttgattcaag tgagcaagga gagaagccag actgctaaac tagaagttca aaaggagaat | 2820 |
| gaagcccaac tagtgaagat gtttgagcgg tgtgtcacag atgagaatac acctgagggt | 2880 |
| accacctcta tagcggcttt gtccacagaa gatgatgtta ggcttgttga agggaaagtc | 2940 |
| attgatttca ccaaagcaaa gaacatccca gttgacgggg aaattaggag agagatcatc | 3000 |
| cctggaacaa aatgtactga gatttccact ggacctgaaa ataagaagaa catattgaag | 3060 |
| aaaaaggata cacacatagc tgagggtaaa gttgaaacta agtcatcaca gcagccggtt | 3120 |
| gacgtcaagg atgataaacc cgtagccttg gaacaacgta agcctagagc ttgtaaatgg | 3180 |
| tgcggttcat cacagaaaca tgattaccgg gaatgtcggt ttcaacgtga aaaacgcttt | 3240 |
| tgtgtgtatt gtgcagctat gcactcaatg tttgagggcc atataagacc aatagagtgc | 3300 |
| actagttgca agaaaagttt ttcaggaatt gagaagttag aagatcatgt ggtcagtgga | 3360 |
| gagtgtcaaa aaac | 3375 |

<210> SEQ ID NO 27

<211> LENGTH: 1581
<212> TYPE: DNA
<213> ORGANISM: Turkey astrovirus

<400> SEQUENCE: 27

| | | |
|---|---|---|
| gaagttagaa gatcatgtgg tcagtggaga gtgtcaaaaa aactaataga ggggcctgtg | 60 |
| acaacaaagg cccctacccc cgtaccagat tggcttaaaa tatttgcatg ggaagatgac | 120 |
| atattaccac ctgaaggtaa aactgcctta ccagaaaatg ttactctaat tggacatata | 180 |
| ccagttgata agttggtctc gcgcaccaag aaagtccagg atccattatt aggccttgta | 240 |
| acaccatgga acaagatat gtatgattca acaacatgga ctgtaaaggc ttacaccaaa | 300 |
| atgtttgaga aattccatta ccacgaccca gttgactttg tggaacagta tgctgagttt | 360 |
| gtgctgttgt gtgacaatat ggtgttgaga gagcatgact atatggcaaa tagcaacatc | 420 |
| acaccaatca tgtcaacaga gaaaaatgtc aatagtacac cagcataccc aaaattccaa | 480 |
| gcctatgaca gcgaagccga gtatttggaa gattgtgggt ggcaagagta cctggatgtt | 540 |
| gtgtctgatc cagaaactat aaatcgtaga cccctatggt ggtgcttcct caaaaatgaa | 600 |
| gttctcaaaa gagagaaaat tgaggacagt gacattcgaa tgatattgtg caccgacccg | 660 |
| attttacca ggattggggc tatgtttgag caggatcaga caacagaat gaaacaacag | 720 |
| actgaaataa ggtctgcaca ggtcggatgg accccctttt tcggcggctt ggatcgcagg | 780 |
| gttcgcaggt tgtatggtga tggagatagg tattttgttg agatggactg gacacggtat | 840 |
| gatgggacta taccaaaatc actattttgg agaattaggc aaatcaggtt cttcttcctc | 900 |
| catgattctc ataagactcc aaagatgcgg cgcttgtaca actggtatgt gaaaaatctg | 960 |
| ttggaaaaaa ttattttatt gccaactgga gaagtttgcc aggtcaagaa aggaaatcca | 1020 |
| agtggtcagt tttcaacaac tgtggataat aatatgatca atgtctggct aacaacatt | 1080 |
| gaggtttcat acctatttt caaacagcgt ggtagactgc caacagagaa agagctgcaa | 1140 |
| gagaactgct ccatgatatg ctacggggat gacagacttc tttccatccg taagggtttt | 1200 |
| gttgagtacg aacctgatac agtcattgat atgtacaaaa acatctttgg aatgtgggtg | 1260 |
| aaaagaaaca acatcaaaat ccaagataca cctgaagggc tctcttttg tgggcttaca | 1320 |
| atagtaaaat caagtactgg tgcatatgtt ggtgttccca atgtgaacaa atactgtca | 1380 |
| actttggaaa atccagtacg taggctacca gatgttgagt ctctttgggg taaattggtt | 1440 |
| tccctgcgca tattgtgtga aaatgctccc agcaatgtta aacactttct tgatgagcag | 1500 |
| attagcaatg ttgaggagtt cgccgccaga gaaaacatac aacttcctga ggtcgggccc | 1560 |
| gacttctatt ccagaatatg g | 1581 |

<210> SEQ ID NO 28
<211> LENGTH: 2175
<212> TYPE: DNA
<213> ORGANISM: Turkey astrovirus

<400> SEQUENCE: 28

| | | |
|---|---|---|
| atggcggcga tggccgacaa ggtcgttgtc aagaagacaa ctacaaggcg caggggcagg | 60 |
| agtaattccc gctcccgtag caggagtagg agcaggagca gaactaaaaa gacagtcaaa | 120 |
| attattgaga aaaagccaga aaatccatc ctaaagaaaa ttgatcaggc tgaaagaaga | 180 |
| gatgcaaaac agcttaggcg gattcgtaag aaagtgcagg gaccgccagt aaattccagg | 240 |
| atgacaacag tagtcacact tggtcagata acaggcaata aagacaacac cctagagcgg | 300 |
| aaacacaagt gctttctgaa tccgctgttg atgaagagtc aggaaactgg tcaaactgca | 360 |

```
acacccttat ctgttagggc atcccaatat aatctgtgga agctatccag actccatgtc    420
agacttatac cccttgcagg aaaagcgaat attttggggt cagtggtgtt cttagatctt    480
gaacaggagg caaacacagc aggaccagaa tcagtagata ccatcaaggc aagaccccat    540
gttgaagttc catagggtc gaaaaccgtt tggaaagtgc accctagaag cgctctagga     600
cctagacagg ggtggtggaa tgttgaccct ggtgacagcc caactgattc tcttgggcca    660
gcactcaaca tgtggaccta cctgcaaact gtcaatgcac tccagagcgc tggggcact     720 caaacgcctt acaccagtgc acttttctct gtggaggtct tggtcactta tgagttttca    780
aactatggcc caaagcctgc actgtctcaa atggtatcag acagctttcc accagcctcc    840
ggttctactg caaccttaaa aaacaccagt gatggggctg tagcaataca actctcaggc    900
gctatcgccc gaaagatgga ggaggttgag cccaagggta ggcgctcaaa tgcgcaaaca    960
tcaggtgtcg gtgaagtgtt ctgggcagtg tccactgaag tagtcaatac agtagcagat   1020
gccataccag gctggggctg gctcctgaaa ggtggctggt ttgtccttag gaaaatcttt   1080
ggggccgcaa atgaccagaa tggcacttac ttgatatact cttcagtggc agatgcacaa   1140
ggtgacaaca ggatatacac atcagtgaaa cagacacagt tgacatcaag caggatcaac   1200
ctcgtccaac tcacccagcc caatgtgaac caagcagcag taggtggcag tgttggtgcg   1260
gcaaactcca tctatttgcc actaccacaa gcagatgacc aatacacacc ctactttgtc   1320
tataattttc aaggggaaag ggtgtcaacc accgagactg gggtattttg tctggcagcc   1380
ataccagctg cgactacatc tagtaggtat aataatcaga tcaccactcc atcaattggc   1440
tacaggaatg ctagtggtac aggaacatca ttcctactag atgctgcatc atggtggaat   1500
atattggatg taactcagac tggagtgctt tttggacaac caagattggg tgttggtgtc   1560
atgcagacaa tgaagactct caaacagcat atcaaggatt acacagagcc tgcaatacag   1620
aaatattatc ctggaacaac taaccttgat gagcagttga agcagagatt gaacctggca   1680
gagggtgacc cggtcatctc aatggggac acaaacggta ggagggctgc actctttat    1740 aggactagtg atgaaaaata tattttattt ttctcaacca cagaagatcc aggggcacag   1800
tatcaaaatc tgaaaatgtt gtacttctgg aactggtcct attctgacac aaaacagcaa   1860 ttttggacc accttagaac agtgcagttt gcaaatttgg atgacagcca gccagccccc   1920
tatgatagtg atgatgatga cctttctgat gtaacatcac tttttgagca ggctgatttg   1980
ggggatgaga cagacttcaa atttaatatg tccatccaaa cctccaaaca tcttgaggag   2040
gagaaaaatt actggaaaaa ccagtgtgag aggatgatga tggagaaggc cctttcgggc   2100
acctcacagc ctcttgtccg gtttgagaaa gctggaccta gggcagacca atcttctgcc   2160
agtggtcatt cttga                                                    2175
```